(12) United States Patent
Sackstein

(10) Patent No.: US 10,370,642 B2
(45) Date of Patent: *Aug. 6, 2019

(54) HEMATOPOIETIC PROGENITOR CELL POPULATIONS HAVING AFFINITY FOR E-SELECTIN / L-SELECTIN

(71) Applicant: Robert Sackstein, Sudbury, MA (US)

(72) Inventor: Robert Sackstein, Sudbury, MA (US)

(73) Assignee: Robert Sackstein, Sudbury, MA (US)

( * ) Notice: Subject to any disclaimer, the term of this patent is extended or adjusted under 35 U.S.C. 154(b) by 62 days.

This patent is subject to a terminal disclaimer.

(21) Appl. No.: 14/599,211

(22) Filed: Jan. 16, 2015

(65) Prior Publication Data

US 2016/0201033 A1    Jul. 14, 2016

Related U.S. Application Data

(63) Continuation of application No. 13/529,530, filed on Jun. 21, 2012, now Pat. No. 9,523,078, which is a continuation of application No. 13/012,367, filed on Jan. 24, 2011, now abandoned, which is a continuation of application No. 10/042,421, filed on Oct. 18, 2001, now Pat. No. 7,875,585.

(60) Provisional application No. 60/297,474, filed on Jun. 11, 2001, provisional application No. 60/240,987, filed on Oct. 18, 2000.

(51) Int. Cl.
*C12N 5/16* (2006.01)
*C12N 5/0789* (2010.01)
*C07K 14/705* (2006.01)
*A61K 35/12* (2015.01)

(52) U.S. Cl.
CPC ...... *C12N 5/0647* (2013.01); *C07K 14/70585* (2013.01); *A61K 2035/124* (2013.01); *C12N 2501/59* (2013.01); *C12N 2501/599* (2013.01); *C12N 2501/724* (2013.01); *C12N 2501/90* (2013.01)

(58) Field of Classification Search
None
See application file for complete search history.

(56) References Cited

U.S. PATENT DOCUMENTS

| | | | |
|---|---|---|---|
| 5,652,343 | A | 7/1997 | Lasky et al. |
| 5,744,361 | A | 4/1998 | Hoffman et al. |
| 5,849,898 | A | 12/1998 | Seed et al. |
| 5,858,752 | A | 1/1999 | Seed et al. |
| 5,942,417 | A | 8/1999 | Ni et al. |
| 6,124,267 | A | 9/2000 | McEver et al. |
| 6,376,475 | B1 | 4/2002 | Marth |
| 6,455,678 | B1 | 9/2002 | Yin et al. |
| 6,586,192 | B1 | 7/2003 | Peschle et al. |
| 7,192,914 | B1 | 3/2007 | Marth et al. |
| 8,084,236 | B2 | 12/2011 | Sackstein |
| 8,728,810 | B2 | 8/2014 | Sackstein |
| 8,852,935 | B2* | 10/2014 | Sackstein ............. C12N 5/0006 435/372 |
| 2003/0040607 | A1 | 2/2003 | Sackstein |
| 2003/0216295 | A1* | 11/2003 | Fukuda ................. C07K 14/47 424/133.1 |

FOREIGN PATENT DOCUMENTS

| | | |
|---|---|---|
| WO | 9201049 | 1/1992 |
| WO | 9611012 | 4/1996 |

OTHER PUBLICATIONS

Attwood, Science 290:471-473 (2000).*
Skolnick et al., Trends in Biotech. 18: 34-39 (2000).*
Silva et al., Journal of Immunology 2017, 198: 1-12, published Mar. 31, 2017, doi:10.4049/jimmunol.1601636. (Year: 2017).*
Li et al., PNAS 77: 3211-3214, (1980). (Year: 1980).*
Wagers et al., J. Immunol 165: 5011-5016 (2000). (Year: 2000).*
Yamashita et al., The structures of the carbohydrate moieties of mouse kidney γ-glutamyltranspeptidase: Occurrence of X-antigenic determinants and bisecting N-acetylglucosamine residues, Arch. Biochem. Biophysics, 1985, 240(2):573-582.
Yednock et al., Phosphomannosyl-derivatized Beads Detect a Receptor Involved in Lymphocyte Homing, J. Cell Biol., 1987, 104(3):713-723.
Zannettino et al., Primitive human hematopoietic progenitors adhere to P-selectin (CD62P), Blood, 1995, 85(12):3466-3477.
Zhou et al., The Selectin GMP140 Binds to Sialylated, Fucosylated Lactosaminoglycans on Both Myeloid and Nonmyeloid Cells, J. Cell Biol., 1991, 115(2):557-564.
Zollner, et al., The E-selectin Ligand-1 is Selectively Activated in Chinese Hamster Ovary Cells by the α(1,3)- Fucosyltransferases IV and VII, J. Biol. Chem., 1996, 271(51):33002-33008.
Pouyani et al., PSGL-1 Recognition of P-Selectin is Controlled by a Tyrosine Sulfation Consensus at the PSGL-1 Amino Terminus, Cell, 1995, 83:333-343.
Puri et al., Sialomucin CD34 is the Major L-Selectin Ligand in Human Tonsil High Endothelial Venules, J. Cell. Biol., 1995, 131:261-270.
Ramakrishnan, Current status of antibody-toxin conjugates for tumor therapy, Targeted Diagn. Ther., 1990, 3:189-213.
Ramos et al., Functional Characterization of L-Selectin Ligands on Human Neutrophils and Leukemia Cell Lines: Evidence for Mucin-like Ligand Activity Distinct From P-Selectin Glycoprotein Ligand-1, Blood, 1998, 91(3): 1067-1075.
Rasmussen et al., Lymphocyte recognition of lymph node high endothelium. VII. Cell surface proteins involved in adhesion defined by monoclonal anti-HEBFLN (A.11) antibody, J. Immunol., 1985, 135(1):19-24.
Reinherz et al., Heterogeneity of human T4+ inducer T cells defined by a monoclonal antibody that delineates two functional subpopulations, J. Immunol., 1982, 128(1):463-468.

(Continued)

Primary Examiner — Phillip Gambel
(74) Attorney, Agent, or Firm — Bryan Cave Leighton Paisner LLP

(57) ABSTRACT

The invention feature methods and compositions for treating hematopoietic disorders, inflammatory conditions, and cancer and providing stem cell therapy in a mammal.

9 Claims, 22 Drawing Sheets

Specification includes a Sequence Listing.

(56) References Cited

OTHER PUBLICATIONS

Rosen et al., Involvement of sialic acid on endothelial cells in organ-specific lymphocyte recirculation, Science, 1985, 228(4702):1005-1007.
Rosen, Cell surface lectins in the immune system, Seminars in Immunology, 1993, 5(4):237-247.
Sackstein et al., A hematopoietic cell L-selectin ligand that is distinct from PSGL-I and displays N-glycan-dependent binding activity, Blood, 2000, 96(8):2765-2774.
Sackstein et al., Evidence of post-transcriptional regulation of L-selectin gene expression in rat lymphoid cells, Immunology, 1995, 85:198-204.
Sackstein et al., Lymphocyte Adhesion to Psoriatic Dermal Endothelium is Mediated by a Tissue-specific Receptor/Ligand Interaction, J. Invest. Dermatol., 1988, 91:423-428.
Sackstein et al., Physiologic migration of lymphocytes to lymph nodes following bone marrow transplantation: Role in immune recovery, Seminars in Oncology, 1993, 20(5):34-39, Suppl. 6.
Sackstein, Expression of an L-Selectin Ligand on Hematopoietic Progenitor Cells, Acta Haematologica, 1997, 97(1-2):22-28.
Sako et al., Expression cloning of a functional glycoprotein ligand for P-selectin, Cell, 1993, 75(6):1179-1186.
Sako et al., A Sulfated Peptide Segment at the Amino Terminus of PSGL-1 is Critical for P-Selectin Binding, Cell, 1995, 83:323-331.
Sasaki et al., Expression Cloning of a Novel Galβ(1-3/1-4)GlcNAc α2,3-Sialyltransferase Using Lectin Resistance Selection, J. Biol. Chem., 1993, 268(30):22782-22787.
Sassetti et al., Identification of Podocalyxin-like Protein as a High Endothelial Venule Ligand for L-selectin: Parallels to CD34, J. Exp. Med., 1998, 187(12):1965-1975.
Schweitzer et al., Constitutive expression of E-selectin and vascular cell adhesion molecule-1 on endothelial cells of hematopoietic tissues, Am. J. Pathol., 1996, 148(1):165-175.
Sharon et al., Carbohydrates in cell recognition, Scientific American, 1993, 268(1):82-89.
Shaw et al., Two antigen-independent adhesion pathways used by human cytotoxic T-cell clones, Letters to Nature, 1986, 323(6085):262-264.
Shimizu et al., Mucins in the mainstream, Nature, 1993, 366(6456):630-631.
Simmons et al., Potential Adhesion Mechanisms for Localisation of Haemopoietic Progenitors to Bone Marrow Stroma, Leuk. Lymph., 1994, 12:353-363.
Snapp et al., A Novel P-Selectin Glycoprotein Ligand-I Monoclonal Antibody Recognizes an Epitope Within the Tyrosine Sulfate Motif of Human PSGL-I and Blocks Recognition of Both P-and L-Selectin, Blood, 1998, 91(1): 154-164.
Spertini et al., Leukocyte adhesion molecule-1 (LAM-1, L-selectin) interacts with an inducible endothelial cell ligand to support leukocyte adhesion, J. Immunol., 1991, 147:2565-2573.
Spertini et al., P-Selectin Glycoprotein Ligand 1 is a Ligand for L-Selectin on Neutrophils, Monocytes, and CD34+ Hematopoietic Progenitor Cells, J. Cell Biol., 1996, 135(2):523-531.
Springer et al., The Lymphocyte Function Associated LFA-1, CD2, and LFA-3 Molecules: Cell Adhesion Receptors of the Immune System, Ann. Review Immunol., 1987, 5:223-252.
Stamper et al., Lymphocyte homing into lymph nodes: in vitro demonstration of the selective affinity of recirculating lymphocytes for high-endothelial venules, J. Exp. Med., 1976, 144(3):828-833.
Stoolman et al., Phosphomannosyl Receptors May Participate in the Adhesive Interaction between Lymphocytes and High Endothelial Venules, J. Cell Biol., 1988, 99(4):1535-1540.
Stoolman et al., Possible Role for Cell-surface Carbohydrate-binding Molecules in Lymphocyte Recirculation, J. Cell Biol., 1983(3):722-729.
Streeter et al., A tissue-specific endothelial cell molecule involved in lymphocyte homing, Nature, 1988, 331(6151):41-48.
Streeter et al., Immunohistologic and Functional Characterization of a Vascular Addressin Involved in Lymphocyte Homing into Peripheral Lymph Nodes, J. Cell Biol., 1988, 107(5):1853-1862.
Sutherland et al., Differential sensitivity of CD34 epitopes to cleavage by Pasturella haemolytica glycoprotease: implications for purification of CD34-positive progenitor cells, Exp. Hematol., 1992, 20:590-599.
Suzuki et al., Sulfated glycolipids are ligands for a lymphocyte homing receptor, L-selectin (LECAM-1), Binding epitope in sulfated sugar chain, Biochem. Biophys Res Commun, 1993, 190(2):426-434.
Tangermann et al., Sulfation of a High Endothelial Venule—expressed Ligand for L-Selectin: Effects on Tethering and Rolling of Lymphocytes, J. Exp. Med., 1999, 190(7):935-941.
Tarentino et al., Multiple Endoglycosidase F Activities Expressed by Flavobacterium meningosepticum Endoglycosidases F2 and F3, J. Biol. Chem., 1993, 268(13):9702-9708.
Tedder et al., Expression of the human leukocyte adhesion molecule, LAM1. Identity with the TQ1 and Leu-8 Differentiation antigens, J. Immunol., 1990, 144(2):532-540.
Terstappen et al., Flow cytometric assessment of human T-cell differentiation in thymus and bone marrow, Blood, 1992, 79(3):666-677.
Tracey et al., Characterization of the P-selectin ligand on human hematopoietic progenitors, Exp. Hematol., 1996, 24(13):1494-1500.
Trimble et al., Identification of Distinct Endoglycosidase (Endo) Activities in Flavobacterium meningosepticum: Endo F1, Endo F2, and Endo F3, J. Bio. Chem., 1991, 266(3):1646-1651.
True et al., Requirement for Sialic Acid on the Endothelial Ligand of a Lymphocyte Homing Receptor, J. Cell Biol., 1990, 111(6):2757.
Tu et al., L-Selectin Binds to P-Selectin Glycoprotein Ligand-Ion Leukocytes: Interactions Between the Lectin, Epidermal Growth Factor, and Consensus Repeat Domains of the Selectins Determine Ligand Binding Specificity, J. Immunol., 1996, 157(9):3995-4004.
Vachino et al., P-selectin Glycoprotein Ligand-1 is the Major Counter-receptor for P-selectin on Stimulated T Cells and is Widely Distributed in Non-functional Form on Many Lymphocytic Cells, J. Biol. Chem., 1995, 270(37):21966-21974.
Varki, Selectin ligands, PNAS, 1994, 91:7390-7397.
Verfaillie, Adhesion Receptors as Regulators of the Hematopoietic Process, Blood, 1998, 92(8):2609-2612.
Walcheck et al., Neutrophil-neutrophil interactions under hydrodynamic shear stress involve L-selectin and PSGL-1. A mechanism that amplifies initial leukocyte accumulation of P-selectin in vitro, J. Clin. Invest., 1996, 98(5):1081-1087.
Watanabe et al., Cell adhesion molecule expression of CD34+ cells in grafts and time to myeloid and platlet recovery after autologous stem cell transplations, Exp. Hematol., 1998, 26:10-18.
Watson et al., A Homing Receptor-IgG Chimera as a Probe for Adhesive Ligands of Lymph Node High Endothelial Venules, J. Cell Biol., 1990, 110(6):2221-2229.
Wilson et al., Evidence that leukosialin, CD43, is intensely sulfated in the murine T lymphoma line RDM-4, J. Immunol., 1992, 148(6):1777-1783.
Woodruff et al., Specific cell-adhesion mechanisms determining migration pathways of recirculating lymphocytes, Ann. Rev. Immunol., 1987, 5:201-222.
Yamashita et al., Organ-specific difference in the sugar chains of γ-glutamyltranspeptidase, Arch. Biochem. Biophysics, 1983, 225(2):993-996.
Borges et al., The cutaneous lymchocyte antigen is a skin lymphocyte homing receptor for the vascular lectin endothelial cell-leukocyte adhesion molecule 1, J. Biol. Chern., 1997, 272(45):28786-28792.
Candal et al., BMEC-I: A Human Bone Marrow Microvascular endothelial Cell Line with Primary Cell Characteristics, Microvasc. Research, 1996, 52:221-234.
Carlos et al., Leukocyte-endothelial adhesion molecules, Blood, 1994, 84(7):2068-2101.
Shin et al., Lymphocyte homing receptors and preferential migration pathways, Proc. Soc. Exp. Biol. and Med., 1991, 196:374-380.
Civin et al., Antigenic analysis of hematopoiesis. III. A hematopoietic progenitor cell surface antigen defined by a monoclonal antibody raised against KG-1a cells, J. Immunology, 1984, 133(1):157-165.

(56) References Cited

OTHER PUBLICATIONS

Gowans et al., The Route of re-ciricluation of lymphocytes in the rat. Proc R Soc Lond B Biol Sci., 1964, 159:257-282.

Green et al., Further studies of the binding specificity of the leukocyte adhesion molecule, L-selectin, towards sulphated oligosaccharides—suggestion of a link between the selectin- and the integrin-mediated lymphocyte adhesion systems, Glycobiology. 1995, 5(1):29-38.

Green et al., High affinity binding of the leucocyte adhesion molecule L-selectin to 3' sulphated-Lea and -Lex oligosaccharides and the predominance of sulphate in this interaction demonstrated by binding studies with a series of lipid-linked oligosaccharides, Biochemical and Biophysical Research Communications, 1992, 188(1):244-251.

Greenberg et al., Relationship between selectin-mediated rolling of hematopoietic stem and progenitor cells and progression in hematopoietic development, Blood, 2000, 95(2):478-486.

Griffin et al., Granulocyte-macrophage colony-stimulating factor and other cytokines regulate surface expression of the leukocyte adhesion molecule-1 on human neutrophils, monocytes, and their precursors, J. Immunology, 1990, 145(2):576-584.

Gunji et al., Expression and Function of Adhesion Molecules on Human Hematopoietic Stem Cells: CD34+ LFA-1-Cells Are More Primitive Than CD34+ LFA-I+ Cells, Blood, 1992, 80(2):429-436.

Guyer et al., P-Selectin Glycoprotein Ligand-I (PSGL-I) is a Ligand for L-Selectin in Neutrophil Aggregation, Blood, 1996, 88(7):2415-2421.

Hale et al., Bromelain Treatment of Human T Cells Removes CD44, CD45RA, E2IMIC2, CD6, CD7, CD8, and Leu 8/LAMI Surface Molecules and Markedly Enhances CD2-Mediated T Cell Activation, J. Immunol., 1992, 149(12):3809-3816.

Hemmerich et al., 6-sulfated sialyl Lewis x is a major capping group of GlyCAM-1, Biochemistry, 1994, 33(16):4830-4835.

Hemmerich et al., Sulfation-dependent recognition of high endothelial venules (HEV)-ligands by L-selectin and MECA 79, and adhesion-blocking monoclonal antibody, J. Exp. Med., 1994, 180(6):2219-2226.

Huff et al., Presence of an antigenic determinant common to rat IgE-potentiating factor, IgE-suppressive factor, and Fc epsilon receptors on T and B lymphocytes, J. Immunol., 1983, 131(3):1090-1095.

Imai et al., Identification of a carbohydrate-based endothelial ligand for a lymphocyte homing receptor, J. Cell Biol. 1991, 113(5):1213-1221.

Imai et al., Sulphation requirement for GlyCAM-1, an endothelial ligand for L-selectin, Nature, 1993, 361(6412):555-557.

Jalkanen et al., A lymphoid cell surface glycoprotein involved in endothelial cell recognition and lymphocyte homing in man, Eur. J. Immunol., 1986, 16:1195-1202.

Jalkanen et al., Biochemical Properties of Glycoproteins Involved in Lymphocyte Recognition of High Endothelial Venules in Man, J. Immunol., 1988, 141(5): 1615-1623.

Jung et al., Rapid modulation of homing receptors (gp90MEL-14) induced by activators of protein kinase C. Receptor shedding due to accelerated proteolytic cleavage at the cell surface, J Immunol, 1990, 144(8):3130-3136.

Kansas, Selectins and Their Ligands: Current Concepts and Controversies, Blood, 1996, 88(9):3259-3287.

Kikuta et al., Localization of ligands for L-selectin in mouse peripheral lymph node high endothelial cells by colloidal gold conjugates, Blood, 1994, 84(11):3766-3775.

Kishimoto et al., Identification of a human peripheral lymph node homing receptor: A rapidly down-regulated adhesion molecule, PNAS, 1990, 87(6):2244-2248.

Kobayashi et al., Expression of adhesion molecules on human hematopoietic progenitor cells at different maturational stages, Stem Cells, 1994, 12(3):316-321.

Koeffler et al., An undifferentiated variant derived from the human acute myelogenous leukemia cell line (KG-1), Blood, 1980, 56:265-273.

Koenig et al., L-selectin expression enhances clonogenesis of CD34+ cord blood progenitors, Pediatr Res, 1999, 45:867-870.

Kugleman et al., The Core Protein of Epican, a Heparan Sulfate Proteoglycan on Keratinocytes, is an Alternative Form of CD44, The Society for Investigative Dermatology, Inc., 1992: 887-891.

Kumar et al., Core2 beta-1,6-N-acetylglucosaminyltransferase enzyme activity iscritical for P-selectin glycoprotein ligand-1 binding to P-selectin, Blood, 1996, 88(10):3872-3879.

Lasky et al., An endothelial ligand for L-Selectin is a novel mucin-like molecule, Cell, 1992, 69(6):927-938.

Laszik et al., P-Selectin Glycoprotein Ligand-I is Broadly Expressed in Cells of Myeloid, Lymphoid, and Dendritic Lineage and in Some Nonhematopoietic Cells, Blood, 1996, 88(8):3010-3012.

Lawrence et al., Threshold Levels of Fluid Shear Promote Leukocyte Adhesion through Selectins (CD62L,P,E), J. Cell Biol., 1999, 36(3):717-727.

Lawrence et al., Effect of Flow on Polymorphonuclear LeukocytelEndothelial Cell Adhesion, Blood, 1987, 70(5):1284-1290.

Lemonnier et al., The induction of cytolytic T lymphocytes with purified plasma membranes, J Immunol, 1978, 120(4):1114-1120.

Levesque et al., PSGL-1-Mediated Adhesion of Human Hematopoietic Progenitors to P-Selectin Results in Suppression of Hematopoiesis, Immunity, 199, 11:369-378.

Lewinson et al., Leukocyte-endothelial cell recognition: Evidence of a common molecular mechanism shared by neutrophils, lymphocytes, and other leukocytes, J. Immunol., 1987, 138:4313-4321.

Li et al., Post-translational Modifications of Recombinant P-selectin Glycoprotein Ligand-1 Required for Binding to P-and E-selectin, The Journal of Biological Chemistry, 1996, 271:3255-3264.

Majdic et al., Signaling and Induction of Enhanced Cytoadhesiveness Via the Hematopoietic Progenitor Cell Surface Molecule CD34, Blood, 1994, 83(5):1226-1234.

Maley et al., Characterization of glycoproteins and their associated oligosaccharides through the use of endoglycosidases, Analytical Biochemistry, 1989, 180(2):195-204.

Maly et al., The alpha(1,3)fucosyltransferase Fuc-TVII controls leukocyte trafficking through an essential role in L-, E-, and P-selectin ligand biosynthesis, 86(4):643-653.

Marchesi et al., The migration of lymphocytes through the endothelium of venules in lymph nodes: an electron microscope study, Proc R Soc Land B Biol Sci., 1963, 159:283-290.

Mazo et al., Hematopoietic Progenitor Cell Rolling in Bone Marrow Microvessels: Parallel Contributions by Endothelial Selectins and Vascular Cell Adhesion Molecule 1, J. Exp. Med., 1998, 188(3):465-474.

Moore et al., Structure and Function of P-Selectin Glycoprotein Ligand-1, Leuk. Lymph. 1998, 29:1-5.

Vioore et al., P-Selectin Glycoprotein Ligand-1 Mediates Rolling of Human Neutrophils on P-Selectin, J. Cell Biol., 1992, 118(4):445-456.

Nielemla et al., Complementary Acceptor and Site Specificities of Fuc-TIV and Fuc-TVII Allow Effective Biosynthesis of Sialyl-TriLex and Related Polylactosamines Present on Glycoprotein Counterreceptors of Selectins, J. Biol. Chem., 1998, 273:4021-4026.

Niorgard et al., Characterization of a Specific Ligand for P-selectin on Myeloid Cells, J. Bio. Chem., 1993, 268 (17):12764-12774.

Ord et al., Structure of the gene encoding the human leukocyte adhesion molecule-1 (TQ1, Leu-8) of lymphocytes and neutrophils, J. Bio. Chem., 1990, 265(14):7760-7767.

Oxley et al., L-Selectin-CD34 Interactions Mediate Functional Binding of Lymphocytes to Hematopoietic Progenitor Cells, Clinical Research, 1994, 42(2):235A.

Oxley et al., Detection of an L-Selectin Ligand on a Hematopoietic Progenitor Cell Line, Blood, 1994, 84(10):3299-3306.

Paulson et al., Newcastle Disease Virus Containsa Linkage-specific Glycoprotein Sialidase, J. Bio. Chem., 1982, 257(21):12734-12738.

Moore et al., P-Selectin Glycoprotein Ligand-1 Mediates Rolling of Human Neutrophils on P-Selectin, J. Cell Biol., 1995, 128(4):661-671.

(56) References Cited

OTHER PUBLICATIONS

Clarke et al., Independent regulation of Fuc-TIV and Fuc-TVII genes leading to modulation of cell surface antigen expression in developing myeloid cells, Glycobiology, 1997, 7(6):835-846.
Skolnick et al, From genes to protein structure and function: novel applications of computational approaches in the genomic era, Trends in Biotechnology, 2000, 18;34-39.
Maiti et al., TNF-alpha induction of CD44-mediated leukocyte adhesion by sulfation, Science, 1998, 282:941-943.
Katoh et al., Culling edge: an inducible sialidase regulates the hyaluronic acid binding ability of CD44-bearing human monocytes, J Immunol. 1999,162:5058-5061.
Katoh et al., Glycosylation of CD44 negatively regulates its recognition of hyaluronan, J Exp Med, 1995, 182(2):419-429.
Berg et al., The cutaneous lymphocyte antigen is a skin lymphocyte homing receptor for the vascular lectin endothelial cell-leukocyte adhesion molecule 1, J. Exp Med., 1991, 174:1461-1466.
Picker et al., A unique phenotype of skin-associated lymphocyte in humans, Am. J. Pathology, 1990, 136: 10 53-1068.
Jutila et al., Cell surface P- and E-selectin support shear-dependent rolling of bovine gamma/delta T cells, J Immunol., 1994,153:3917-3928.
Walcheck et al., Bovine gamma/delta T cells bind E-selectin via a novel glycoprotein receptor: first characterization of a lymphocyte/E-selectin interaction in an animal model, J. Exp. Med., 1993 178(3):853-863.
Dimitroff et al., CD44 is a Major E-Selectin Ligand on Human Hematopoietic Progenitor Cells, The Journal of Cell Biology, 2001, 153:1277-1286.
Dimitroff et al., Differential L-Selectin Binding Activities of Human Hematopoietic Cell L-Selectin Ligands, HCELL and PSGL-I, J. Biol. Chem., 2001, 276(50):47623-47631.
Ngo et al., In the Protein Folding Problem and Tertiary Structure Prediction, Merz et al (Eds.), 1994, Birkhauser, Boston, MA, 433, 492-495.
Sackstein et al., A hematopoietic cell L-selectin ligand exhibits sulfate-independent binding activity., Blood, 1997, 89:2773-2781.
Sackstein, The Bone Marrow is Akin to Skin: HCELL and the Biology of Hematopoietic Stem Cell Homing, J. Invest Dermatol., 2004, 122: 1061-1069.
Bollman et al., Techniques for the collection of lymph from the liver, small intestine, or thoracic duct of the rat, Journal of Laboratory and Clinical Medicine, 1948, 33(10):1349-1352.
Stamenkovic et al., The hematopoietic and epithelial forms of CD44 are distinct polypeptides with different adhesion potentials for hyaluronate-bearing cells, The EMBO Journal, 1991, 10(2):343-348.
Arbones et al., Lymphocyte homing and leukocyte rolling and migration are impaired in L-selectin-deficient mice, Immunity, 1994, 1(4):247-260.
Arruffo et al., CD62/P-selectin recognition of myeloid and tumor cell sulfatides. Cell, 1991, 67(1):35-44.
Asa et al., The P-selectin glycoprotein ligand functions as a common human leukocyte ligand for P-and E-selectins, J. Biol. Chem., 1995, 270:11662-11670.
Baeuerle et al., Chlorate—a potent inhibitor of protein sulfation in intact cells, Biochem. and Biophys. Res. Comm., 1986, 141(2):870-877.
Baumhueter et al., Binding of L-selectin to the vascular sialomucin CD34, Science, 1993, 262(5132):436-438.
Berg et al., L-selectin-mediated lymphocyte rolling on MAdCAM-1, Nature, 1993, 366(6456):695-698.
Bertozzi, Cracking the carbohydrate code for selectin recognition, Chemistry & Biology, 1995, 2:703-708.
Bevilacqua et al., Selectins, J. Clin. Investigation, 1993, 91(2):379-387.
Bistrup et al., Sulfotransferases of two specificities function in the reconstitution of high endothelial cell ligands for L-selectin, J. Cell Biol., 1999, 145:899-910.

Placic et al., Chemoenzymatic synthesis of dendritic sialyl LewisX, Carbohydrate Research, 1998, 305, 403-442.
Ernst et al., Substrate and donor specificity of glycosyl transferases, Glycoconjugate Journal, 1999, 16, 161-170.
Srivastava et al., Enzymatic transfer of a preassembled trisaccharide antigen to cell surfaces using a fucosyltransferase, J. Biological Chemistry, 1992, 267(31), 22356-22361.
Mahal et al., Engineered cell surfaces: fertile ground for molecular landscaping, Chemistry and Biology, 1997, 4, 115-422.
Tsuboi et al., Acquisition of P-selectin binding activity by en Bloc transfer of Sulfo LeX trisaccharide to the cell surface:Comparison to a Sialyl LeX Tetrasaccharide transferred on the cell surface, Arch of Biochem and Biophy, 2000, 374(1), 100-106.
Kelm et al., Reconstruction of the masking effect of sialic acid groups on sialidase-treated erythrocytes by the action of sialyltransferases, Carbohydrate Research, 1986, 149, 59-64.
Goelz et al., Differential Expression of an E-selectin Ligand (SleX) by Two Chinese Hamster Ovary Cell Lines Transfected with the Same a(1,3)-Fucosyltransferase Gene (ELFT), 1 Biological Chem., 1994, 269(2):1033-1040.
Goebeler et al., Migration of highly aggressive melanoma cells on hyaluronic acid is associated with functional changes, increased turnover and shedding of CD44 receptors, J. Cell Science, 1996, 109:1957-1964.
Girard et al., High endothelial venules (HEVs): specialized endothelium for lymphocyte migration, Immunol. Today, 1995, 16(9):449-457.
Gatenby et al., Dissection of immunoregulatory subpopulations of T lymphocytes within the helper and suppressor sublineages in man, 1982, J. Immunology, 129(5):1997-2000.
Gallatin et al., A cell-surface molecule involved in organ-specific homing of lymphocytes, Nature, 1983, 304(5921):30-32.
Fuhlbrigge et al., Cutaneous lymphocyte antigen is a specialized form of PSGL-I expressed on skin-homing T cells, Nature, 1997, 389:978-981.
Frenette et al., Endothelial selectins and vascular cell adhesion molecule-1 promote hematopoietic progenitor homing to bone marrow, PNAS, 1998, 95:14423-14428.
Frenette et al., Susceptibility to Infection and Altered Hematopoiesis in Mice Deficient in Both P- and E-Selectins, Cell, 1996, 84(4):563-574.
Francis et al., Two new pseudopod morphologies displayed by the human hematopoietic KG1a progenitor cell line and by primary human CD34(+) cells, Blood, 1998, 92(10):3616-3623.
Finger et al., Adhesion through L-selectin requires a threshold hydrodynamic shear, Nature, 1996, 379:266-269.
Drzeniek, Substrate specificity of neuraminidases, Histochem. J., 1973, 5:271-90.
Dowbenko et al., Glycosylation-dependent Cell Adhesion Molecule 1 (GlyCAM 1) Mucin is Expressed by Lactating Mammary Gland Epithelial Cells and is Present in Milk, J. Clin. Invest., 1993, 92(2):952-960.
Dougherty et al., Molecular Cloning of CD44RI and CD44R2, Two Novel Isoforms of the Human CD44 Lymphocyte Homing' Receptor Expressed by Hemopoietic Cells, J. Exp. Med., 1991, 174:1-5.
Dimitroff et al., A distinct glycoform of CD44 is an L-selectin ligand on human hematopoietic cells, PNAS, 2000, 97(25):13841-13846.
Delucca et al., A Novel Cobra Venom Metalloproteinase, Mocarhagin, Cleaves a 10-Amino Acid Peptide from the Mature N Terminus of P-selectin Glycoprotein Ligand Receptor, PSGL-I, and Abolishes P-selectin Binding, J. Biological Chem., 1995, 270(45):26734-26737.
Current Protocols in Molecular Biology, v. 2, 1998, John Wiley & Sons, Inc., pp. 9.2.1-9.2.10.
Cullen et al., Differential glycosylation of murine B cell and spleen adherent cell la antigens, Journal of Immunology, 1981, 127(4):1478-1484.
Cowing et al., T cells discriminate between la antigens expressed on allogeneic accessory cells and B cells: A potential function for carbohydrate side chains on la molecules, PNAS, 1983, 80(19):6000-6004.

* cited by examiner

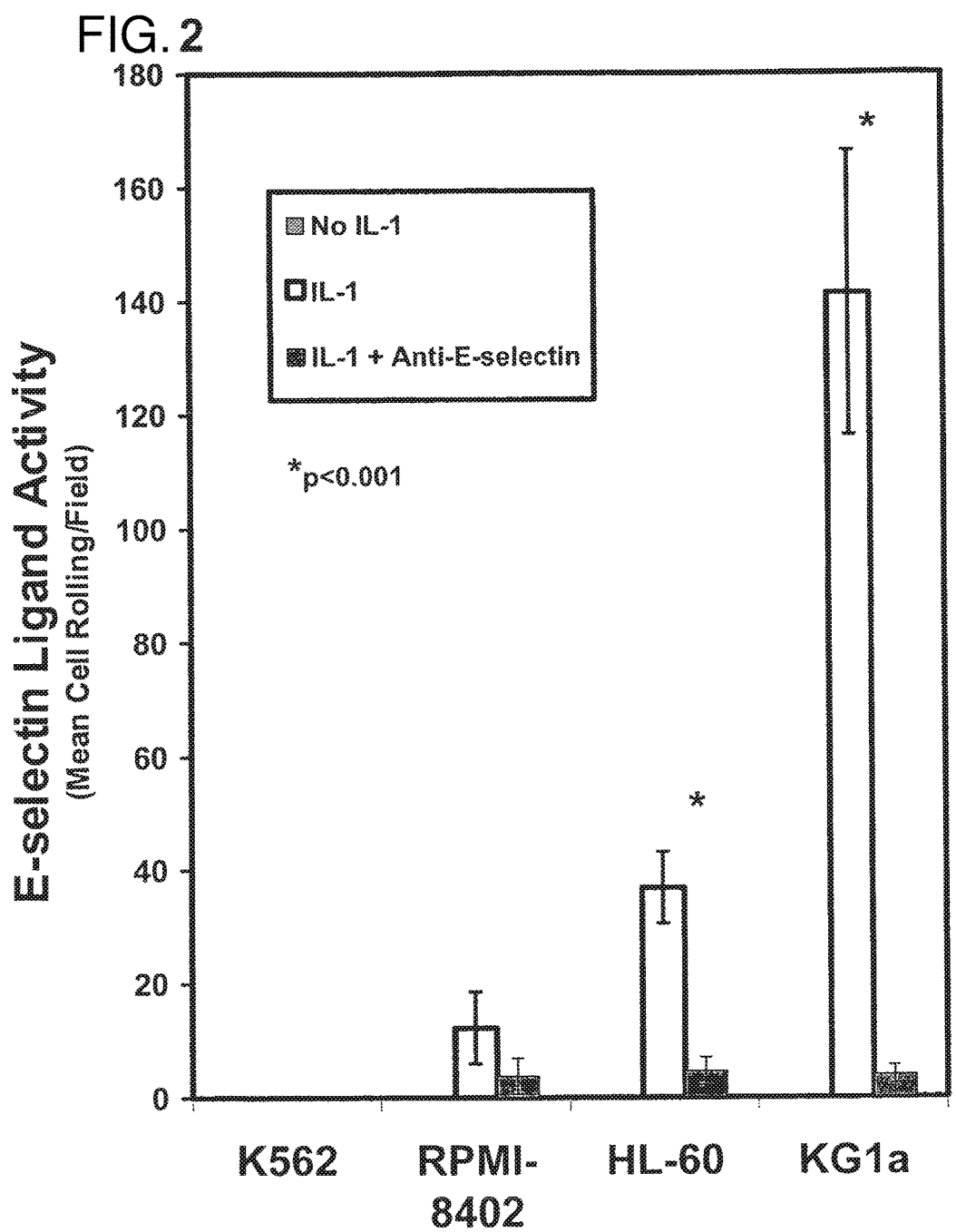

E-selectin Ligand Activity
(Mean±S.D. CHO-E Cell Rolling on 100kDa Band)

FIG. 4A. Hermes-1 Immunoblot
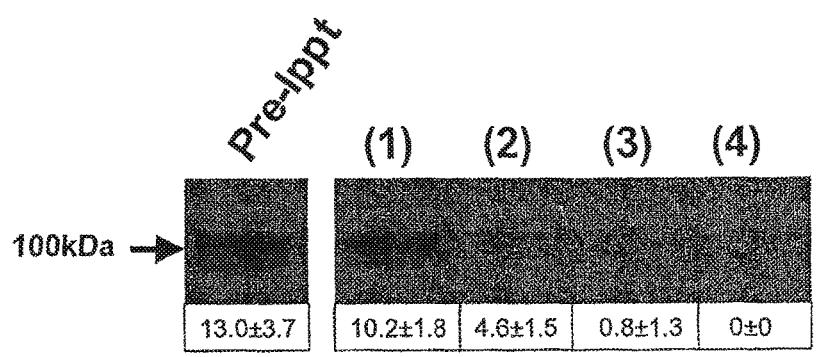
E-selectin Ligand Activity
(Mean±S.D. CHO-E Cell Rolling on 100kDa Band)
FIG. 4B. HECA-452 Immunoblot
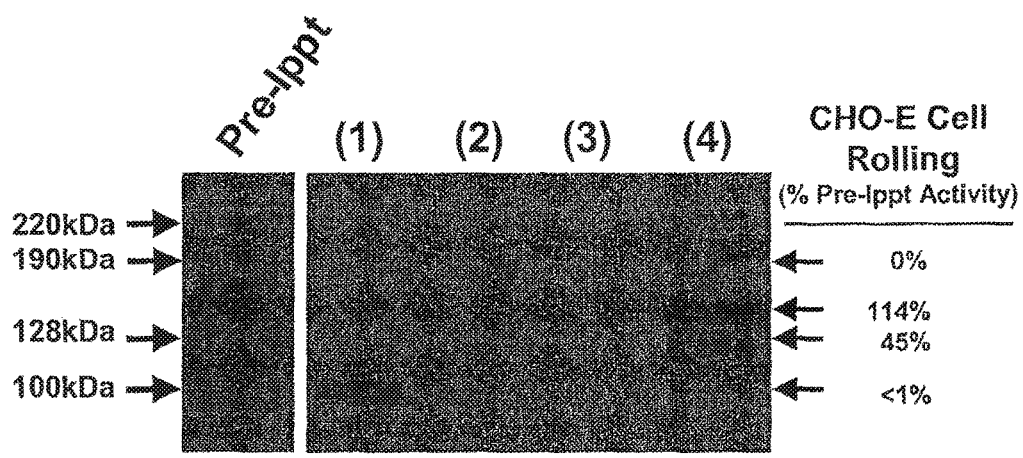

E-selectin Ligand Activity
(Mean±S.D. CHO-E Cell Rolling on 100kDa Band)

E-selectin Ligand Activity
(Mean±S.D. CHO-E Cell Rolling on 100kDa Band)

E-selectin Ligand Activity
(Mean±S.D. CHO-E Cell Rolling on 100kDa Band)

FIG. 12A
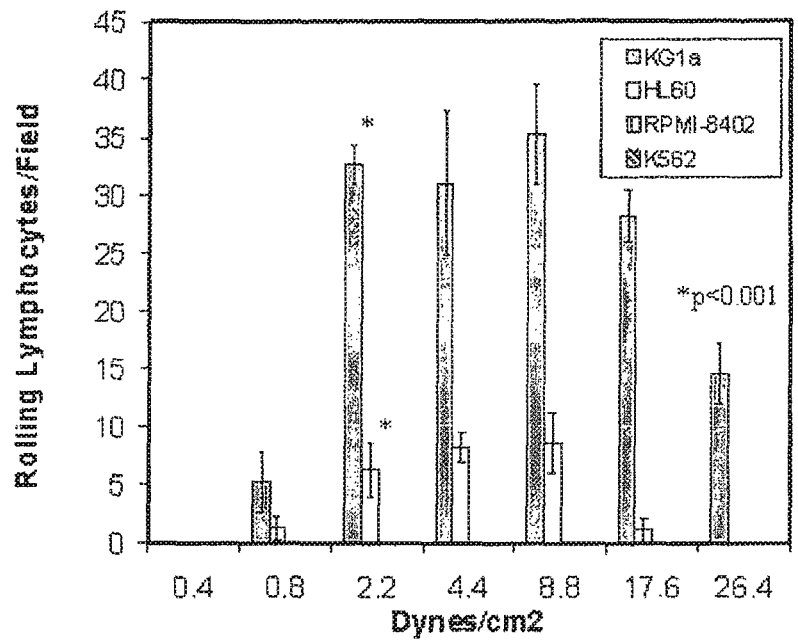
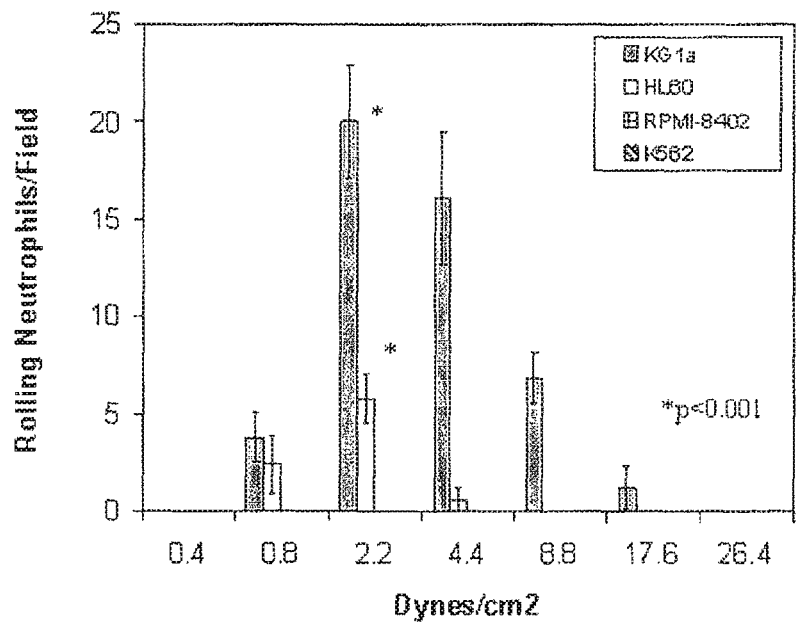
FIG. 12B

FIG. 13A
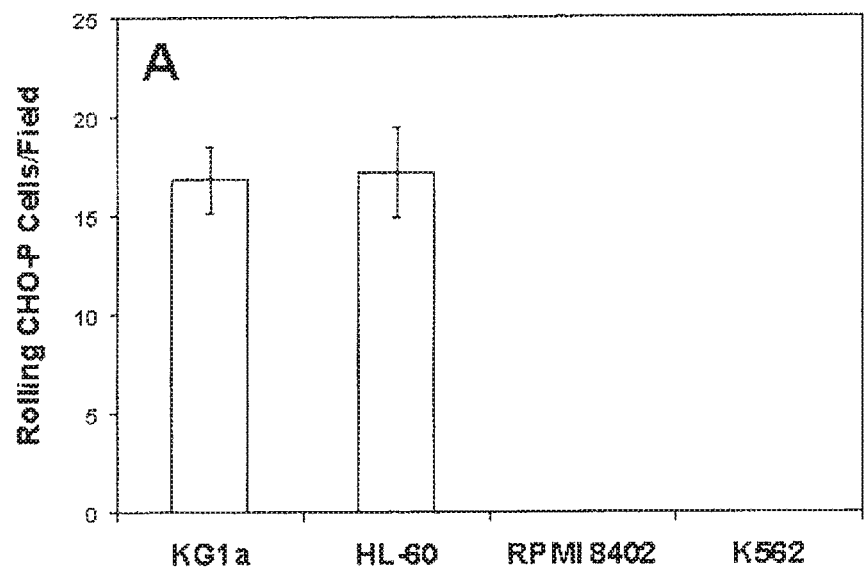
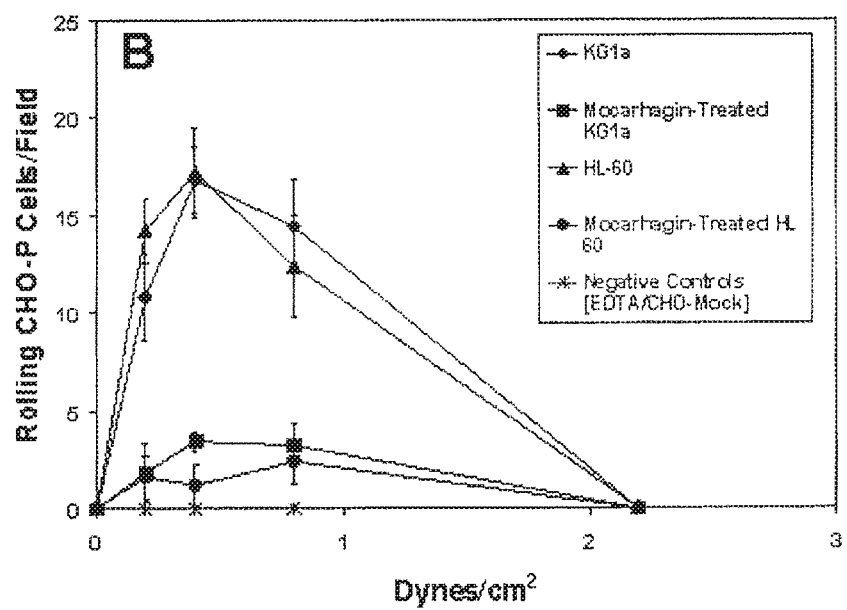
FIG. 13B

FIG. 14A. Autoradiography of Hermes-1 (CD44) and PL-2 (PSGL-1) Immunoprecipitates from [35S]-Labeled KG1a Cell Lysate

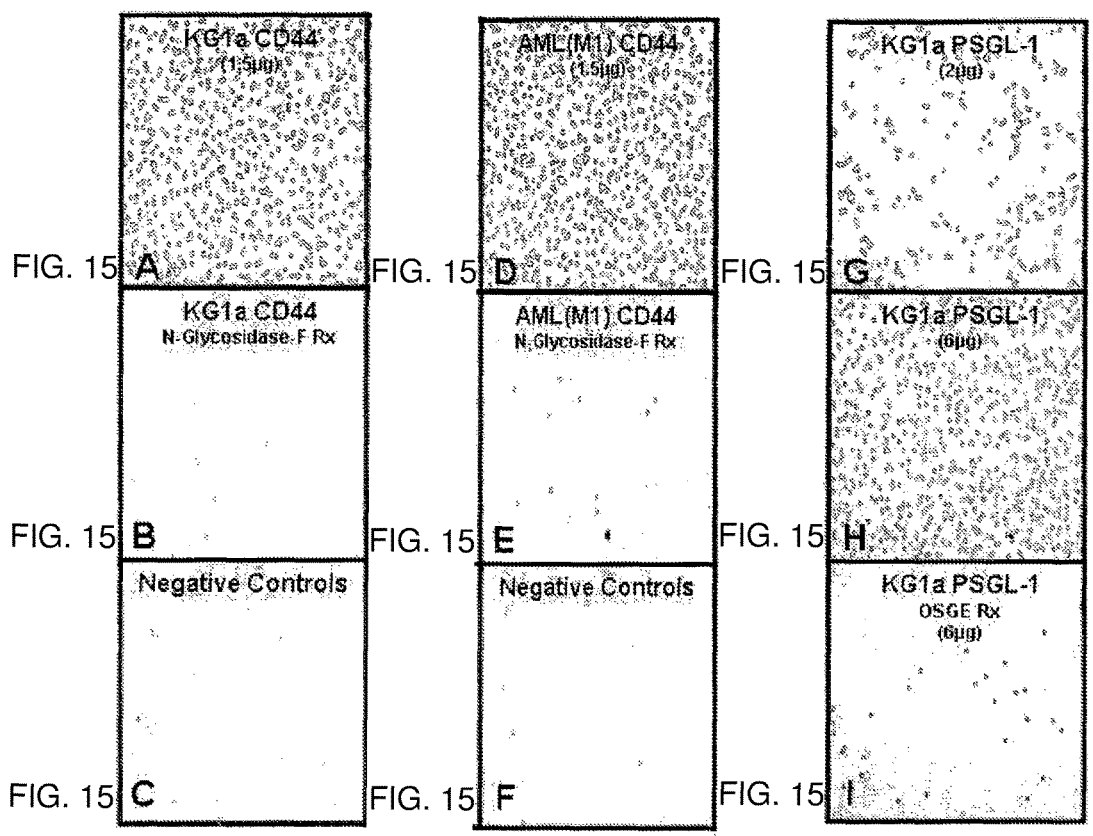

SEQUENCE LISTING

<160> NUMBER OF SEQ ID NOS: 1

<210> SEQ ID NO 1
<211> LENGTH: 493
<212> TYPE: PRT
<213> ORGANISM: Homo sapiens

<400> SEQUENCE: 1

Met Asp Lys Phe Trp Trp His Ala Ala Trp Gly Leu Cys Leu Val Pro
1               5                   10                  15

-continued

```
Leu Ser Leu Ala Gln Ile Asp Leu Asn Ile Thr Cys Arg Phe Ala Gly
         20                  25                  30
Val Phe His Val Glu Lys Asn Gly Arg Tyr Ser Ile Ser Arg Thr Glu
         35                  40                  45
Ala Ala Asp Leu Cys Lys Ala Phe Asn Ser Thr Leu Pro Thr Met Ala
50                  55                  60
Gln Met Glu Lys Ala Leu Ser Ile Gly Phe Glu Thr Cys Arg Tyr Gly
65                  70                  75                  80
Phe Ile Glu Gly His Val Val Ile Pro Arg Ile His Pro Asn Ser Ile
                 85                  90                  95
Cys Ala Ala Asn Asn Thr Gly Val Tyr Ile Leu Thr Ser Asn Thr Ser
                100                 105                 110
Gln Tyr Asp Thr Tyr Cys Phe Asn Ala Ser Ala Pro Pro Glu Glu Asp
             115                 120                 125
Cys Thr Ser Val Thr Asp Leu Pro Asn Ala Phe Asp Gly Pro Ile Thr
130                 135                 140
Ile Thr Ile Val Asn Arg Asp Gly Thr Arg Tyr Val Gln Lys Gly Glu
145                 150                 155                 160
Tyr Arg Thr Asn Pro Glu Asp Ile Tyr Pro Ser Asn Pro Thr Asp Asp
                 165                 170                 175
Asp Val Ser Ser Gly Ser Ser Ser Glu Arg Ser Ser Thr Ser Gly Gly
             180                 185                 190
Tyr Ile Phe Tyr Thr Phe Ser Thr Val His Pro Ile Pro Asp Glu Asp
             195                 200                 205
Ser Pro Trp Ile Thr Asp Ser Thr Asp Arg Ile Pro Ala Thr Asn Met
210                 215                 220
Asp Ser Ser His Ser Thr Thr Leu Gln Pro Thr Ala Asn Pro Asn Thr
225                 230                 235                 240
Gly Leu Val Glu Asp Leu Asp Arg Thr Gly Pro Leu Ser Met Thr Thr
                 245                 250                 255
Gln Gln Ser Asn Ser Gln Ser Phe Ser Thr Ser His Glu Gly Leu Glu
             260                 265                 270
Glu Asp Lys Asp His Pro Thr Thr Ser Thr Leu Thr Ser Ser Asn Arg
             275                 280                 285
Asn Asp Val Thr Gly Gly Arg Arg Asp Pro Asn His Ser Glu Gly Ser
290                 295                 300
Thr Thr Leu Leu Glu Gly Tyr Thr Ser His Tyr Pro His Thr Lys Glu
305                 310                 315                 320
Ser Arg Thr Phe Ile Pro Val Thr Ser Ala Lys Thr Gly Ser Phe Gly
                 325                 330                 335
Val Thr Ala Val Thr Val Gly Asp Ser Asn Ser Asn Val Asn Arg Ser
             340                 345                 350
Leu Ser Gly Asp Gln Asp Thr Phe His Pro Ser Gly Gly Ser His Thr
             355                 360                 365
Thr His Gly Ser Glu Ser Asp Gly His Ser His Gly Ser Gln Glu Gly
370                 375                 380
Gly Ala Asn Thr Thr Ser Gly Pro Ile Arg Thr Pro Gln Ile Pro Glu
385                 390                 395                 400
Trp Leu Ile Ile Leu Ala Ser Leu Leu Ala Leu Ala Leu Ile Leu Ala
                 405                 410                 415
Val Cys Ile Ala Val Asn Ser Arg Arg Arg Cys Gly Gln Lys Lys Lys
             420                 425                 430
Leu Val Ile Asn Ser Gly Asn Gly Ala Val Glu Asp Arg Lys Pro Ser
```

```
                435                 440                 445
Gly Leu Asn Gly Glu Ala Ser Lys Ser Gln Glu Met Val His Leu Val
    450                 455                 460

Asn Lys Glu Ser Ser Glu Thr Pro Asp Gln Phe Met Thr Ala Asp Glu
465                 470                 475                 480

Thr Arg Asn Leu Gln Asn Val Asp Met Lys Ile Gly Val
                485                 490
```

HEMATOPOIETIC PROGENITOR CELL POPULATIONS HAVING AFFINITY FOR E-SELECTIN / L-SELECTIN

RELATED APPLICATIONS

This application is a continuation of U.S. application Ser. No. 13/529,530, filed Jun. 21, 2012, which is a continuation of U.S. application Ser. No. 13/012,367, filed Jan. 24, 2011, which is a continuation of U.S. application Ser. No. 10/042,421, filed Oct. 18, 2001 and issued as U.S. Pat. No. 7,875,585 on Jan. 25, 2011, which claims the benefit of priority of U.S. Provisional Application No. 60/297,474, filed Jun. 11, 2001, and claims the benefit of priority of U.S. Provisional Application No. 60/240,987, filed Oct. 18, 2000. The contents of each of the prior applications are hereby incorporated by reference in their entirety for all purposes.

STATEMENT AS TO FEDERALLY SPONSORED RESEARCH

This invention was made with U.S. government support under National Institutes of Health grants NHLBI RO1 HL60528 and CA84156. The government has certain rights in the invention.

FIELD OF THE INVENTION

The invention provides compositions and methods for identifying stem cells and treating hematopoietic disorders, (e.g., leukemia), cancer, inflammatory disorders and disorders amenable for treatment with stem cells, (e.g., myocardial infarction, Parkinson's disease, diabetes, or stroke).

BACKGROUND OF THE INVENTION

The specialized cytoarchitecture of the hematopoietic microenvironment is created by discrete cell-cell and cell-matrix adhesive interactions that are tightly regulated by lineage-specific expression of adhesion molecules. The earliest human hematopoietic progenitor cells (HPCs) are characterized by the absence of lineage-specific markers and expression of the cell surface molecule, CD34. A variety of adhesion molecules are expressed on HPCs, including CD44 (the "hyaluronic acid receptor", also known as H-CAM), members of the integrin (e.g., LFA-1, VLA-4) and immunoglobulin (e.g., ICAM1) superfamilies, and a member of the selectin family, L-selectin. L-selectin (CD62L) is a calcium-dependent, carbohydrate binding protein in a family of adhesion molecules that also includes E-selectin (CD62E), expressed on activated vascular endothelium, and P-selectin (CD62P), found on both activated platelets and endothelial cells. Selectin-mediated interactions are critical not only for the rapid and efficient recruitment of leukocytes at a site of injury, but for steady state, tissue-specific homing as illustrated in: (1) lymphocyte homing to peripheral lymph nodes, (2) cutaneous tropism of human skin-homing T-cells and (3) hematopoietic progenitor cell (HPC) entry into bone marrow.

SUMMARY OF THE INVENTION

The invention features a novel glycosylated polypeptide expressed on normal human hemopoietic progentitor cells and on leukemic blasts designated hematopoietic cell E-selection/L-selectin ligand (HCELL). The HCELL polypeptides are also referred to herein as "KG1a CD44". HCELL is a novel glycoform of CD44 containing HECA-452 reactive sialyated, fucosylated N-glycans. The HCELL polypeptide is a ligand for both L-selectin and E-selectin.

The invention also features a method of identifying stem cells by contacting a test cell population with one or more agents that specifically bind to HCELL under conditions sufficient to form a complex between the agent and stem cell. The complex is detected and if present indicates the cell is a stem cell. Suitable agents include an anti-CD44 antibody, or an antibody with the binding specificity of monoclonal antibody HECA-452.

A stem cell is also identified by providing a selectin polypeptide, e.g., E-selectin or L-selectine immobilized on a solid phase and contacting the solid phase with a fluid sample containing a suspension of test cells. The solid phase is contacted with the fluid sample shear stress is achieved at the surface of the solid phase. By observing which cells that adhere to the solid phase a stem cell is identified. The test cell can be, for example, blood or bone marrow.

Also provided by the invention are various methods of isolating a stem cell (e.g., a pluripotent stem cell) from a population of cells. A stem cell is isolated by contacting a cell population with one or more agents that specifically bind to a HCELL polypeptide under conditions sufficient to form a complex between the agents and a stem cell. Complex formation is detected and removed from the cell population thereby isolating the stem cell from the cell population. Additionally, the stem cell/agent complex is disrupted.

Alternatively, a stem cell is isolated by providing a selectin polypeptide, e.g., E-selectin or L-selection immobilized on a solid phase and contacting the solid phase with a fluid sample containing a suspension of cells. The solid phase is contacted with the fluid sample so that shear stress is achieved at the surface of the solid phase. Stem cells are isolated by recovering the cells that adhere to the solid phase.

The invention also features methods of treating a hematopoietic disorders, cancer and disorders amenable to treatment with stem cells (i.e., stem cell therapy) in a mammal, by comprising administering to the mammal a composition comprising the cells isolated according to the methods described above.

The invention also provides a method of increasing the affinity of a cell for E-selectin and/or L-selectin, by providing a cell and contacting the cell with one or more agents that increases cell-surface expression or activity a HCELL polypeptide, thereby increasing affinity of the cell for E-selectin and/or L-selectin. Suitable agents include for example, a nucleic acid that encodes a CD44, glycosyltransferase or a glycosidase polypeptide.

The invention features methods of increasing the engraftment potential of a stem cell, by providing a stem cell a and contacting the stem cell with one or more agents that increases cell-surface expression or activity a HCELL polypeptide on the cell, thereby increasing the engraftment potential of stem cell.

Alternatively, the engraftment potential of a cell population is increased by providing a selectin polypeptide, e.g. E-selectin or L-selectin immobilized on a solid phase and contacting the solid phase with a fluid sample containing a cell population. The solid phase is contacted with the fluid sample shear stress is achieved at the surface of the solid phase. Cells that adhere to the solid phase are recovered.

Levels of engrafted stem cells in a subject, e.g., human are increased by administering to the subject an agent that increases cell-surface or expression of a HCELL polypeptide in the subject. Suitable agents include for example, a nucleic acid that encodes a CD44, glycosyltransferase or a glycosidase polypeptide. Alternatively, levels of engrafted stem cells in a subject are increased by administering to the subject a composition containing the cells isolated according to the above described methods.

The invention also features methods of treating hematopoietic disorders, e.g., leukemia in a subject. The hematopoietic disorder is treated by administering to the subject an agent that decreases the cell-surface or expression of a HCELL polypeptide in the subject. Alternatively, the hematopoietic disorder is treated by providing blood from the subject and contacting the blood with one or more agents that specifically bind to a HCELL polypeptide under conditions sufficient to form a complex between the agents and a blood cell. The complex is detected, if present and removed from the blood. The blood is re-introduced to the subject.

Additionally, a hematopoietic disorder is treated by providing blood from the subject and a selectin polypeptide, e.g., E-selectin or L-selectin immobilized on a solid phase and contacting the solid phase with a the blood. The solid phase is contacted with the blood sample so shear stress is achieved at the surface of the solid phase. The blood is then re-introduced onto the subject.

Further the hematopoietic disorder is treated by administering to the subject an agent that specifically bind to the HCELL glycoprotein.

The invention also features, a method of treating an inflammatory disorder in a subject, by administering to a subject a HCELL gylcoprotein or fragment thereof.

The invention further features a method of diagnosing or determining the susceptibility to a hematologic disorder in a subject, by contacting a subject derived cell population with one or more agents that specifically bind a HCELL glycoprotein under conditions sufficient to form a complex between the agent and cell, and detecting the complex. The presence of the complex indicates the presence of or the susceptibility to a hematologic disorder in the subject.

Additionally, the invention feature a method of determining the prognosis or efficacy of treatment of a hematologic disorder in a subject, by contacting a subject derived cell population with one or more agents that specifically bind a HCELL glycoprotein under conditions sufficient to form a complex between the agent and cell, if and detecting the complex.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 2 is a bar graph showing human hematopoietic cell rolling on freshly isolated human bone marrow endothelial cells.

FIG. 4A is a photograph of a membrane of a Blot Rolling Assay showing the E-selectin binding activity of HCELL exhaustively immunoprecipitated with anti-CD44 antibody (Hermes-1). (Pre-Ippt): Total KG1a lysate 10 μg; (lane 1): First round Hermes-1 immunoprecipitate; (lane 2): Second round Hermes-1 immunoprecipitate; (lane 3): Third round Hermes-1 immunoprecipitate; (lane 4): Residual lysate after three rounds of Hermes-1 immunoprecipitation.

FIG. 4B is a photograph of a membrane of a Blot Rolling Assay showing the E-selectin binding activity of exhaustively immunoprecipitated HCELL with Hermes-1 antibody and blot stained with HECA-452 antibody. (Pre-Ippt): Total KGia lysate 10 μg; (lane 1): First round Hermes-1 immunoprecipitate; (lane 2): Second round Hermes-1 immunoprecipitate; (lane 3): Third round Hermes-1 immunoprecipitate; (lane 4): Residual lysate after three rounds of Hermes-1 immunoprecipitation.

FIG. 13A is a bar chart showing rolling of CHO-P-selectin or mock transfectants on glutaraldehyde-fixed hematopoietic cell monolayers was measured in the parallel-plate flow chamber. KG1a and HL60 cells supported equivalent P-selectin-mediated CHO-P cell rolling at 0.4 dynes/cm$^2$.

FIG. 13B is a chart showing CHO-P cell rolling interactions on KG1a and HL60 cells that were measured over a similar shear stress range and were eliminated in the presence of EDTA and prevented by pretreating KG1a and HL60 cells with mocarhagin (10 µg/ml).

FIG. 14A is a photograph of an autoradiograph of Hermes-1 (CD44) and PL-2 (PSGL-1) immunoprecipitates and L-selectin ligand activity of HCELL and PSGL-1.

FIG. 15A-FIG. 15I are photomicrographs of lymphocytes bound to human HC CD44 or PSGL-1 in the Stamper-Woodruff Assay. Immunoaffinity purified KG1a or AML (M1) CD44 (1.5 µg) and KG1a PSGL-1 (2 or 6 µg, FIG. 15G, FIG. 15H and FIG. 15I, respectively) were prepared as described in the Methods and analyzed for L-selectin-mediated lymphocyte adherence in the Stamper-Woodruff assay. KG1a or AML (M1) CD44 (FIG. 15A and FIG. 15D, respectively) supported a distinctively higher number of lymphocytes than to respective N-glycosidase F-treated CD44 (FIG. 15B and FIG. 15E) and to isotype control immunoprecipitates, monoclonal Ab (Hermes-1) alone or L-selectin immunoprecipitate (All represented by FIG. 15C and FIG. 15F for KG1a and AML (M1), respectively). Anti-L-selectin Abs (10 µg/ml), 5 mM EDTA-containing assay medium or PMA-treated (50 ng/ml) lymphocytes completely inhibited lymphocyte adherence (also indicated in FIG. 15C and FIG. 15F from KG1a and AML (M1), respectively) verifying the specificity of lymphocyte L-selectin in this assay system. OSGE treatment markedly diminished lymphocyte binding (FIG. 15I).

(FIG. 17 A) RT-PCR expression analysis of FucTIV and FucTVII. Lane 1: FucTIV, Lane 2: FucTVII, Lane 3: β-actin, and Lane 4: ddH$_2$O. (FIG. 17 B) RT-PCR expression analysis of ST3GalIV. Lane 1: ST3Gal IV, Lane 2: β-actin, and Lane 3: ddH$_2$O.

DETAILED DESCRIPTION

Figure 1A:
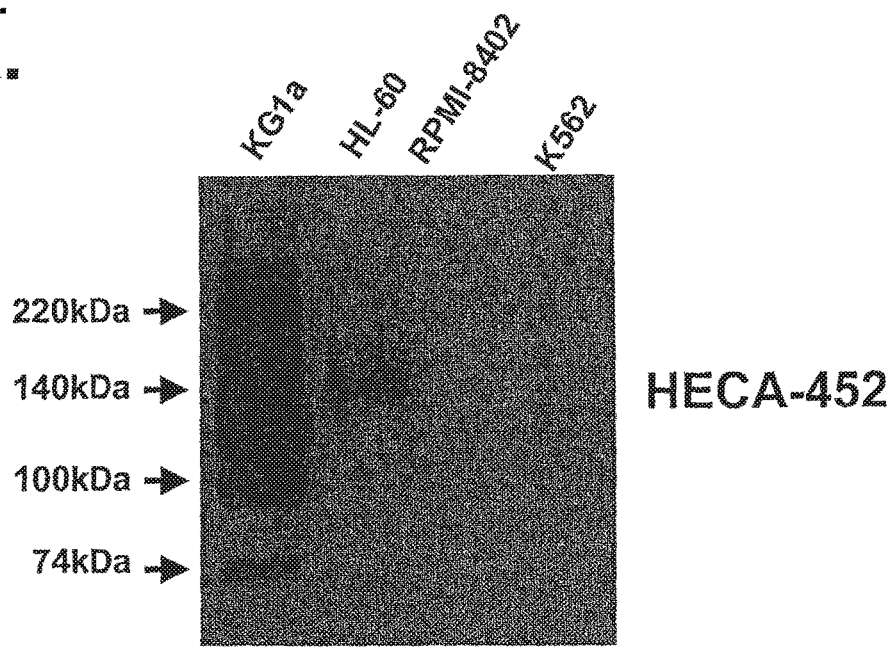
FIG. 1 A is a photograph of a Western Blot showing expression HECA-452-reactive epitopes on various human hematopoietic cell lines.
FIG. 1B is a bar graph showing cell tethering and rolling of hematopoietic cell lines (shear stress of 2.8 dynes/cm$^2$) on glutaraldehyde-fixed monolayers. Data are presented as mean±S.D. CHO-E cell rolling per field×5 fields, minimum of three experiments.

The present invention is based in part on the discovery of a novel glycosylated polypeptide expressed on normal human hemopoietic progenitor cells and on leukemic blasts designated hematopoietic cell E-selectin/L-selectin ligand (HCELL). The HCELL polypeptides are also referred to herein as "KG1a CD44". Using blot rolling assay it was demonstrated that HCELL is novel glycoform of CD44 containing HECA-452 reactive sialylated, fucosylated N-glycans. The HCELL polypeptide is a ligand for both a L-selectin and E-selectin. HCELL L-selectin and E-selectin ligand activity requires sialofucosylated N-linked glycans that are recognized by rat monoclonal antibody HECA-452 and is sulfation-independent.

CD44 is a broadly distributed cell surface glycoprotein receptor for the glycosamino glycan hyaluronan (HA) which is a major component of extracellular spaces. It is expressed on a diverse variety of cell types including most hematopoietic cells, keratinocytes, chondrocytes, many epithelial cell types, and some endothelial and neural cells. CD44 is known to participate in a wide variety of cellular functions, including cell-cell aggregation, retention of pericellular matrix, matrix-cell and cell-matrix signaling, receptor-mediated internalization/degradation of hyaluronan, and cell migration. All these functions are dependent upon CD44-hyaluronan interactions and is sulfation dependent.

The gene encoding CD44 gene consists of 20 exons (19 exons in earlier literature, exons 6a and 6b have been reclassified as exons 6 and 7, to make 20 exons total). Although a single gene located on the short arm of human chromosome 11 encodes CD44, multiple mRNA transcripts that arise from the alternative splicing of 12 of the 20 exons have been identified. The standard and most prevalent form of CD44 (termed CD44s) consists of a protein encoded by exons 1-5, 16-18, and 20. This form is the most predominant form on hematopoetic cells, and is also known as CD44H. CD44s exhibits the extracellular domains (exons 1-5 and 16), the highly conserved transmembrane domain (exon 18), and the cytoplasmic domain (exon 20). The 1482 bp of open reading frame mRNA for human CD44s results in translation of a polypeptide chain of ~37 kDa. Post-translational addition of N-linked and O-linked oligosaccharides contribute to the ~85-kDa molecular mass of the final CD44 protein as estimated by SDS-PAGE.

A HCELL polypeptide comprises an amino acid sequence of CD44 and binds to antibody having the binding specificity of monoclonal antibody HECA-452. (ATCC Number: HB-11485) HECA-452 recognizes cutaneous lymphocyte associated antigen. HECA-452 binding of HCELL decrease after N-glycosidase-F, sialidase or fucosidase treatment. Furthermore, HCELL activity, e.g., E-selectin and L-selectin binding also decreases upon N-glycosidase-F, sialidase, or fucosidase treatment demonstrating the importance of the sialofucosylated N-linked glycans in HCELL function. In contrast, sialylation of CD44 inhibits binding of CD44 to hyaluronic acid. Moreover, CD44 binding to hyaluronate is increased by sulfation, but sulfation is not necessary for the E- and L-selectin activity of HCELL.

Preferably the CD44 polypeptide is the standard or hematopoietic isoform of CD44 (CD44H). Alternately, the CD44 polypeptide is the R1 (CD44R1) or R2 isoform (CD44R2). For example, a HCELL polypeptide comprises the amino acid sequence of SEQ ID NO:1. (Gen Bank Acc. CAA40133; Table 1) A HCELL polypeptide is at least about 30%, 50%, 70%, 80%, or 95% identical to the polypeptide sequence of SEQ ID NO:1.

TABLE 1

(SEQ ID NO: 1)

| | | | | | |
|---|---|---|---|---|---|
| 1   | mdkfwwhaaw | glclvplsla | qidlnitcrf | agvfhvekng | rysisrteaa dlckafnstl |
| 61  | ptmaqmekal | sigfetcryg | fieghvvipr | ihpnsicaan | ntgvyiltsn tsqydtycfn |
| 121 | asappeedct | svtdlpnafd | gpititivnr | dgtryvqkge | yrtnpediyp snptdddvss |
| 181 | gssserssts | ggyifytfst | vhpipdedsp | witdstdrip | atnmdsshst tlqptanpnt |
| 241 | glvedldrtg | plsmttqqsn | sqsfstsheg | leedkdhptt | stltssnrnd vtggrrdpnh |
| 301 | segsttlleg | ytshyphtke | srtfipvtsa | ktgsfgvtav | tvgdsnsnvn rslsgdqdtf |
| 361 | hpsggshtth | gsesdghshg | sqeggantts | gpirtpqipe | wliilaslla lalilavcia |
| 421 | vnsrrrcgqk | kklvinsgng | avedrkpsgl | ngeasksqem | vhlvnkesse tpdqfmtade |
| 481 | trnlqnvdmk | igv | | | |

The standard or hematopoietic isoform of CD44 (CD44H) is a type 1 transmembrane molecule consisting of ~270 amino acids (aa) of extracellular domain (including 20 aa of leader sequence, a 21 aa transmembrane domain and a 72 aa cytoplasmic domain. The amino terminal ~180 aa are conserved among mammalian species (~85% homology). This region contains six conserved cysteines, and six conserved consensus sites for N glycosylation. Five conserved consensus sites for N-glycosylation are located in the amino terminal 120 aa of CD44. All five sites appear to be utilized in the murine and human cell lines. Several studies have shown that cell specific N-glycosylation can modulate the HA binding function of CD44. Cell lines and normal B-cells showed differenced in N-glycosylation associated with different HA binding states. In particular, CD44 from HA binding cells had less glycosylation than from non-HA binding cells. Additionally, removal of sialic acids (both from the cell surface and from CD44-Ig fusion proteins) enhances HA binding. Thus the HCELL CD44 glycoform of the invention is unlike any previously described CD44.

In contrast the non-conserved region (~aa 183 to 256) shows only ~35% similarity between mammalian species. This region contains potential sites for numerous carbohydrate modifications of CD44 and the site of alternative splicing which allows for the insertion of extra amino acid sequence from variable exons of the CD44 gene.

HCELL Polypeptides

One aspect of the invention pertains to isolated HCELL glycoproteins, and biologically active portions thereof, or derivatives, fragments, analogs or homologs thereof Also provided are polypeptide fragments suitable for use as immunogens to raise anti-HCELL antibodies. In one embodiment, native HCELL glycoproteins can be isolated from cells or tissue sources by an appropriate purification scheme using standard protein purification techniques.

In another embodiment, HCELL glycoproteins are produced by recombinant DNA techniques. Alternative to recombinant expression, a HCELL glycoprotein or polypeptide can be synthesized chemically using standard peptide synthesis techniques.

An "isolated" or "purified" protein or biologically active portion thereof is substantially free of cellular material or other contaminating proteins from the cell or tissue source from which the HCELL glycoprotein is derived, or substantially free from chemical precursors or other chemicals when chemically synthesized. The language "substantially free of cellular material" includes preparations of HCELL glycoprotein in which the protein is separated from cellular components of the cells from which it is isolated or recombinantly produced. In one embodiment, the language "substantially free of cellular material" includes preparations of HCELL glycoprotein having less than about 30% (by dry weight) of non-HCELL glycoprotein (also referred to herein as a "contaminating protein"), more preferably less than about 20% of non-HCELL glycoprotein, still more preferably less than about 10% of non-HCELL glycoprotein, and most preferably less than about 5% non-HCELL glycoprotein. When the HCELL glycoprotein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of HCELL glycoprotein in which the protein is separated from chemical precursors or other chemicals that are involved in the synthesis of the protein. In one embodiment, the language "substantially free of chemical precursors or other chemicals" includes preparations of HCELL glycoprotein having less than about 30% (by dry weight) of chemical precursors or non-HCELL chemicals, more preferably less than about 20% chemical precursors or non-HCELL chemicals, still more preferably less than about 10% chemical precursors or non-HCELL chemicals, and most preferably less than about 5% chemical precursors or non-HCELL chemicals.

Biologically active portions of a HCELL glycoprotein include peptides comprising amino acid sequences sufficiently homologous to or derived from the amino acid sequence of the HCELL glycoprotein, e.g., the amino acid sequence shown in SEQ ID NO: 1, that include fewer amino acids than the full length HCELL glycoproteins, and exhibit at least one activity of a HCELL glycoprotein, e.g., HECA-452 antibody reactivity, anti-CD44 antibody reactivity. E-selectin binding, or L-selectin binding. Typically, biologically active portions comprise a domain or motif with at least one activity of the HCELL glycoprotein, e.g., N-linked glycosylation sites. A biologically active portion of a HCELL glycoprotein can be a polypeptide which is, for example, 10, 25, 50, 100 or more amino acids in length. Preferably the biologically active portion of a HCELL glycoprotein includes the amino acid sequence of the N-terminal domain of a CD44 polypeptide.

The invention may contain at least one of the above-identified structural domains. Moreover, other biologically active portions, in which other regions of the protein are deleted, can be prepared by recombinant techniques and evaluated for one or more of the functional activities of a native HCELL glycoprotein, e.g., E-selectin, L-selection binding activity. In an embodiment, the HCELL glycoprotein has an amino acid sequence shown in SEQ ID NO: 1. In other embodiments, the HCELL glycoprotein is substantially homologous to SEQ ID NO: 1 and retains the functional activity of the protein of SEQ ID NO: 1 a yet differs in amino acid sequence due to natural allelic variation or mutagenesis, as described in detail below. Accordingly, in another embodiment, the HCELL glycoprotein is a protein that comprises an amino acid sequence at least about 45% homologous to the amino acid sequence of SEQ ID NO: 1 and retains the functional activity of the HCELL glycoproteins of SEQ ID NO: 1. Alternatively, a HCELL polypeptide has a CD44 amino acid sequence capable of N-linked glycosylation.

Chimeric and Fusion Proteins

The invention also provides HCELL chimeric or fusion proteins. As used herein, a HCELL "chimeric protein" or "fusion protein" comprises a HCELL polypeptide operatively linked to a non-HCELL polypeptide. A "HCELL polypeptide" refers to a polypeptide having an amino acid sequence corresponding to HCELL, whereas a "non-HCELL polypeptide" refers to a polypeptide having an amino acid sequence corresponding to a protein that is not substantially homologous to the HCELL glycoprotein, e.g., a protein that is different from the HCELL glycoprotein and that is derived from the same or a different organism. Within a HCELL fusion protein the HCELL polypeptide can correspond to all or a portion of a HCELL glycoprotein. In one embodiment, a HCELL fusion protein comprises at least one biologically active portion of a HCELL glycoprotein. In another embodiment, a HCELL fusion protein comprises at least two biologically active portions of a HCELL glycoprotein. In yet another embodiment, a HCELL fusion protein comprises at least three biologically active portions of a HCELL glycoprotein. Within the fusion protein, the term "operatively linked" is intended to indicate that the HCELL polypeptide and the non-HCELL polypeptide are fused in-frame to each other. The non-HCELL polypeptide can be fused to the N-terminus or C-terminus of the HCELL polypeptide. For example, in one embodiment a HCELL fusion protein comprises a HCELL anti-CD44 binding domain operably linked to the extracellular domain of a second protein. Such fusion proteins can be further utilized in screening assays for compounds which modulate HCELL activity.

In one embodiment, the fusion protein is a GST-HCELL fusion protein in which the HCELL sequences are fused to the C-terminus of the GST (i.e., glutathione S-transferase) sequences. Such fusion proteins can facilitate the purification of recombinant HCELL.

In another embodiment, the fusion protein is a HCELL glycoprotein containing a heterologous signal sequence at its N-terminus. For example, the native HCELL signal sequence can be removed and replaced with a signal sequence from another protein. In certain host cells (e.g., mammalian host cells), expression and/or secretion of HCELL can be increased through use of a heterologous signal sequence.

In one embodiment, the fusion protein is a HCELL-immunoglobulin fusion protein in which the HCELL sequence of fragment thereof are fused to sequences derived from a member of the immunoglobulin protein family. The HCELL-immunoglobulin fusion proteins of the invention can be incorporated into pharmaceutical compositions and administered to a subject to inhibit an interaction between a HCELL ligand and a HCELL glycoprotein on the surface of a cell, to thereby suppress HCELL-mediated signal transduction in vivo. The HCELL-immunoglobulin fusion proteins can be used to affect the bioavailability of a HCELL cognate ligand. Inhibition of the HCELL ligand/HCELL interaction may be useful therapeutically for both the treatment of proliferative and differentiative disorders, as well as modulating (e.g., promoting or inhibiting) cell survival.

Moreover, the HCELL-immunoglobulin fusion proteins of the invention can be used as immunogens to produce anti-HCELL antibodies in a subject, to purify HCELL ligands, and in screening assays to identify molecules that inhibit the interaction of HCELL with a HCELL ligand.

A HCELL chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A HCELL-encoding nucleic acid can be cloned into such an expression vector such that the fusion moiety is linked in-frame to the HCELL glycoprotein.

HCELL Agonists and Antagonists

The present invention also pertains to variants of the HCELL glycoproteins that function as either HCELL agonists (mimetics) or as HCELL antagonists. Variants of the HCELL glycoprotein can be generated by mutagenesis, e.g., discrete point mutation or truncation of the HCELL glycoprotein. An agonist of the HCELL glycoprotein can retain substantially the same, or a subset of, the biological activities of the naturally occurring form of the HCELL glycoprotein. An antagonist of the HCELL glycoprotein can inhibit one or more of the activities of the naturally occurring form of the HCELL glycoprotein by, for example, competitively binding to a downstream or upstream member of a cellular signaling cascade which includes the HCELL glycoprotein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the HCELL glycoproteins.

Variants of the HCELL glycoprotein that function as either HCELL agonists (mimetics) or as HCELL antagonists can be identified by screening combinatorial libraries of mutants, e.g., truncation mutants, of the HCELL glycoprotein for HCELL glycoprotein agonist or antagonist activity. In one embodiment, a variegated library of HCELL variants is generated by combinatorial mutagenesis at the nucleic acid level and is encoded by a variegated gene library. A variegated library of HCELL variants can be produced by, for example, enzymatically ligating a mixture of synthetic oligonucleotides into gene sequences such that a degenerate set of potential HCELL sequences is expressible as individual polypeptides, or alternatively, as a set of larger fusion proteins (e.g., for phage display) containing the set of HCELL sequences therein. There are a variety of methods which can be used to produce libraries of potential HCELL variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential HCELL sequences. Methods for synthesizing degenerate oligonucleotides are known in the art (see, e.g., Narang (1983) *Tetrahedron* 39:3; Itakura et al. (1984) *Annu Rev Biochem* 53:323; Itakura et al. (1984) *Science* 198:1056; Ike et al. (1983) *Nucl Acid Res* 11:477.

Anti-HCELL Antibodies

The invention encompasses antibodies and antibody fragments, such as $F_{ab}$ or $(F_{ab})2$, that bind immunospecifically to any of the polypeptides of the invention. An isolated HCELL glycoprotein, or a portion or fragment thereof, can be used as an immunogen to generate antibodies that bind HCELL using standard techniques for polyclonal and monoclonal antibody preparation. The full-length HCELL glycoprotein can be used or, alternatively, the invention provides antigenic peptide fragments of HCELL for use as immunogens. The antigenic peptide of HCELL comprises at least 4 amino acid residues of the amino acid sequence shown in SEQ ID NO: 1 and encompasses an epitope of HCELL such that an antibody raised against the peptide forms a specific immune complex with HCELL. Preferably, the antigenic peptide comprises at least 6, 8, 10, 15, 20, or 30 amino acid residues. Longer antigenic peptides are sometimes preferable over shorter antigenic peptides, depending on use and according to methods well known to someone skilled in the art. More preferably the antigenic peptide comprises at least one N-linked glycosylation site.

In certain embodiments of the invention, at least one epitope encompassed by the antigenic peptide is a region of HCELL that is located on the surface of the protein, e.g., a hydrophilic region. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824-3828; Kyte and Doolittle 1982, *J. Mol. Biol.* 157: 105-142, each incorporated herein by reference in their entirety.

As disclosed herein, HCELL glycoprotein sequence, or derivatives, fragments, analogs or homologs thereof, may be utilized as immunogens in the generation of antibodies that immunospecifically-bind these protein components. The term "antibody" as used herein refers to immunoglobulin molecules and immunologically active portions of immunoglobulin molecules, i.e., molecules that contain an antigen binding site that specifically binds (immunoreacts with) an antigen, such as HCELL. Such antibodies include, but are not limited to, polyclonal, monoclonal, chimeric, single chain, $F_{ab}$ and $F(_{ab}')2$ fragments, and an Fab expression library. In a specific embodiment, antibodies to human HCELL glycoproteins are disclosed. Various procedures known within the art may be used for the production of polyclonal or monoclonal antibodies to a HCELL glycoprotein sequence of SEQ ID NO: 1, or derivative, fragment, analog or homolog thereof. Some of these proteins are discussed below.

For the production of polyclonal antibodies, various suitable host animals (e.g., rabbit, goat, mouse or other mammal) may be immunized by injection with the native protein, or a synthetic variant thereof, or a derivative of the foregoing. An appropriate immunogenic preparation can contain, for example, recombinantly expressed HCELL glycoprotein or a chemically synthesized HCELL polypeptide. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory agents. If desired, the antibody molecules directed against HCELL can be isolated from the mammal (e.g., from the blood) and further purified by well known techniques, such as protein A chromatography to obtain the IgG fraction.

The term "monoclonal antibody" or "monoclonal antibody composition", as used herein, refers to a population of antibody molecules that contain only one species of an antigen binding site capable of immunoreacting with a particular epitope of HCELL. A monoclonal antibody composition thus typically displays a single binding affinity for a particular HCELL glycoprotein with which it immunoreacts. For preparation of monoclonal antibodies directed towards a particular HCELL glycoprotein, or derivatives, fragments, analogs or homologs thereof, any technique that provides for the production of antibody molecules by continuous cell line culture may be utilized. Such techniques include, but are not limited to, the hybridoma technique (see Kohler & Milstein, 1975 Nature 256: 495-497); the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96). Each of the above citations are incorporated herein by reference in their entirety.

According to the invention, techniques can be adapted for the production of single-chain antibodies specific to a HCELL glycoprotein (see e.g., U.S. Pat. No. 4,946,778). In addition, methodologies can be adapted for the construction of Fab expression libraries (see e.g., Huse, et al., 1989 Science 246: 1275-1281) to allow rapid and effective identification of monoclonal Fab fragments with the desired specificity for a HCELL glycoprotein or derivatives, fragments, analogs or homologs thereof. Non-human antibodies can be "humanized" by techniques well known in the art. See e.g., U.S. Pat. No. 5,225,539. Antibody fragments that contain the idiotypes to a HCELL glycoprotein may be produced by techniques known in the art including, but not limited to: (i) an $F_{(ab')}2$ fragment produced by pepsin digestion of an antibody molecule; (ii) an $F_{ab}$ fragment generated by reducing the disulfide bridges of an $F_{(ab')}2$ fragment; (iii) an $F_{ab}$ fragment generated by the treatment of the antibody molecule with papain and a reducing agent and (iv) $F_v$ fragments.

Additionally, recombinant anti-HCELL antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in International Application No. PCT/US86/02269; European Patent Application No. 184,187; European Patent Application No. 171,496; European Patent Application No. 173,494; PCT International Publication No. WO 86/01533; U.S. Pat. Nos. 4,816,567; 5,225,539; European Patent Application No. 125,023; Better et al. (1988) Science 240:1041-1043; Liu et al. (1987) PNAS 84:3439-3443; Liu et al. (1987) J Immunol. 139:3521-3526; Sun et al. (1987) PNAS 84:214-218; Nishimura et al. (1987) Cancer Res 47:999-1005; Wood et al. (1985) Nature 314:446-449; Shaw et al. (1988) J Natl Cancer Inst 80:1553-1559); Morrison (1985) Science 229:1202-1207; Oi et al. (1986) BioTechniques 4:214; Jones et al. (1986) Nature 321:552-525; Verhoeyan et al. (1988) Science 239:1534; and Beidler et al. (1988) J Immunol 141:4053-4060. Each of the above citations are incorporated herein by reference in their entirety.

In one embodiment, methodologies for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of a HCELL glycoprotein is facilitated by generation of hybridomas that bind to the fragment of a HCELL glycoprotein possessing such a domain. Antibodies that are specific for a N-linked glycosylation site, or derivatives, fragments, analogs or homologs thereof, are also provided herein.

Anti-HCELL antibodies may be used in methods known within the art relating to the localization and/or quantitation of a HCELL glycoprotein (e.g., for use in measuring levels of the HCELL glycoprotein within appropriate physiological samples, for use in diagnostic methods, for use in imaging the protein, and the like). In a given embodiment, antibodies for HCELL glycoproteins, or derivatives, fragments, analogs or homologs thereof, that contain the antibody derived binding domain, are utilized as pharmacologically-active compounds [hereinafter "Therapeutics"].

An anti-HCELL antibody (e.g., monoclonal antibody) can be used to isolate HCELL by standard techniques, such as affinity chromatography or immunoprecipitation. An anti-HCELL antibody can facilitate the purification of natural HCELL from cells and of recombinantly produced HCELL expressed in host cells. Moreover, an anti-HCELL antibody can be used to detect HCELL glycoprotein (e.g., in a cellular lysate or cell supernatant) in order to evaluate the abundance and pattern of expression of the HCELL glycoprotein. Anti-HCELL antibodies can be used diagnostically to monitor protein levels in tissue as part of a clinical testing procedure, e.g., to, for example, determine the efficacy of a given treatment regimen. Alternatively, anti-HCELL antibodies are used to treat or diagnosis leukemia. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, (3-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

HCELL Recombinant Expression Vectors and Host Cells

Another aspect of the invention pertains to vectors, preferably expression vectors, containing a nucleic acid encoding HCELL polypeptides, fusion polypeptides, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of HCELL polypeptides or fusion polypeptides in prokaryotic or eukaryotic cells. For example, HCELL polypeptides or fusion polypeptides can be expressed in bacterial cells such as *Escherichia coli*, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET lid (Studier et al., Gene Expression Technology: Methods in Enzymology 185, Academic Press, San Diego, Calif. (1990) 60-89).

One strategy to maximize recombinant protein expression in *E. coli* is to express the protein in a host bacteria with an impaired capacity to proteolytically cleave the recombinant protein. See, e.g., Gottesman, Gene Expression Technology: Methods in Enzymology 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (see, e.g., Wada, et al., 1992. Nucl. Acids Res. 20: 2111-2118). Such alteration of nucleic acid sequences of the invention can be carried out by standard DNA synthesis techniques.

In another embodiment, the HCELL polypeptides or fusion polypeptides expression vector is a yeast expression vector. Examples of vectors for expression in yeast *Saccharomyces* cerivisae include pYepSecl (Baldari, et al., 1987. EMBO J. 6: 229-234), pMFa (Kurjan and Herskowitz, 1982. *Cell* 30: 933-943), pJRY88 (Schultz et al., 1987. *Gene* 54: 113-123), pYES2 (Invitrogen Corporation, San Diego, Calif.), and picZ (InVitrogen Corp, San Diego, Calif.).

Alternatively, HCELL polypeptides or fusion polypeptides can be expressed in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In yet another embodiment, a nucleic acid of the invention is expressed in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., Molecular Cloning: A Laboratory Manual. 2nd ed., Cold Spring Harbor Laboratory, Cold Spring Harbor Laboratory Press, Cold Spring Harbor, N. Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally regulated promoters are also encompassed, e.g., the murine hox promoters (Kessel and Gruss, 1990. Science 249: 374-379) and the a-fetoprotein promoter (Campes and Tilghman, 1989. Genes Dev. 3: 537-546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to HCELL polypeptides or fusion polypeptides mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," Reviews-Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, HCELL polypeptides or fusion polypeptides can be expressed in bacterial cells such as E. coli, insect cells, yeast or mammalian cells (such as human, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd ed., Cold Spring Harbor Laboratory, Cold Spring Harbor Laboratory Press, Cold Spring Harbor, N. Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding HCELL polypeptides or fusion polypeptides or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) HCELL polypeptides or fusion polypeptides. Accordingly, the invention further provides methods for producing HCELL polypeptides or fusion polypeptides using the host cells of the invention. In one embodiment, the method comprises culturing the host cell of invention (into which a recombinant expression vector encoding HCELL polypeptides or fusion polypeptides has been introduced) in a suitable medium such that HCELL polypeptides or fusion polypeptides is produced. In another embodiment, the method further comprises isolating HCELL polypeptides or fusion polypeptides polypeptide from the medium or the host cell.

Method of Identifying Stem Cells

The invention provides various methods of identifying and/or isolating stem cells. A stem cell is a pluripotent cell of mesodermal, ectodermal or endodermal origin. Preferably, a stem cell is of mesodermal origin. More preferably, a stem cell is a hematopoiteic progenitor cell.

A stem cell is identified by contacting a test cell population with one or more agents, e.g., a protein, polypeptide or small molecule, that specifically bind to a HCELL polypeptide. Preferably, an agent is an antibody or a fragment thereof. The antibody can be polyclonal or monoclonal. For example, an agent is a HCELL antibody. Alternatively, an agent is an anti-CD44 antibody, or a HECA-452 antibody.

Specifically binding is meant that the interaction between cell and the agent is sufficient to form a complex. A cell/agent complex is detected. Presence of a complex indicates that the test cell is a stem cell. In an alternative method, the stem cell is isolated from the test cell population by removing the complex from the test cell population. The complex can be separated from the test cell population by methods known in the art, e.g. flow cytometry. Additionally, the stem cell can be further isolated by separating the stem cell from the agent(s) by disrupting the complex. The complex can be disrupted from example by ion chelation with dilute EDTA.

Alternately, a stem cell can be identified by providing a selectin polypeptide, e.g. E-selectin or L-selectin, immobilized on a solid phase e.g., glass, plastic or membrane and contacting the solid phase with a fluid sample containing a suspension of test cells. In some aspects the fluid sample is moving. By a moving fluid sample it is meant that the sample flows across the surface of the membrane in a unidirectional manner. Interactions between fluid sample in flow and immobilized ligand can be examined under a wide range of defined flow conditions, ranging from static incubation through physiological levels of shear flow, static conditions and serial application of static and shear conditions, and into supraphysiologic shear levels. For example, shear flow conditions is a flow force greater than 0.6 dynes/cm$^2$. Alternatively, shear flow condition is a flow force at least 2.8 dynes/cm$^2$. Additionally, shear flow condition is a flow force of at least 9.0 dynes/cm$^2$. In some aspects, the fluid move across the membrane such that physiological shear stress is achieved at the surface. The interaction between the solid phase and the cells is then determined. An interaction between the cells of the fluid sample and the solid phase indicates that the cell is a stem cell.

Also include in the invention is a method of isolating stem cells. The method includes providing a selectin polypeptide on a solid phase and contacting the solid phase with a fluid sample containing a suspension of cells. The cells that adhere to the solid phase are then recovered. Bound cells can be removed by any method known in the art (e.g., by ion chelation with dilute EDTA and/or application of high shear force). Bound cells recovered from the blot surface can thus be collected and analyzed for phenotype or biological functions after elution. The ligand immobilized on the matrix can be reused to compare interactions among various cell groups or manipulated in situ to define characteristics of the cell population under investigation.

The interaction between the cells and the solid phase can be, e.g., rolling, firm attachments or specific interaction. In some aspects, the specific interaction is determined by the affinity coefficient. For example a specific interaction is an interaction that has a $K_d$ is in the range of 0.1 mM to 7 mM. Preferably, the $K_d$ is greater than 1 mM.

A cell/agent interaction or alternately a cell/solid phase interaction can be determined for example, by visual inspection under a microscope, colormetrically, flourometrically, by flow cytometry or using a parallel plate flow chamber assay. Alternatively, the interaction is analyzed by labeling the cells, HCELL, polypeptide or the agent using florescent labels, biotin, enzymes such as alkaline phosphatase, horseradish peroxidase or beta-galactosidase, radioactive isotopes or other labels known in the art. The label can be added to the cells, HCELL polypeptide or the agent prior or subsequent to contacting the test cell population with the agent. The membrane or solid phase can then be subject to spectrophotometic or radiographic analysis to quantify the number interacting with the selectin polypeptide of solid phase.

The invention also provide methods of treating cell disorders such as hematopoiteic disorders, cancer, or disorders amenable to treatment with a stem cell (i.e., stem cell therapy) such as myocardial infarction, Parkinson's disease, diabetes, congenital muscle dystrophies, stroke, genetic/congenital disorders (e.g., osteogenesis imperfecta) and liver disorders in a mammal, e.g., human by administering the cells isolated by the above described methods.

Methods of Increasing E-Selectin/L-Selectin Ligand Affinity

The invention provides a method of increasing the affinity of a cell for E-selectin and/or L-selectin, by providing a cell and contacting the cell with one or more agents that increases cell-surface expression or activity a HCELL polypeptide on the cell.

The cell can be any cell capable of expressing HCELL polypeptide. For example the cell can be a stem cell (i.e., a pluripotent cell). A cell can be of mesodermal, ectodermal or endodermal origin. Preferably, a cell of mesodermal origin. More preferably a cell is a hematopoietic progenitor cell. The cell population that is exposed to, i.e., contacted with, the compound can be any number of cells, i.e., one or more cells, and can be provided in vitro, in vivo, or ex vivo.

Suitable agents can be, e.g., a polypeptide, a nucleic acid. For example an agent can be a CD44, glycosyltransferase or glycosidase polypeptide, nucleic acid that encodes a CD44, glycosyltransferase or glycosidase polypeptide or a nucleic acid that increases expression of a nucleic acid that encodes a include CD44, glycosyltransferase, or glycosidase polypeptide and, and derivatives, fragments, analogs and homologs thereof. A nucleic acid that increase expression of a nucleic acid that encodes a CD44, glycosyltransferase, or glycosidase polypeptide includes, e.g., promoters, enhancers. The nucleic acid can be either endogenous or exogenous.

Suitable sources of nucleic acids encoding CD44 polypeptide include for example the human CD44 nucleic acid (and the encoded protein sequences) available as GenBank Accession Nos. LO5407 and CAA40133, respectively. Other sources include human CD44 nucleic acid and protein sequences are shown in GenBank Accession No. U35632 and P16079, respectively, and are incorporated herein by reference in their entirety. Suitable sources of nucleic acids encoding glycosyltransferase polypeptide include for example the human glycosyltransferase nucleic acid (and the encoded protein sequences) available as GenBank Accession Nos. AJ276689 and CAB81779, respectively. Suitable sources of nucleic acids encoding glycosidase polypeptide include for example the human glycosidase nucleic acid (and the encoded protein sequences) available as GenBank Accession Nos. AJ278964 and CAC08178, respectively. The use of other CD44, glycosyltransferase, or glycosidase polypeptides and nucleic acids know in the art are also within the scope of the invention.

The agent can be exposed to the cell either directly (i.e., the cell is directly exposed to the nucleic acid or nucleic acid-containing vector) or indirectly.

HCELL expression can be measured at the nucleic acid or protein level. Expression of the nucleic acids can be measured at the RNA level using any method known in the art. For example, northern hybridization analysis using probes which specifically recognize one or more of these sequences can be used to determine gene expression. Alternatively, expression can be measured using reverse-transcription-based PCR assays. Expression can be also measured at the protein level, i.e., by measuring the levels of polypeptides encoded by the gene products. Such methods are well known in the art and include, e.g., immunoassays based on antibodies to proteins encoded by the genes.

HCELL activity can be measured for example by L-selectin or E-selectin binding activity Methods of Increasing Engraftment Potential of a Cell The invention provides methods of increasing the engraftment potential of a cell.

By increasing engraftment potential is meant that the cell has a greater survival rate after transplantation as compared to an untreated cell.

A cell can of mesodermal, ectodermal or endoderamal origin. Preferably, the cell is a stem cell. More preferably the cell is of mesodermal origin. For example, the cell is a hematopoietic progenitor cell.

Included in the invention is a method of increasing the engraftment potential of a cell by providing a cell and contacting said cell with one or more agents that increases cell-surface expression or activity of a HCELL polypeptide on the cell. The invention further provides method of increasing levels of engrafted stem cells in a subject, e.g., human by administering to the subject an agent that increases cell-surface or expression of the HCELL on one or more stem cells in the subject. The agent can be administered in vivo, ex vivo or in vitro.

Also included in the invention is a method of increasing the engraftment potential of a cell population by providing a selectin polypeptide, e.g., E-selectin or L-selectin immobilized on a solid phase, phase e.g., glass, plastic or membrane and contacting the solid phase with a fluid sample containing a suspension of test cells. In some aspects the fluid sample is moving. By a moving fluid sample it is meant that the sample flows across the surface of the membrane in a unidirectional manner. Interactions between fluid sample in flow and immobilized ligand can be examined under a wide range of defined flow conditions, ranging from static incubation through physiological levels of shear flow, static conditions and serial application of static and shear conditions, and into supraphysiologic shear levels. For example, shear flow conditions is a flow force greater than 0.6 dynes/cm$^2$. Alternately, shear flow condition is a flow force at least 2.8 dynes/cm$^2$. Additionally, shear flow condition is a flow force of at least 9.0 dynes/cm$^2$. In some aspects, the fluid move across the membrane such that physiological shear stress is achieved at the surface. The cells that adhere to the solid phase are then recovered. Bound cells can be removed by any method known in the art (e.g., by ion chelation with dilute EDTA and/or application of high shear force). Bound cells recovered from the blot surface can thus be collected and analyzed for phenotype or biological functions after elution. The ligand immobilized on the matrix can be reused to compare interactions among various cell groups or manipulated in situ (as outlined below) to define characteristics of the cell population under investigation. Further provided by the invention is a method of increasing levels of engrafted stem cells in a subject, by administering to subject a composition comprising the cells isolated according to the above methods.

Suitable agents can be, e.g., a polypeptide, a nucleic acid. For example an agent can be a CD44, glycosyltransferase or glycosidase polypeptide, nucleic acid that encodes a CD44, glycosyltransferase or glycosidase polypeptide or a nucleic acid that increases expression of a nucleic acid that encodes a include CD44, glycosyltransferase, or glycosidase polypeptide and, and derivatives, fragments, analogs and homologs thereof. A nucleic acid that increase expression of a nucleic acid that encodes a CD44, glycosyltransferase, or glycosidase polypeptide includes, e.g., promoters, enhancers. The nucleic acid can be either endogenous or exogenous.

Suitable sources of nucleic acids encoding CD44 polypeptide include for example the human CD44 nucleic acid (and the encoded protein sequences) available as GenBank Accession Nos. L05407 and CAA40133, respectively. Other sources include human CD44 nucleic acid and protein sequences are shown in GenBank Accession No. U35632 and P16079, respectively, and are incorporated herein by reference in their entirety. Suitable sources of nucleic acids encoding glycosyltransferase polypeptide include for example the human glycosyltransferase nucleic acid (and the encoded protein sequences) available as GenBank Accession Nos. AJ276689 and CAB81779, respectively. Suitable sources of nucleic acids encoding glycosidase polypeptide include for example the human glycosidase nucleic acid (and the encoded protein sequences) available as GenBank Accession Nos. AJ278964 and CAC08178, respectively. The use of other CD44, glycosyltransferase, or glycosidase polypeptides and nucleic acids know in the art are also within the scope of the invention.

The subject is preferably a mammal. The mammal can be, e.g., a human, non-human primate, mouse, rat, dog, cat, horse, or cow. Additionally, the subject suffers from or is at risk of developing a hematopoietic disorder, (e.g., leukemia), cancer, or inflammatory disorders, including chronic inflammatory disorders, e.g., (rheumatoid arthritis).

A mammal suffering from or at risk of developing a hematopoietic disorder, (e.g., leukemia), cancer, inflammatory disorders, including inflammatory chronic inflammatory disorders, (e.g., rheumatoid arthritis) can be identified by the detection of a known risk factor, e.g., gender, age, prior history of smoking, genetic or familial predisposition, attributed to the particular disorder. Alternatively, a mammal suffering from or at risk of developing a hematopoietic disorder, (e.g., leukemia), cancer, inflammatory disorders, including inflammatory chronic inflammatory disorders, (e.g., rheumatoid arthritis) can be identified by methods known in the art to diagnosis a particular disorder.

Methods of Treating Hematopoietic Disorders

The invention provides a method of treating hematopoietic disorders, (e.g., leukemia, aplastic anemia, non-Hodgkin's lymphoma, chronic myeloid leukemia, multiple myeloma chronic lymphocytic leukemia, and various myelodysplastic syndromes), in a subject, by administering to the subject an agent that decreases the cell-surface or expression of the HCELL polypeptide in the subject.

The invention further provides a method of treating hematopoietic disorders in a subject by providing blood from the subject and contacting the blood with one or more agents that specifically bind a HCELL polypeptide under conditions sufficient to form a complex between the agent and a blood cell in the blood. Preferably the blood cell is cancerous. More preferably the blood cell is a leukemic blood cell Complex formation is detected and the complex is removed from the blood thereby removing the cell. The blood is then reintroduced into the subject.

Suitable agents include, a protein, polypeptide or small molecule, that specifically bind to a HCELL polypeptide. Preferably, an agent is an antibody or a fragment thereof. The antibody can be polyclonal or monoclonal. For example, an agent is a HCELL antibody. Alternatively, an agent is an anti-CD44 antibody, or a HECA-452 antibody. Specifically binding is meant that the interaction between cell and the agent is sufficient to form a complex. The complex can be separated from the blood by methods known in the art, e.g., flow cytometry.

Also included in the invention is a method of treating hematopoietic disorders in a subject by providing blood from the subject and a selectin polypeptide, e.g., E-selectin or L-selectin immobilized on a solid phase e.g., glass, plastic or membrane and contacting the solid phase with a the blood. In some aspects the blood sample is moving. By a moving a blood sample it is meant that the sample flows across the surface of the membrane in a unidirectional manner. Interactions between blood sample in flow and immobilized ligand can be examined under a wide range of defined flow conditions, ranging from static incubation through physiological levels of shear flow, static conditions and serial application of static and shear conditions, and into supraphysiologic shear levels. For example, shear flow conditions is a flow force greater than 0.6 dynes/cm$^2$. Alternatively, shear flow condition is a flow force at least 2.8 dynes/cm$^2$. Additionally, shear flow condition is a flow force of at least 9.0 dynes/cm$^2$. In some aspects, the blood moves across the membrane such that physiological shear stress is achieved at the surface. The blood is then re-introduced into the subject.

Blood removal and re-infusion into a subject is accomplished by plasmapheretic techniques known in the art.

The invention further provides methods of treating hematopoietic disorders in a subject by administering to the subject an agent that specifically binds to a HCELL glycoprotein. The agent can be for example a polypeptide or small molecule. Preferably, the agent is a HCELL antibody. Specifically binding is meant that the interaction between HCELL glycoprotein and the agent is sufficient to form a complex. Upon complex formation, the agent may activate complement or mediate cellular toxicity, (e.g., antibody dependent cellular cytotoxicity (ADCC)) or other direct immunologic effects.

Alternatively, a hematopoietic disorder can be treated by administering to the subject an agent that includes a first and second domain. The first domain includes a compound that specifically binds to a HCELL glycoprotein. Preferably the first domain is a HCELL antibody or fragment thereof. The second domain includes a toxin linked by a covalent bond, e.g., peptide bond, to the first domain. A toxin includes any compound capable of destroying or selectively killing a cell in which it comes in contact. By "selectively killing" means killing those cells to which the first domain binds. Examples of toxins include, Diphtheria toxin (DT) Pseudomonas exotoxin (PE), ricin A (RTA), gelonin, pokeweed antiviral protein, and dodecandron.

The first and second domains can occur in any order, and the agent can include one or more of each domain.

The subject is preferably a mammal. The mammal can be, e.g., a human, non-human primate, mouse, rat, dog, cat, horse, or cow.

Methods of Diagnosing or Determining the Susceptibility to a Hematologic Disorder The invention provides a method of diagnosing or determining the susceptibility to a hematologic disorder in a subject by contacting a subject derived cell population with one or more agents that specifically bind a HCELL glycoprotein. Specifically binding is meant that the interaction between cell and the agent is sufficient to form a complex. A cell/agent complex is detected. Presence of a complex indicates the presence of or the susceptibility to a hematalogic disorder in the subject Hematologic disorders that can be detected by this method include for example, anemia, neutropenia, thrombicytosis, myeloproliferative disorders or hematologic neoplasms.

The subject is preferably a mammal. The mammal can be, e.g., a human, non-human primate, mouse, rat, dog, cat, horse, or cow.

Methods of Determining the Prognosis or Efficacy of Treatment of a Hematologic Disorder The invention provides a method of determining the prognosis or efficacy of treatment of hematologic disorder in a subject by contacting a subject derived cell population with one or more agents that specifically bind a HCELL glycoprotein. Specifically binding is meant that the interaction between cell and the agent is sufficient to form a complex. A cell/agent complex is detected. Absence of a complex indicates favorable prognosis or efficacious treatment of the hematologic disorder in the subject. Presence of a complex indicates an unfavorable prognosis or non-efficacious treatment of the hematologic disorder in the subject.

By "efficacious" is meant that the treatment leads to a decrease in the hematologic disorder in the subject. When treatment is applied prophylactically, "efficacious" means that the treatment retards or prevents a hematologic disorder.

Hematologic disorders that can be detected by this method include for example, example, anemia, neutropenia, thrombicytosis, myeloproliferative disorders or hematologic neoplasms.

The subject is preferably a mammal. The mammal can be, e.g., a human, non-human primate, mouse, rat, dog, cat, horse, or cow.

Method of Treating Inflammatory Disorders

The invention provides a method of treating inflammatory disorders in a subject, by administering to the subject an a HCELL glycoprotein or fragment thereof Inflammatory disorders include, for example, rheumatoid arthritis (RA), inflammatory bowel disease (IBD), and asthma.

Pharmaceutical Compositions Including HCELL Polypeptides Fusion Polypeptides or Nucleic Acids Encoding Same The HCELL polypeptides, or nucleic acid molecules encoding these fusion proteins and cells isolated according the methods of the invention, (also referred to herein as "Therapeutics" or "active compounds") and derivatives, fragments, analogs and homologs thereof, can be incorporated into pharmaceutical compositions suitable for administration. Such compositions typically comprise the nucleic acid molecule, protein, cell or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The active agents disclosed herein can also be formulated as liposomes. Liposomes are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the, conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In some embodiments, oral or parenteral compositions are formulated in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci. USA* 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

Sustained-release preparations can be prepared, if desired. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

The pharmaceutical compositions can be included in a container, pack, or dispenser together with instructions for administration.

The invention will be further described in the following examples, which do not limit the scope of the invention described in the claims.

Example 1

Identification of HECA-452-Reactive Membrane Glycoproteins on Human Hematopoietic Cells SDS-PAGE and Western blot analysis of HECA-452-reactive epitope(s) was performed on membrane proteins from various human hematopoietic cell lines.

Cell Preparation

Human hematopoietic cell lines (KG1a, HL6O, RPMI-8402 and K562) and the BM endothelial cell line BMEC-1 (Candal et al, 1996) were propagated in RPM1164O/10% FBS/1% penicillin-streptomycin (Life Technologies, Inc., Grand Island, N.Y.). Fresh circulating leukemia blasts were isolated by Ficoll-Hypaque (1.077-1.0800 g/ml) (ICN Biomedicals, Inc; Aurora, Ohio) density gradient centrifugation from the peripheral blood of patients where they represented >80% of all circulating leukocytes. Normal human BM cells were extracted from vertebral bodies of cadaveric organ donors obtained with consent of donor families and through the cooperation of the New England Organ Bank (Newton, Mass.). BM mononuclear cells were isolated by Ficoll-Hypaque (1.077-1.0800 g/ml) density gradient centrifugation. BM cells were separated into CD34+ and lineage+/CD34-subpopulations using a negative cell selection StemSep™ human progenitor enrichment column (StemCell Technologies, Inc., Vancouver, BC Canada) or, alternatively, using positive selection for CD34+ cells or for other subpopulations of bone marrow cells (monocytes (CD 14+), granulocytes (CD 15+), B cells (CD1 9+) or T cells (CD3+)) by immunomagnetic beading separation (Miltenyi Biotec, Auburn, Calif.). CD34+/CD44+, CD34+/CD44– and CD34–/CD44+ cell populations were isolated by cell sorting on a MoFlo apparatus (Cytomation) using fluorochrome-conjugated anti-CD34 moAb (HPCA-2) (Becton-Dickinson) and anti-CD44 moAb (Hermes-1) (a gift from Dr. Brenda Sandmaier, Fred Hutchinson Cancer Research Center).

SDS-PAGE and Western Blots

Membrane preparations of HPCs were isolated as previously described (Sackstein and Dimitroff, 2000). For SDS-PAGE and Western blotting, membrane preparations were diluted in reducing sample buffer and separated on 6-9% SDS-PAGE gels. Where indicated, membrane proteins were also treated with N-glycosidase F (Roche Molecular Biomedicals) (8 U/ml for 24 hr) or *Vibrio cholerae* neuraminidase (Roche Molecular Biochemicals) (0.1 U/ml H/H/Ca++ for 1 hr at 37° C.) as previously described (Sackstein and Dimitroff, 2000). Resolved membrane proteins were transferred to Sequi-Biot™ PVDF membrane (Bio-Rad, Inc., Hercules, Calif.) and blocked with PBS/Tween-20/20% FBS for 1 hr at 4° C. Blots were incubated with rat moAb HECA-452 (Pharmingen, San Diego, Calif.) (1.2 µg/ml PBS) or anti-PSGL-1 moAb 4H10 (Genetics Institute) for 1 hr at RT. Isotype control immunoblots using either rat 1 gM or mouse IgG were performed in parallel to evaluate non-specific reactive proteins. After 3 washes with PBS/0.1% Tween-20, blots were incubated with either AP-conjugated rabbit anti-rat 1 gM Abs (1:400) or AP-conjugated goat anti-mouse IgG (1:8000) depending on the primary Ab. AP substrate, Western Blue® (Promega, Madison, Wis.), was then added to develop the blots.

As illustrated in FIG. 1A, numerous and distinct HECA-452-reactive bands were detected on SDS-PAGE of membrane protein isolated from KG1a cells. Despite 10-fold less KG1a membrane protein loaded for analysis in these blots compared with that of HL6O, RPMI-8402 or K562 cellular membrane protein, KG1a cells contained markedly more HECA-452 staining displayed on several component protein bands. Only one broad band of approximately 140 kDa was detected on HL60 cells, which corresponded to the monomer species of PSGL-1 by immunoblot (FIG. 1A). There were no HECA-452-reactive membrane proteins from RPMI-8402 or K562 cells even though PSGL-1 was detected on Western blots of these cells by using anti-PSGL-1 antibody, 4H10 (Dimitroff et al., 2000). This finding suggested that these cells lacked the appropriate HECA-452 binding epitope and, at minimum, the E-selectin binding species of PSGL-1.

Example 2

Assessment of E-Selectin Binding of Human Hematopoietic Cells Under Defined Shear Flow Conditions To examine whether HECA-452 expression by human hematopoietic cell lines correlated with E-selectin ligand activity, parallel-plate flow chamber studies were performed to assess E-selectin binding under defined shear flow conditions.

Utilizing Cell Monolayers

E-selectin-mediated adhesive interactions, under defined shear stress, were examined between hematopoietic cell monolayers and suspensions of CHO-E (Chinese hamster ovary cells stably transfected with full-length cDNA encoding human E-selectin) in flow. CHO-E and empty vector constructs (CHO-Mock) were maintained in MEM 10% FBS/1% Penicillin/Streptomycin (Life Technologies, Inc.) and HAM's F-12 (Cellgro, Inc.)/5% FCS/1% Penicillin/Streptomycin, respectively. CHO-E cell tethering and rolling on hematopoietic cell monolayers was visualized by video microscopy in real time using the parallel-plate flow chamber. Prior to experimentation, CHO-E cells were harvested with 5 mM EDTA, washed twice in HBSS and suspended at 1xiO7/ml in HBSS/10 mM HEPES/2mMCaCl$_2$ (H/H/CC). Negative control groups were prepared by either adding 5 mM EDTA to the H/H assay buffer (to chelate Ca++ required for binding), treating CHO-E cells with anti-E-selectin Abs (clone 68-5111 1; Pharmingen) (10 µg/ml), or using CHO-empty vector transfectants (CHO-Mock cells). To prepare hematopoietic cell monolayers>90% confluent, suspensions of cells (KG1a, HL60, K562, or RPMI 8402) at 2×106/ml RPMI1640 without NaBicarbonate/2% FBS were cytocentrifuged in E-well plates at 5×106/well and then fixed in 3% glutaraldehyde. Reactive aldehyde groups were blocked in 0.2M lysine, and plated cells were suspended H/H/Ca++. In parallel, cells were also pretreated with either *Vibrio cholerae* neuraminidase (0.1µ/ml H/H/Ca++ for 1 hr at 37° C.) or 0-sialoglycoprotein endopeptidase (OSGE) (60 µg/ml H/H/C++ for 1 hr at 37° C.; Accurate Chemicals, Westbury, N.Y.), respectively. Cell monolayers were placed in the parallel-plate flow chamber and CHO-E/Mock cells were perfused into the chamber. After allowing the CHO-E or CHO-Mock cells to come in contact with the cell monolayers, the flow rate was adjusted to exert shear stress of 2.8 dynes/cm$^2$. The number of CHO-E/Mock cell rolling on each monolayer was measured in one frame of five independent fields under 10× magnification from multiple experiments. A minimum of 3 experiments was performed and results were expressed as the mean±standard deviation.

Alternatively, using freshly isolated human primary BMEC cultured as previously described (Rafii et al., 1994), BMEC from subcultures not older than passage 5 were seeded at 105cells/well in 6-well plates and, when 90-100% confluent, stimulated with IL-1α (40 U/ml) for 4 hr to upregulate the surface expression of E-selectin (expression of which was measured by flow cytometric analysis). Live cultures were then placed in the parallel-plate flow chamber and hematopoietic cells (107/ml in H/H/Ca++) were perfused into the chamber over the BMEC. Hematopoietic cell tethering and rolling was visualized at 2.8 dynes/cm$^2$. Non-IL-1α-activated BMEC and IL-1a-activated BMEC treated with 10 µg/ml anti-E-selectin moAb (clone 68-5H11) served as controls for assessing specificity of E-selectin-mediated adhesion. Cellular rolling was quantified and expressed as described above.

Utilizing Immobilized Immunoprecipitates.

CD44 was immunoprecipitated from untreated cell lysates or from cell lysates treated with N-glycosidase-F (0.8 U/ml) *Vibrio cholerae* neuraminidase (0.1 U/ml) or a-L-fucosidase (80 mU/ml), and PSGL-1 was immunoprecipitated from untreated cell lysates as previously described (Sackstein and Dimitroff, 2000; Dimitroff et al., 2000).

CD44 or PSGL-1 immunoprecipitates were spotted onto plastic petri dishes, fixed in 3% glutaraldehyde and incubated in 0.2M lysine to block unreactive aldehyde groups, and then non-specific binding was prevented by incubating in 100% FBS for 1 hr at RT. Fixed spots were also treated with *Vibrio cholerae* neuraminidase (0.1 U/ml assay medium), which was overlaid onto the spots and incubated at 37° C. for 1 hr. The protein dishes were placed in the parallel-plate flow chamber and CHO-E, CHO-P (CHO stably transfected with human cDNA encoding full length P-selectin), CHO-P cells treated with function blocking anti-P-selectin moAb (clone AK-4; Pharmingen) (10 µg/ml), CHO-E cells treated with function blocking anti-E-selectin Abs (10 µg/ml) (clone 68-5H1 1) or Mock transfectants were perfused into the chamber (2×10$^6$/ml H/H/Ca++) at a flow rate of 0.2 ml/min until the cells were in contact with the substrate. The flow rate was then increased to achieve a shear stress of 2.8 dynes/cm$^2$. The frequency of cells rolling per 100× magnification field was determined, and data were expressed as the mean±standard deviation of 8 fields visualized from a minimum of 3 experiments.

Figure 1B:
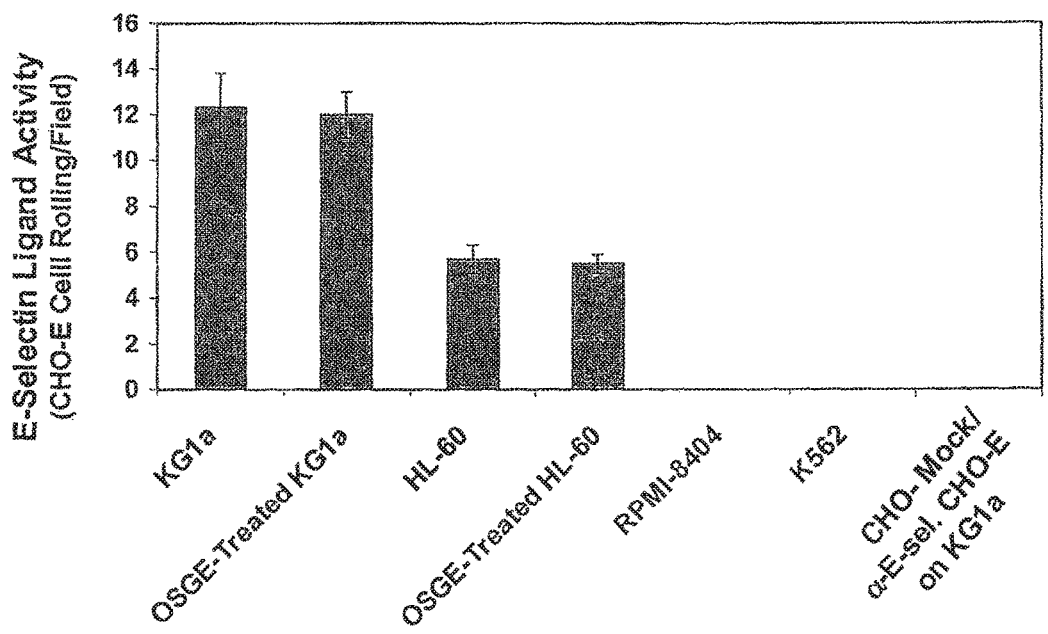

Tethering and rolling of Chinese hamster ovary cells expressing high levels of E-selectin (CHO-E) was observed on glutaraldehyde-fixed monolayers of KG1a and HL60 cells at 2.8 dynes/cm$^2$ (FIG. 1B). Mock-transfected CHO cells (CHO-mock) displayed no rolling. CHO-E cell rolling was 2-fold higher on KG1a cells than on HL60 cells and was completely inhibited by adding 5 mM EDTA to the assay medium, by preincubating CI-10-E cells with anti-E-selectin Abs or by pretreating KG1a or HL60 cells with *Vibrio cholerae* neuraminidase (which cleaves terminal sialic acids). There was no E-selectin ligand activity on cell lines RPMI-8402 and K562, whose membrane proteins did not contain HECA-452 epitopes. Surprisingly, the E-selectin ligand activity of KG1a and HL60 cells was not inhibited by incubating cells with HECA 452 at 50 µg/ml and was not abrogated by pretreatment with OSGE (FIG. 1B), though OSGE bioactivity was confirmed by the disappearance of the OSGE-sensitive epitope, QBEND-10, on KG1a CD34 as measured by flow cytometry.

To analyze the interaction between human HPCs and naturally expressed E-selectin on cells of physiologic importance, freshly isolated human BM microvascular endothelial cells (BMEC) were utilized. Under physiologic shear flow conditions, KG1a and HL60 cell rolling on live monolayers of IL-1a-activated BMECs were observed. Consistent with results from experiments using CHO-E cells to assess HPC E-selectin ligand activity, KG1a cells possessed a 4-fold greater capacity to roll on E-selectin on IL-1a-activated BMECs than HL60 cells, while RPMI-8402 and K562 cells possessed minimal E-selectin ligand activity (FIG. 2). KG1a and HL60 cellular E-selectin ligand activities were not observed on non-IL-1α-activated BMEC or on IL-1a-activated BMEC treated with a functional blocking anti-E-selectin moAb.

Example 3

Assessment of E-Selectin Glycoprotein Ligands from Human Hematopoetic Cells Using a Blot Rolling Assay To examine the E-selectin ligand activity of all HECA-452-reactive KG1a membrane proteins, the adhesive interactions under shear flow between selectin-expressing whole cells and proteins immobilized on Western blots was assessed (Dimitroff et al., 2000).

The blot rolling assay was performed as previously described (Dimitroff et al., 2000). Briefly, CHO-E, CHO—P or CHO-Mock transfectants were isolated as described above, washed twice in HBSS and suspended at 10$^7$/ml in HBSS/10 mM HEPES/2mMCaCl$_2$ (H/H/Ca++)/10% glycerol. Western blots of HPC membrane preparations stained with HECA-452 were rendered transparent by incubating them in H/H/Ca++/10% glycerol. The blots were then placed in the parallel-plate flow chamber, and CHO transfectants (2×10$^6$/ml) were perfused into the chamber. After allowing the cells to come in contact with the blotting membrane, the flow rate was adjusted to exert a shear stress of 3.8 dynes/cm$^2$. The viscosity of 10% glycerol adhesion assay medium was considered in the calculation of shear stress values. The number of cells rolling on and between each immunostained banding region was quantified under 100× magnification within each field of view on the video monitor using molecular weight markers (Kaleidoscope Molecular Weight Markers, Bio-Rad Lab.; See Blue® from Novex, Inc.) as guides to help align and visualize the apparent molecular weights of the proteins of interest. A minimum of 3 experiments was performed and results were expressed as the mean±SD of cell rolling/field at 100× magnification. Negative controls were prepared by either adding 5 mM EDTA to the CHO-E H/H assay buffer to chelate Ca++ required for binding, pretreating CHO-E cells with anti-E-selectin Abs (clone 68-5H1 1; 10 µg/ml) or by assessing the ability of CHO-Mock cells to interact with the immobilized proteins.

Figure 3A:
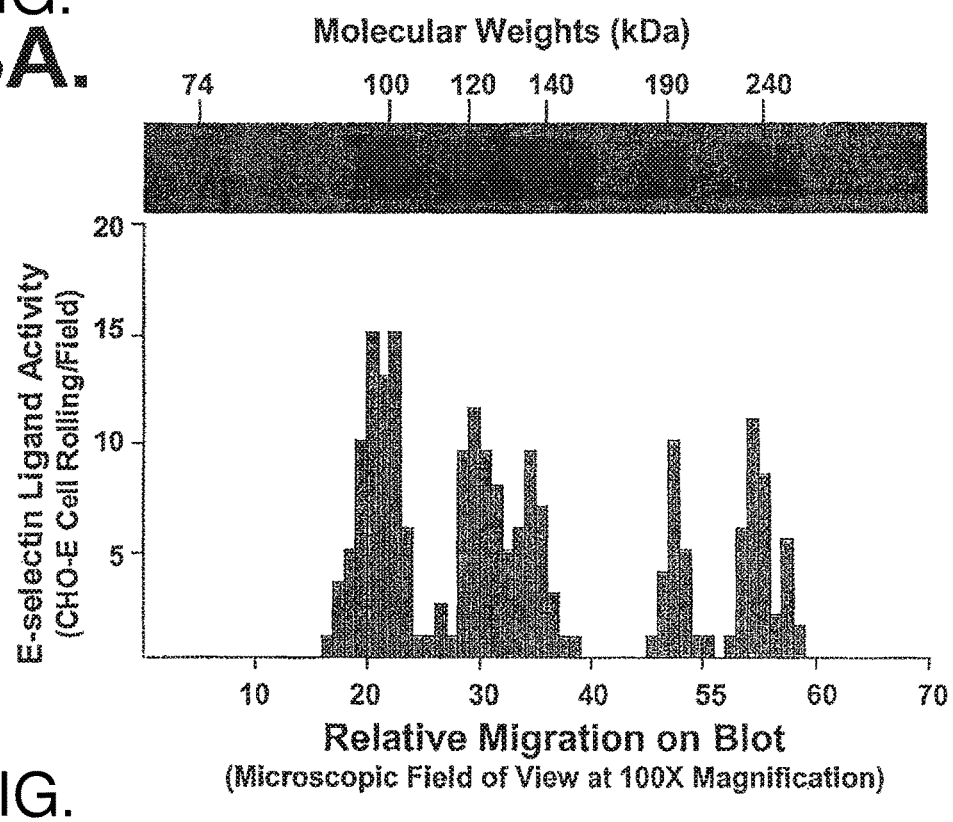
FIG. 3A is bar chart showing the results of a blot rolling assay of E-selectin ligand activity.
Figure 3B:
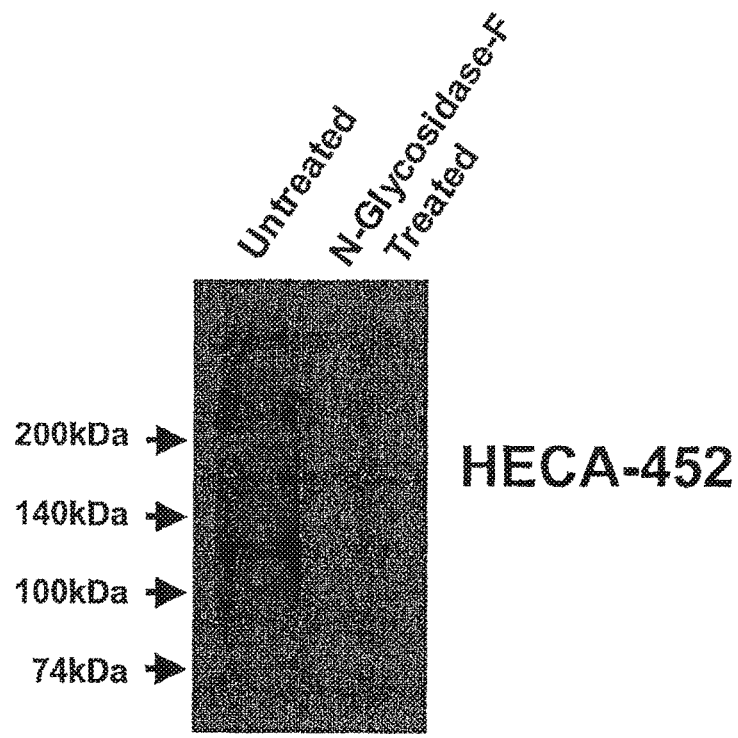
FIG. 3B is a photograph of a Western Blot showing the effect of N-glycosidase-F treatment on HECA-452 staining.

E-selectin ligand activity on HECA-452-stained bands at 100, 120, 140, 190 and 220 kDa, but not at 74 kDa (FIG. 3A) was observed. CHO-mock transfectants showed no interactions with any bands. Specificity for E-selectin was demonstrated by the abrogation of CHO-E cell rolling in the presence of either 5 mM EDTA or anti-E-selectin functional blocking Abs. On HL60 cells, CHO-E cell rolling was observed only over the broad 140 kDa HECA-452-immunostained band (i.e., PSGL-1/CLA). To determine whether E-selectin binding determinants reside on N-glycans, KG1a membrane protein was treated with N-glycosidase-F. De-N-glycosylated proteins were resolved by SDS-PAGE and analysed for HECA-452 reactivity and E-selectin ligand activity. N-glycosidase-F treatment markedly diminished HECA-452 staining (FIG. 3B) and also completely abolished CHO-E cell rolling on all proteins on the blot, indicating that all glycoprotein E-selectin binding determinants on KG 1 a cells are displayed exclusively on N-glycans.

Example 4

Identification and Characterization of HCELL

Figure 8:
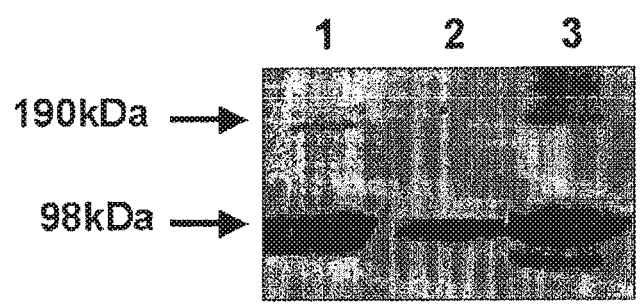
FIG. 8 is a photograph of a Western Blot showing the 98 kDa gel fragment from the third step of the 3-Step SDS-PAGE (6 to 9% bis/acrylamide) purification schema reactivity with either HECA-452 (0.4 µg/ml) or anti-CD44 moAbs (A3D8 or Hermes-1 (1 µg/ml)).

The expression of HECA-452 epitopes on the 98 kDa KG1a membrane protein after sequential excisions from SDS-PAGE gels of varying acrylamide percentage was followed. After each round of SDS-PAGE purification, the 98 kDa protein maintained its capacity to support lymphocyte rolling in the blot-based hydrodynamic flow assay. Following three rounds of SDS-PAGE purification, a faint HECA-452 stained band was detected at ~190 kDa in addition to the 98 kDa band, suggesting that some aggregation of the 98 kDa protein may have occurred çiuripg the isolation procedure. The 98 kDa Coomassie-blue-stained gel fragment was then submitted for mass spectrometry analysis of trypsin-digested peptide fragments. The primary peptide map matched that of the standard form of CD44 previously shown to be expressed on KG1a cells. Using monoclonal Abs against CD44 (mouse lgG A3D8, or rat lgG Hermes-1) along with HECA-452, we immunoblotted the purified 98 kDa band following the third gel isolation with either HECA-452, A3D8 or Hermes-1 (FIG. 8). Each antibody detected the 98 kDa species as well as the faint band at ~190 kDa, thought to represent aggregated protein. Correlation between the HECA-452 and anti-CD44 monoclonal antibodies indicated that the KG1 a glycoform of CD44 contains the HECA-452 carbohydrate determinant(s).

Figure 3C:
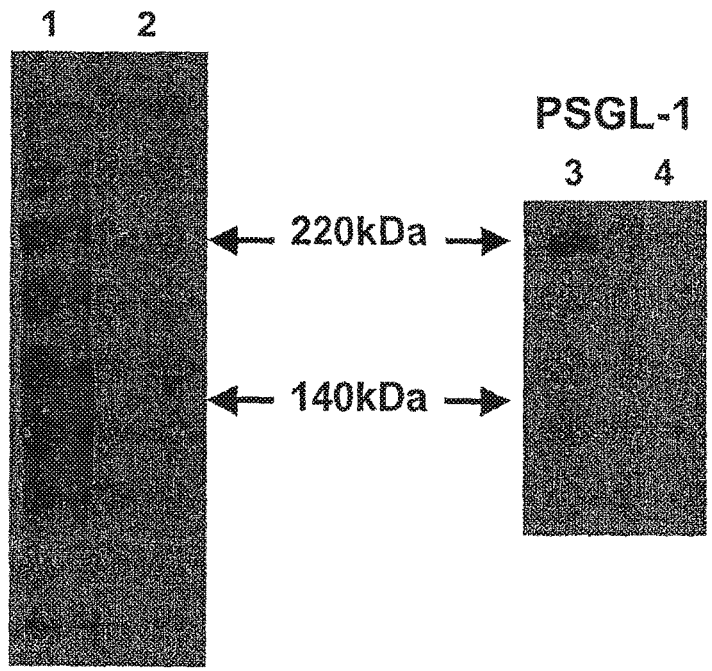
FIG. 3C is photograph of a Western Blot showing PSGL-1 expression on KG1a cells.

To distinguish KG1a cellular PSGL-1/CLA from the other HECA-452-reactive bands, blots of immunoaffinity-purified PSGL-1 and of total KG1a membrane protein were immunostained with either HECA-452 or anti-PSGL-1 (FIG. 3C). KG1a cells express both the monomer and dimer isoforms of PSGL-1, which represented the 140 and 220 kDa HECA-452-reactive proteins (FIG. 3C). Thus, the HECA-452 reactive bands at 100, 120 and 190 kDa, which support CHO-E cell rolling (FIG. 3A), corresponded to non-PSGL-1 proteins.

Figure 3D:
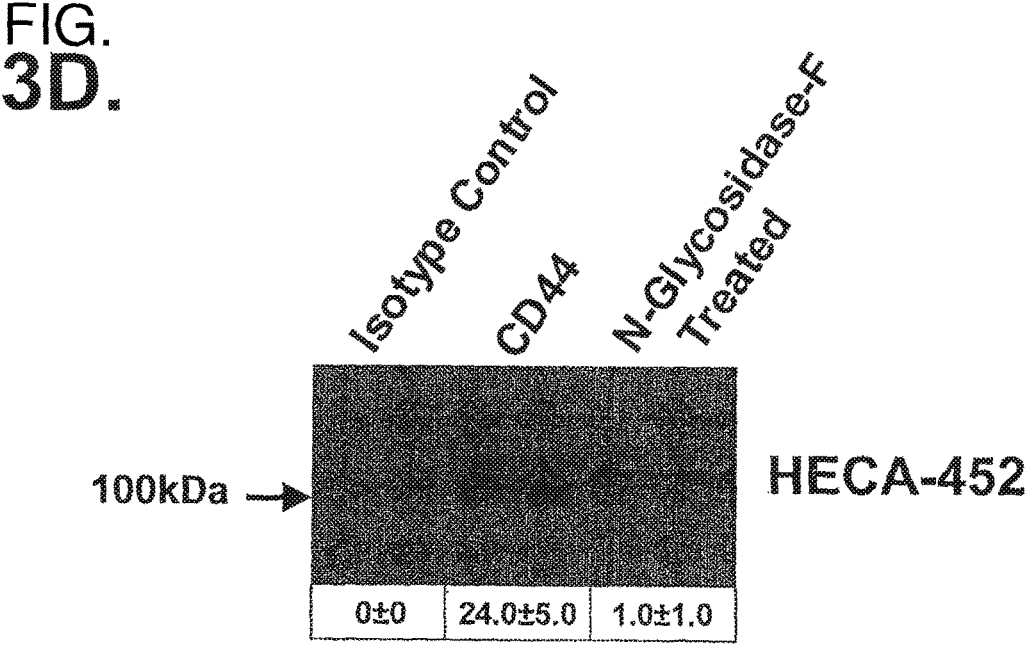
FIG. 3D is a photograph of a membrane of a Blot Rolling Assay showing the effect of N-glycosidase-F on E-selection ligand activity.

To determine whether N-glycan-specific modifications of CD44 confer the E-selectin ligand activity, immunoaffinity-purified CD44 from KG1a membrane proteins were tested for its capacity to serve as an E-selectin ligand in blot rolling assays. As shown in FIG. 3D, KG1a CD44 showed HECA-452 reactivity and possessed E-selectin ligand activity.

Treatment of CD44 with N-glycosidase-F markedly reduced HECA-452 reactivity and completely abrogated CHO-E cell rolling (FIG. 3D). Exhaustive immunoprecipitation of CD44 (3 rounds) resulted in the disappearance of stainable CD44 molecule at 100 kDa (Hermes-1 immunoblot and HECA-452 immunoblot) and of all E-selectin ligand activity at the 100 kDa and 190 kDa bands (FIGS. 4A and 4B). Moreover, there was a 55% decrement in E-selectin ligand activity at the 120 kDa band after three rounds of immunoprecipitation (FIG. 4B). Notably, there was no difference in HECA-452 staining or in E-selectin ligand activity of the 140 kDa monomer species of PSGL-1 after removal of CD44.

Figure 5A:
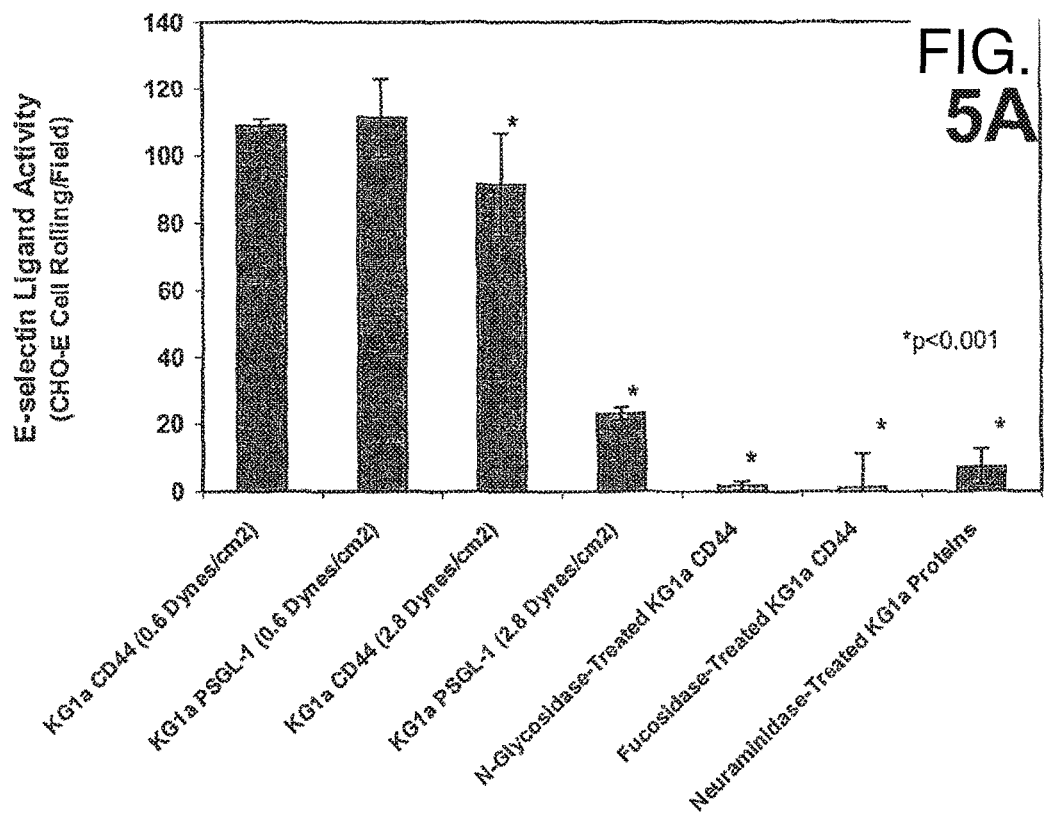
FIG. 5A is a bar chart of E-selectin-mediated CHO-E cell rolling. Rolling was observed at 2.8 dynes/cm$^2$ on KG1a CD44, but was significantly lower on KG1a PSGL-1 at 2.8 dynes/cm$^2$ ($p<0.001$). N-glycosidase-F- and a-L-fucosidase-treated KG1a CD44, and *Vibrio cholerae* neuraminidase treatment of KG1a membrane protein abrogated CHO-E cell rolling ($p<0.001$)
Figure 5B:
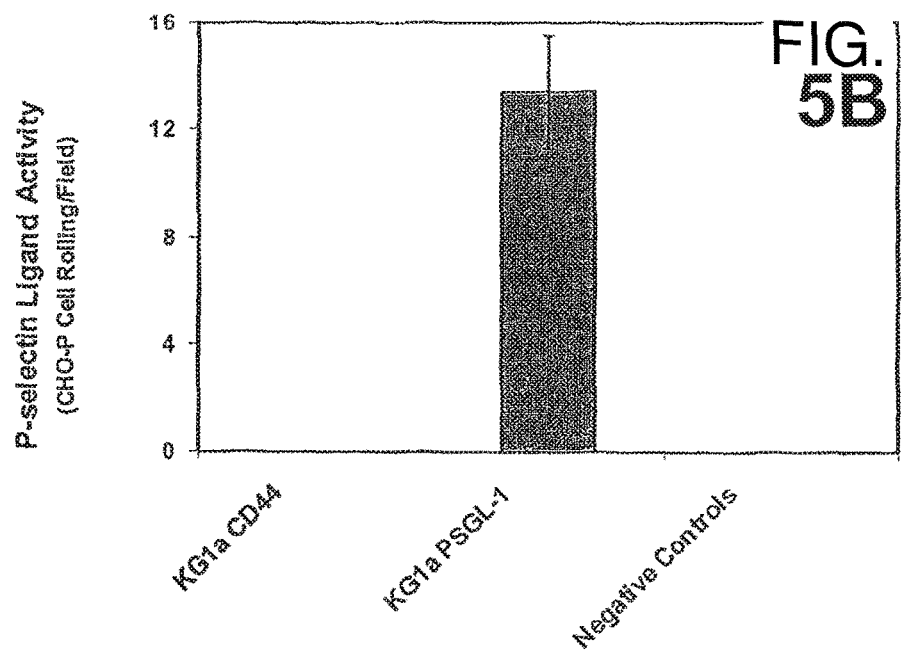
FIG. 5B is a bar chart showing CHO-P cell rolling. Rolling was observed on KG1a PSGL-1 but not on KG1a CD44 (2.8 dynes/cm$^2$). No rolling was observed on negative controls (CHO-Mock cells and CHO-P cells pretreated with function blocking anti-P-selectin moAb AK-4 (10 μg/ml)).

To further explore the E-selectin ligand activity of CD44, we directly immunoprecipitated CD44 from human hematopoietic cell lines and analyzed CHO-E cell binding in the parallel-plate flow chamber. While CD44 isolated from human hematopoietic cell lines HL60, K562 and RPMI 8402 did not support any CHO-E cell rolling, KG1a CD44 exhibited E-selectin ligand activity over a range of shear stress. Significantly greater CHO-E cell rolling was observed on untreated KG 1 a CD44 than on N-glycosidase-F-, on a-L-fucosidase treated KG 1 a CD44, on *Vibrio cholerae* neuraminidase-treated KG 1 a membrane protein or on isotype Ab immunoprecipitates (control) (FIG. 5A). In addition, compared with a molecular equivalent amount of immunoprecipitated KG1a PSGL-1, CD44 showed markedly greater E-selectin ligand activity at 2.8 dynes/cm$^2$ ($p<0.001$) (FIG. 5A). However, at a lower shear stress of 0.6 dynes/cm$^2$, CHO-E cell rolling on PSGL-1 was equivalent to that of CD44. These data suggest that PSGL-1 and CD44 have overlapping contributions to E-selectin binding at low shear stress, but that CD44 engagement with E-selectin predominates at higher physiologic shear stress. Of note, CHO cells transfected with P-selectin rolled on KG1a PSGL-1, but not on KG1a CD44 (Figure SB), indicating that CD44 is not a P-selectin ligand (FIG. 5B). In all experiments, negative control CHO cells (CHO-mock transfectants and CHO-E or CHO-P cells treated with respective function blocking anti-B- or P-selectin moAbs) did not tether and roll on any proteins.

Figure 6A:
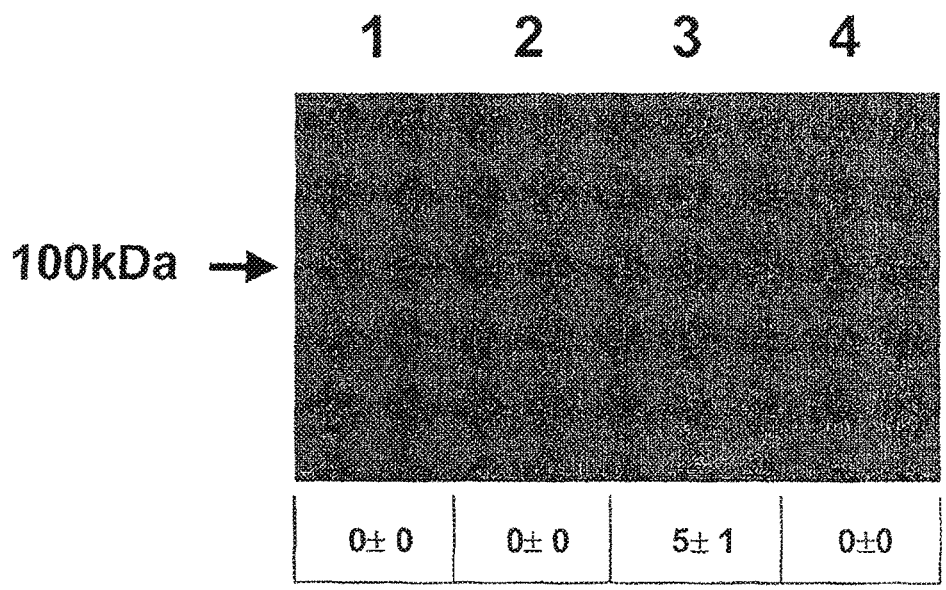
FIG. 6A is a photograph of a membrane of a Blot Rolling Assay showing HCELL activity of various hematopoietic cells. (1) Human BM mononuclear cells (10$^8$ cells), (2) CD34−/lineage+ cells (10$^7$ cells), (3) CD34+/lineage− cells (10$^7$ cells), (4) CD34−/lineage+ cells (10$^8$ cells).

To determine whether CD44 naturally-expressed on normal human HPCs functions as an E-selectin ligand, we investigated the distribution of HECA-452-reactivity and E-selectin ligand activity of CD44 expressed on early CD34+ cells and more mature (CD34–/lineage+) human BM cells (including populations enriched for monocytes (CD14+), granulocytes (CD 15+), and lymphocytes (B cells (CD19+) and T cells (CD3+)). Surprisingly, although SDS-PAGE of Hermes-1 immunoprecipitates of KG1a cells reveals three bands (100, 120 and 190 kDa), only a single 100 kDa CD44 was immunoprecipitated from both CD34+ and lineage+/CD34– cells, and only CD44 from CD34+ cells stained with HECA-452 and functioned as an E-selectin ligand (FIG. 6A). Similar results were obtained whether CD34+ cells were enriched by negative selection or by positive selection. Even when 10-fold excess lineage+ cell membrane protein was utilized for CD44 immunoprecipitation, there was still neither HECA-452-staining of CD44 nor E-selectin ligand activity of CD44 (FIG. 6A). Moreover, immobilized on plastic; CD44 immunoprecipitated only from CD34+/CD44+ cells supported CHO-E cell rolling whereas immunoprecipitated CD44 from CD34– cells did not possess any E-selectin ligand activity.

Figure 6B:
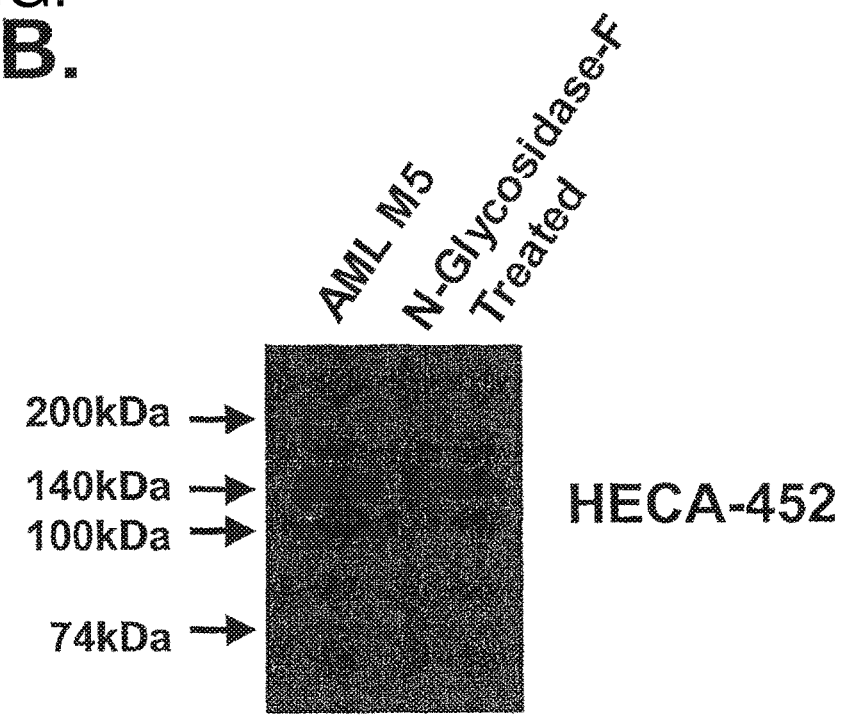
FIG. 6B is a photograph of a Western Blot illustrating the effect of N-glycosidase-F treatment on HECA-452 activity on circulating blasts from adult myelogenous leukemia (AML).
Figure 6C:
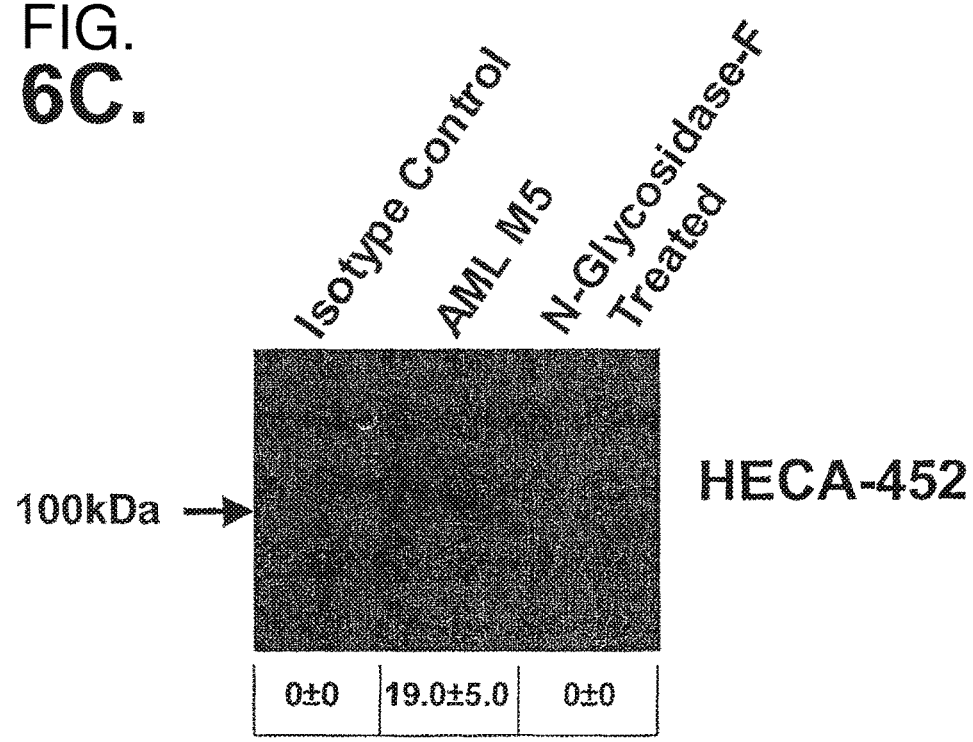
FIG. 6C is a photograph of a membrane showing blot rolling assay results of AML (M5) membrane protein (50 μg) immunoprecipitated with isotype control or with Hermes-1 moAb, and of N-glycosidase-F treated Hermes-1 immunoprecipitates.
Figure 6D:
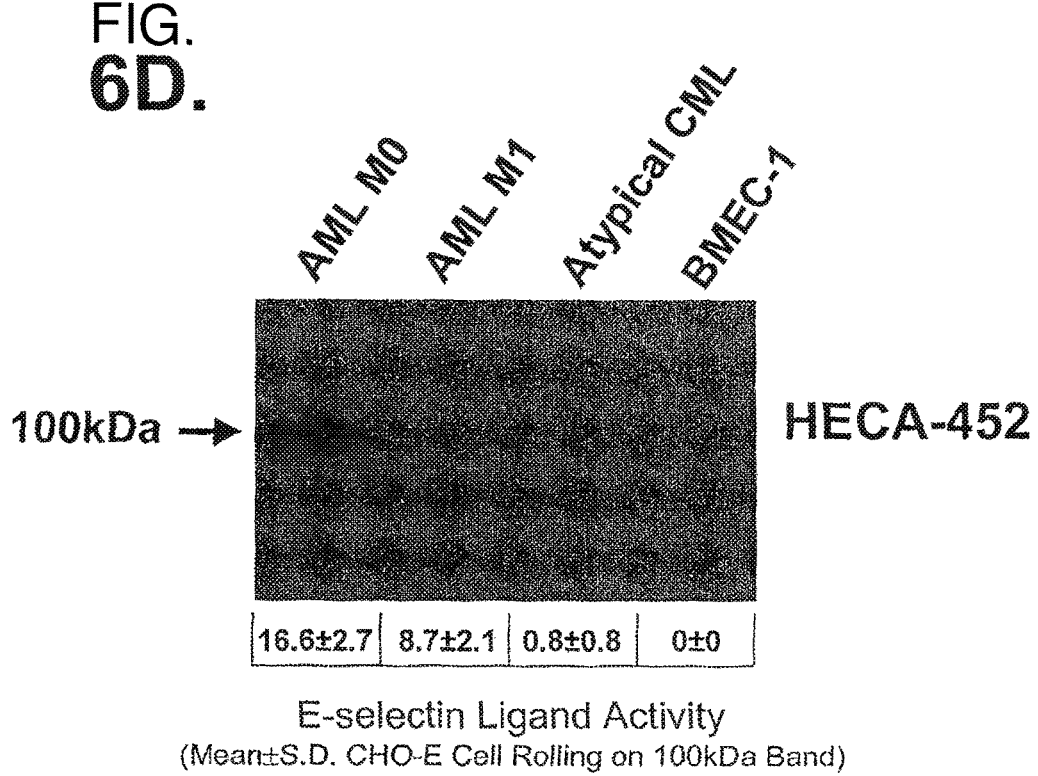
FIG. 6D is a photograph showing HECA-452 staining of immunoprecipitated CD44 from membrane preparations (50 μg) of an AML (M0), AML (M1) and atypical CIVIL (brc/abl), and of human BM endothelial cell line (BMEC-1, 100 μg total protein) that were evaluated for E-selectin ligand activity. E-selectin ligand activity correlates with intensity of HECA-452 staining of 100 kDa band.
Figure 6E:
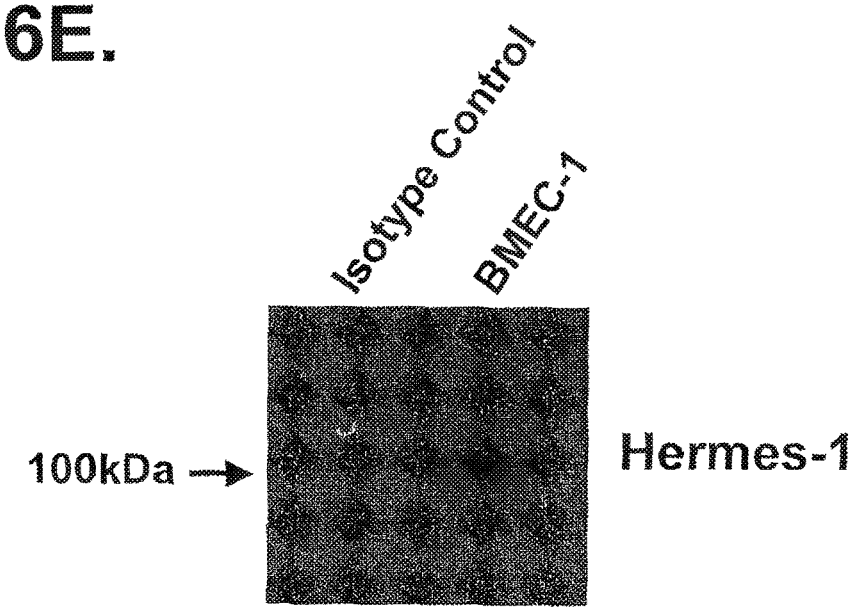
FIG. 6E is photograph of a Western Blot showing CD44 expression of BMEC-1.

To further analyze the expression and structure of HECA-452-reactive CD44 on human hematopoietic cells, expression of HCELL on native leukemic blasts was evaluated. Four major HECA-452 stained bands were detected (74, 100, 140 and 190 kDa) from leukemic blasts of an acute myelogenous leukemia (AML) (subtype M5) (FIG. 6B). HECA-452-staining was completely eliminated in the 100 kDa region following N-glycosidase-F treatment, while the 74 and 140 kDa bands had persistent staining and the 100 kDa band stained at an apparently reduced molecular weight (FIG. 6B). When immunoprecipitated CD44 from AML (M5) membrane protein was treated with N-glycosidase-F, the HECA-452-reactivity as well as the E-selectin ligand activity was completely abolished (FIG. 6C). Similar to immunoprecipitated KG1a CD44, AML (M5) CD44 displayed a minor isoform at 120 kDa detected by HECA-452, but the major band and biologically active protein was the 100 kDa CD44 isoform. CD44 was also immunoprecipitated from blasts of an undifferentiated AML (MO), an AML without maturation (M1) and an atypical chronic myelogenous leukemia (CML) (bcr/abl-). Of note, expression of the HECA-452-reactive epitopes on immunoprecipitated CD44 directly correlated with the ability to support CHO-E cell rolling (FIG. 6D). The expression of CD44 (Hermes-1 moAb) on these leukemias was equivalent (>90% positive cell staining by flow cytometry), further indicating that the ability to interact with E-selectin was dependent on the elaboration of HECA-452-reactive glycosylations. Moreover, since CD44 is also expressed on non-hematopoietic cells, we analyzed CD44 expressed on the human BM endothelial cell line BMEC-I. Though BMEC-1 expressed high levels of CD44 (FIG. 6E), CD44 from these cells was not HECA-4S2-reactive and did not possess any E-selectin ligand activity (FIG. 6D).

Example 5

Assessment of L-Selectin Glycoprotein Ligands from Human Hematopoetic Cells Using a Blot Rolling Assay To examine the L-selectin ligand activity of all HECA-452-reactive KG1a membrane glycoproteins, the adhesive interaction under shear flow between selectin-expressing while cells and protein immobilized on Western Blots was assessed.

L-selectin-expressing lymphocytes were isolated as previously described (Oxley, S. M. & Sackstein, R. (1994). Blood. 84:3299-3306; Sackstein, R., Fu, L. and Allen, K. L. (1997) Blood. 89:2773-2781), washed twice in HBSS and suspended at $2 \times 10^7$/ml in HBSS/10 mM HEPES/2mMCaCl$_2$ (H/H/Ca$^{++}$)/10% glycerol. Cell lysate material is separated by SDS-PAGE and transferred to PVDF under standard blotting conditions. Western blots of KG1a membrane preparations stained with HECA-452, A3D8 or Hermes-1 were rendered transparent by incubating them in H/H/Ca$^{++}$/10% glycerol. To study L-selectin-mediated adhesive interactions, the blots were placed in the parallel plate flow chamber and lymphocytes were perfused into the chamber at a shear force of 2.3 dynes/cm$^2$ and cellular adhesive interactions are observed by video microscopy and analyzed in real time.

The number of lymphocytes rolling on and between each immunostained banding region was quantified from five independent fields under 200× magnification on the video monitor using molecular weight markers as guides to help align and visualize the proteins of interest. A minimum of 3 experiments were performed, and results were expressed as the mean of cell rolling/field. Negative controls were prepared by either adding 5 mM EDTA to the lymphocyte H/H assay buffer to chelate Ca++ required for binding, by using lymphocytes treated with PMA (50 ng/ml, which induces the cleavage of L-selectin (Oxley, S. M. & Sackstein, R. (1994). Blood. 84:3299-3306)), or by treating the lymphocytes with functional blocking anti-L-selectin MoAbs (10 μg/ml) to verify the sole contribution of L-selectin.

Figure 7A:
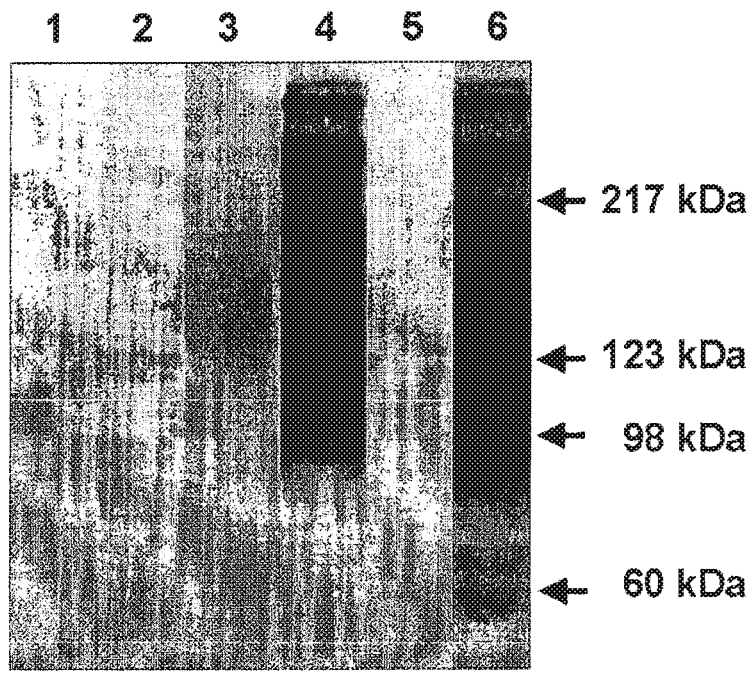
FIG. 7A is a photograph of a Western blot of HECA-452-reactive membrane proteins (30 µg/lane) from human leukemia cell lines K562 (lane 1), RPMI-8402 (lane 2), HL-60 (lane 3), KG1a (lane 4), neuraminidase-treated KG1a (lane 5), and OSGE-treated KG1a (lane 6).
Figure 7B:
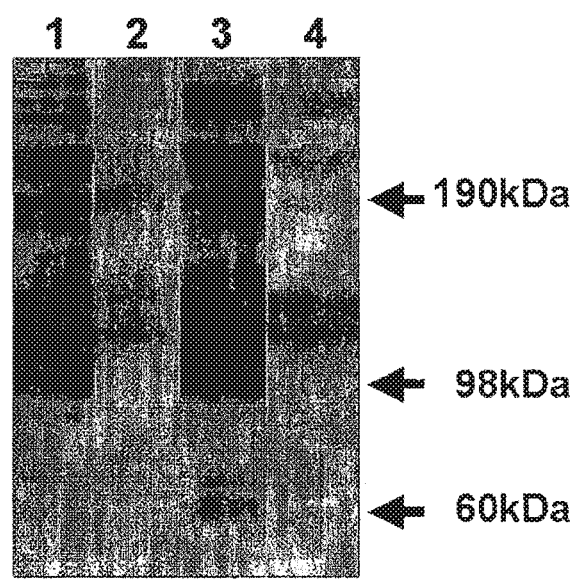
FIG. 7B is a photograph of a Western blot showing the re-expression of HECA-452-reactive proteins on KG1a whole cells after neuraminidase and then tunicamycin treatment. Lanes: 1, untreated; 2, neuraminidase; 3, neuraminidase then 24-h DMSO recovery; and 4, neuraminidase then 24-h tunicamycin recovery.
Figure 7C:
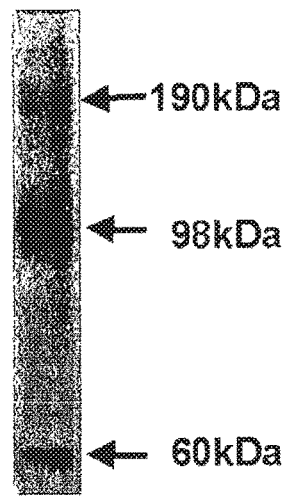
FIG. 7C is a photograph of an autoradiograph of KG1a membrane proteins metabolically radiolabeled with 2-[$^3$H]-mannose resolved on reducing 6% SDS-PAGE.
Figure 7D:
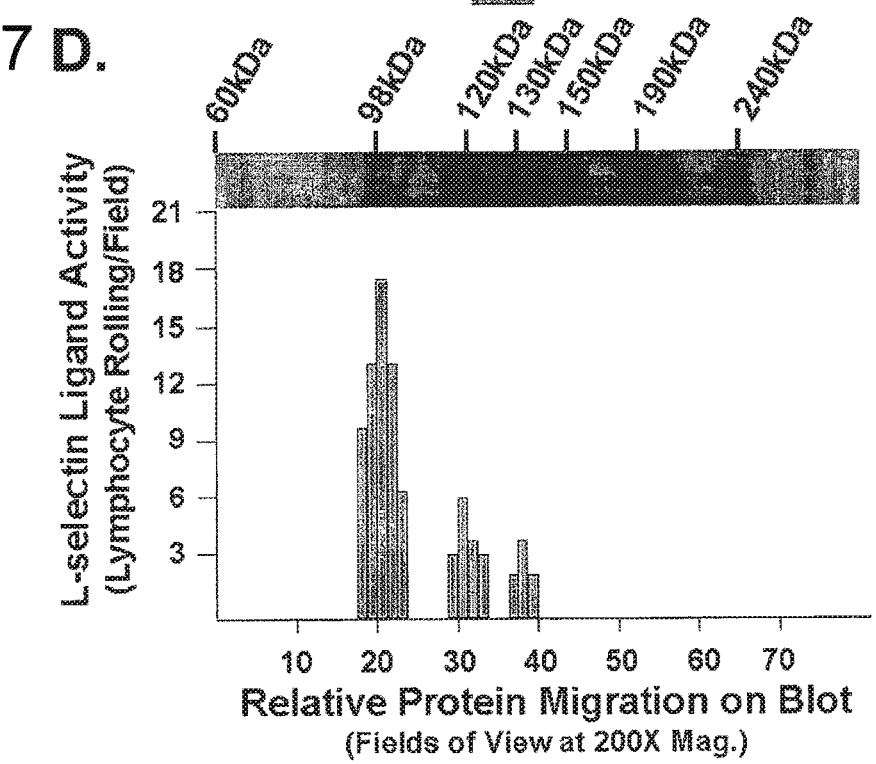
FIG. 7D is a bar chart showing L-selectin-dependent, lymphocyte tethering and rolling on blotting membrane under hydrodynamic flow conditions (2.3 dynes/cm$^2$) over the 98, 120 and 130 kDa HECA-452-bearing KG1a proteins.

Western blots of KG1a membrane proteins that were immunostained with HECA-452. (Oxley, S. M. & Sackstein, R. (1994). Blood. 84:3299-3306; Sackstein, R., Fu, L. and Allen, K. L. (1997). Blood. 89:2773-2781) were perfused over the blots to assess for L-selectin ligand activity on resolved immunostained bands. Shear-dependent lymphocyte tethering and rolling (at shear force of 2.3 dynes/cm$^2$) on HECA-452-stained bands of 98, 120 and 130 kDa that was L-selectin-dependent was observed. To verify that the shear-dependent lymphocyte tethering and rolling was L-selectin dependent, the assay was also performed in the presence of 5 mM EDTA, and by pretreating the lymphocytes with either anti-L-selectin blocking monoclonal Abs or PMA (FIG. 7 D). There was no L-selectin ligand activity displayed by any non-HECA-452-stained areas of the blot (FIG. 7 D). The HECA-452-stained 98 kDa band displayed the greatest L-selectin ligand activity (as much as 6-fold higher compared to other bands), and this band is also the major N-glycan-bearing protein expressed on KG1a cells (FIG. 7C). Several of the HECA-452 reactive KG 1 a bands did not possess L-selectin ligand activity suggesting that the structural modification(s) associated with these HECA-452 reactive proteins was not sufficient for L-selectin ligand activity. L-selectin ligand activity was absent on Western blots of HL60, K562 and RPMI 8402 membrane proteins, despite evidence of HECA-452-reactive bands. HECA-452-staining did not interfere with L-selectin-mediated lymphocyte adherence to the relevant immobilized KG1a proteins in hydrodynamic flow assays of Western blots.

Example 6

L-Selectin Ligand Activity of Immunoprecipitated KG1a CD44 (HCELL)

Figure 9:
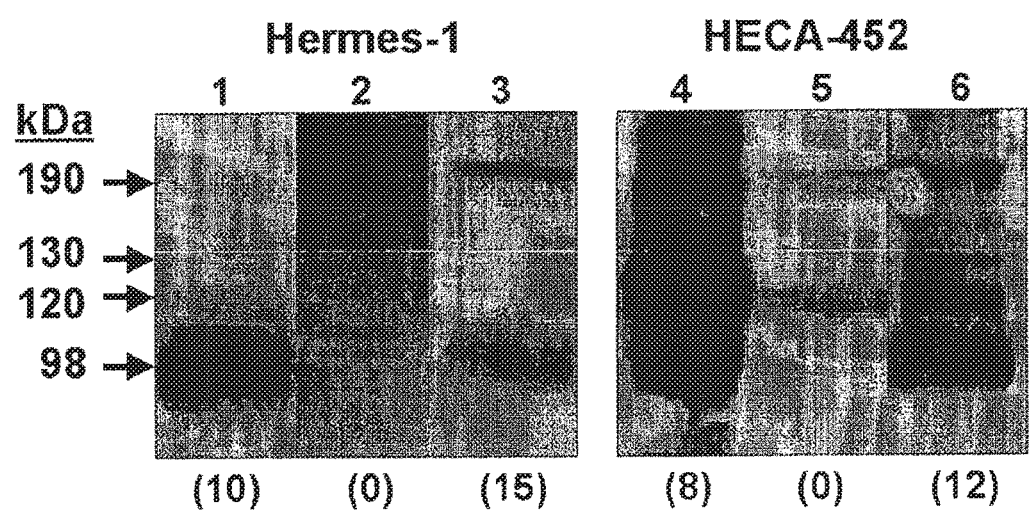
FIG. 9 is a photograph of a membrane showing L-selectin mediated blot rolling assay results of immunoprecipitated KG 1 a CD44 immunostained with either Hermes-1 (left) or HECA-452 (right).

Immunoblots of KG1a CD44 in total KG1a cell lysate using Hermes-1 moAb showed a 98 kDa band, as well as 120 and 130 kDa bands which may reflect isoforms that were previously designated as CD44R2 and CD44R1, respectively (FIG. 9) (Dougherty, G. J., Lansdorp, P. M., Cooper, D. L. & Humphries, R. K. (1991). *J. Exp. Med.* 174:1-5). A faint signal at 190 kDa that was detected by Hermes-1 and A3D8, which may reflect a chondroitin sulfate-modified form of CD44 (FIG. 9) (Jalkanen, S. T., Jalkanen, M., Bargatze, R., Tammi, M., & Butcher, E. C. (1988). *J. Immunol.* 141:1615-1623). To directly analyze whether this CD44 glycoform exhibited L-selectin ligand activity, KG1aCD44 from KG1 a cells was immunoprecipitated with Hermes-1 moAb and then performed blot rolling assays on immunoblots of CD44 stained with either Hermes-1 or HECA-452. Surprisingly, Hermes-1-immunoprecipitated CD44 that was then immunoblotted with Hermes-1 displayed only the 98 kDa and 190 kDa species, but not the 120 and 130 kDa species. On the other hand, Hermes-1 immunoprecipitated CD44 that was immunoblotted with HECA-452 illustrated not only the 98 kDa species, but also 120, 130 and 190 kDa species (FIG. 9). In all cases though, only the HECA-452-reactive, Hermes-1-reactive 98 kDa protein supported L-selectin ligand interactions (FIG. 9).

Example 7

Dependence of N-Glycosylation for L-Selectin Ligand Activity and for Immunodetection by HECA-452

Figures 10A, 10B:
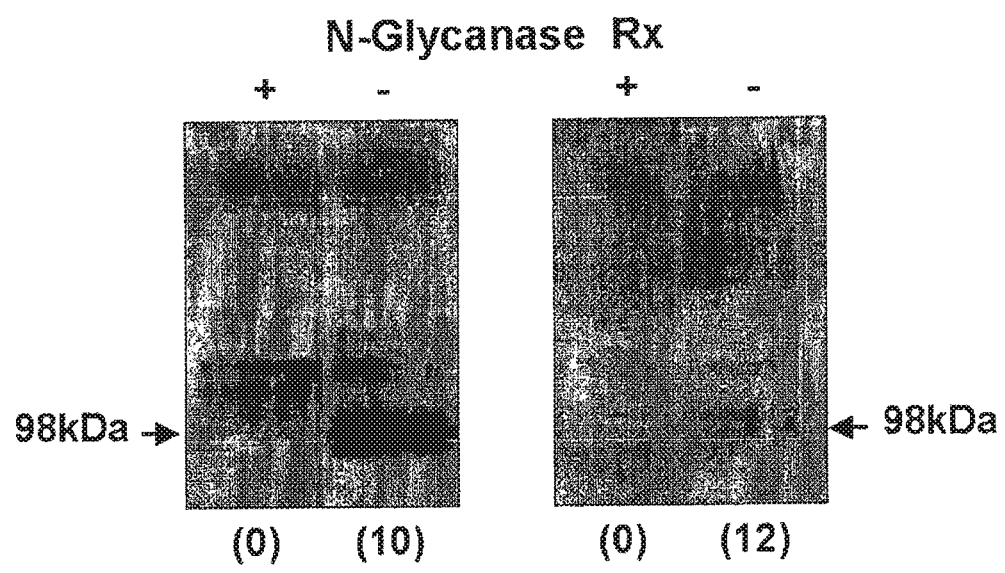
FIG. 10A is a photograph of a membrane showing blot rolling assay results of treatment with N-glycosidase-F on L-selectin ligand activity of immunoprecipitated CD44 from KG1a cells.
FIG. 10B is a photograph of a membrane showing blot rolling assay results of treatment with N-glycosidase-F on L-selectin ligand activity of immunoprecipitated CD44 from AML (M5) blasts.

To examine the dependence of L-selectin ligand activity on N-glycosylation, immunoprecipitation of KG1a CD44 with Hermes-1 was also performed on KG1a membrane proteins pretreated with N-glycosidase-F. As depicted in FIG. 10A, N-glycosidase-F treatment completely eliminated HECA-452 staining of the 98 kDa species and abolished all L-selectin-mediated lymphocyte tethering and rolling on the blot. Ligand activity over all molecular weight ranges in the N-glycosidase-F-treated sample was assessed and some change in molecular weight with de-N-glycosylation of the glycoprotein was observed. Following de-N-glycosylation, there were no bands demonstrating L-selectin ligand activity.

To further analyze the L-selectin ligand activity of CD44, we performed Stamper-Woodruff assays using immunoprecipitated CD44 or isotype control (rat lgG) immunoprecipitates of KG1 a cells that was spotted onto glass slides as described (Sackstein, R. & Dimitroff, C. J. (2000). Blood. 96, 2765-2774). Assays utilizing Vibrio cholerae neuraminidase-treated CD44, anti-L-selectin moAb (HRL-1 for rat lymphocytes; LAM1-3 for human lymphocytes)-treated lymphocytes, or 5 mM EDTA co-incubation served as negative controls. Immunoprecipitated, KG1a CD44 supported L-selectin-mediated lymphocyte adherence (362±15 bound cells/field, 5 fields counted, 3 slides per experiments, 2 experiments), whereas no binding was observed with isotype control immunoprecipitate or with neuraminidase-treated immunoprecipitated KG1a CD44 or EDTA/anti-L-selectin Ab treatments (<10 cells bound cells/field). HECA-452 did not block lymphocyte adherence to isolated KG1a CD44, intact KG1a cells or to KG1a membrane proteins, despite input concentrations as high as 100 μg/ml. These results corroborated and confirmed the data from the parallel-plate flow chamber studies described above.

Example 8

KG1a CD44 (HCELL) Functions as an L-Selectin Ligand in Freshly Isolated Human Hematopoietic Cells HCELL activity within normal marrow mononuclear cells was examined by Stamper-Woodruff assays of sorted populations of CD34+/CD44+, CD34+/CD44−, CD34−CD44+ and CD34−CD44− cells. HCELL activity was absent on all CD44− subsets, but was present on >80% of CD34+/CD44+ cells and only ~1% of CD34-CD44+ cells. Because biochemical studies of CD44 on normal human CD34+ bone marrow cells were limited by the difficulties in acquiring sufficient quantities of cells for such analysis, the HCELL activity of CD44 isolated from blasts known to express HCELL activity was examined (Sackstein, R. & Dimitroff, C. J. (2000). Blood. 96, 2765-2774). Blasts from eleven leukemias: nine myelocytic (two undifferentiated. (MO), two without maturation (M1), one with maturation (M2), two myelomonocytic (M4) and two monocytic (M5)), one acute lymphocytic (pre-B) and one biphenotypic were analyzed. With exception of one MO, all leukemic blasts displayed HCELL activity. The L-selectin ligand activity of CD44 isolated from blasts of five of leukemias described above: one MO shown to lack HCELL activity and the others with HCELL activity (the biphenotypic leukemia, the other MO, an M4, and an M5) was analyzed. In blot rolling assays of total membrane protein, lymphocyte tethering and rolling was observed over a 98 kDa band in all leukemias expressing HCELL, but no rolling was observed on any membrane protein from the MO lacking HCLL activity. CD44 was immunoprecipitated from each of these cells, and, similar to CD44 from KG1a cells, the predominant isoform was a 98 kDa species. A representative example of these data, from an M4 leukemia, is shown in FIG. 10B. The requirement of N-glycosylated structures on CD44 for HECA-452 reactivity and L-selectin ligand activity was verified by pretreating the leukemia membrane proteins with N-glycosidase-F (FIG. 10B). Conversely, though the HCELL(−) MO blasts possessed equivalent CD44 to that of the HCELL(+) leukemia specimens (as determined by flow cytometry and by Western blotting using Hermes-1 Ab,), CD44 from these cells was not HECA-452-reactive and did not exhibit L-selectin ligand activity. Taken together, these observations indicated that the CD44 glycoform exhibiting HCELL activity was not a unique feature of the KG1a cell line, but represented a physiologic modification of CD44 present in blasts of some subsets of human leukemias. These observations added further evidence that component of N-glycans expressed on CD44.

Example 9

L-Selectin Ligand Activity of KG1a CD44 is Independent of Sulfation

Figure 11A:
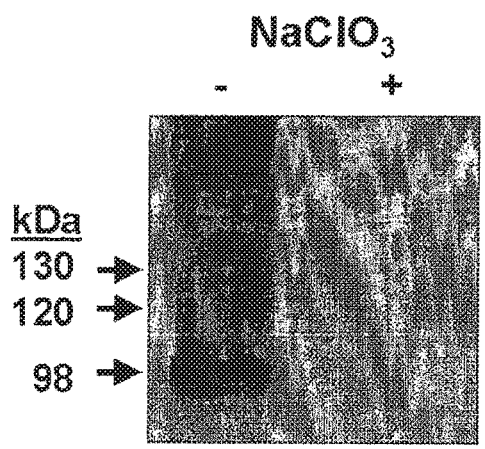
FIG. 11A is a photograph of an autoradiogram of immunoprecipitated CD44 from non-chlorate- and chlorate-treated KG1a cells radiolabeled with [$^{35}$S]SO$_4$

To determine if CD44 on KG1a cells is sulfated, KG1a cell cultures were metabolically labeled with [$^{35}$S]-SO4. CD44 immunoprecipitated from these cells was indeed sulfated (FIG. 11 A). To test whether sulfation was critical for L-selectin ligand activity of CD44, KG1a cells were pretreated with 0.1% bromelain, a protease that eliminates all KG1a HCLL activity (Sackstein, R. & Dimitroff, C. J. (2000). Blood. 96, 2765-2774) and also removes CD44 from the cell surface (Hale, L. P. & Haynes, B. F. (1992). J. Immunol 149:3809-3816). Following bromelain digestion of KG1a, re-expression of HCELL requires de novo protein synthesis, and protein synthesized in the presence of chlorate (a metabolic inhibitor of both protein and carbohydrate sulfation) is non-sulfated (Sackstein, R., Fu, L. and Allen, K. L. (1997). Blood. 89:2773-2781). Therefore, KG1a was treated with bromelain and confirmed removal of CD44 by flow cytometry. The KG1a cells were cultured in the absence or presence of 10 mM sodium chlorate for 24 hr and metabolically radiolabeled the cells for the last 8 hr of incubation with [$^{35}$S]-SO4 in sulfate-deficient CRCM-30 medium. As illustrated in FIG. 11A, the incorporation of [$^{35}$S]-SO4 into immunoprecipitable CD44 (Hermes-1) was completely inhibited in chlorate-treated cells. This effect of chlorate was specific for sulfate incorporation and not a general inhibition of CD44 protein synthesis, as [$^{35}$S]-methionine/cysteine metabolic radioloabeling of CD44 was identical in chlorate- and non-chlorate-treated cell populations.

Figure 11B:
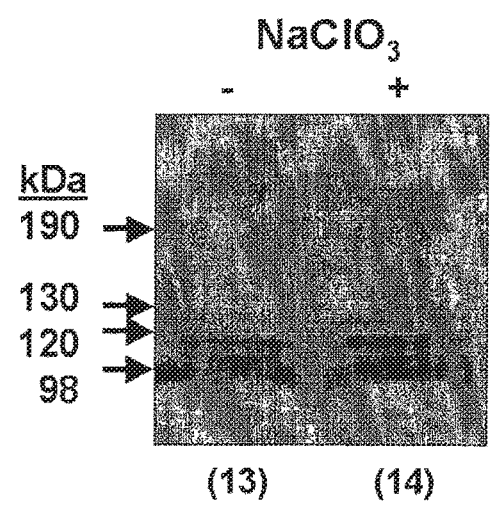
FIG. 11B is a photograph of HECA-452 immunoblots of immunoprecipitated KG1a CD44 from chlorate (+) and non-chlorate treated (−)KG1a cells. L-selectin ligand activity (mean number of lymphocytes/200× mag. field/5 fields) was equivalent in sulfated and non-sulfated (chlorate treated) KG1a CD44.

Blot rolling assays were then performed on CD44 immunoprecipitated from control and chlorate-treated cells. The L-selectin ligand activity of sulfated and non-sulfated CD44 (FIG. 11 B). These experimental data confirmed the results of our previous studies that demonstrate the sulfation-independence of HCLL activity (Sackstein, R., Fu, L. and Allen, K. L. (1997). Blood. 89:2773-2781). Surprisingly, recognition of sulfate-free CD44 with HECA-452 was not prevented (FIG. 11B). These data show that sulfation was not a critical feature of the epitope on KG1a CD44 recognized by the HECA-452 monoclonal antibody.

Example 10

Differential L-Selectin Bonding Activities of Human Hematopoietic Cell L-Selectin Ligands, HCELL and PSGL-1

A. General Methods
Cell, Antibodies and Enzymes

Human hematopoietic cell lines KG1a (myelocytic leukemic, HCELL+/PSGL-1+), HL60 (promyelocytic leukemia, HCELL−/PSGL-1+), RPMI 8402 (lymphocytic leukemia, HCELL−/PSGL-1+) and K562 (erythrocytic leukemia, HCELL−/PSGL-1−), and circulating blasts from a de novo acute myeloid leukemia (AML) without maturation (M1) (HCELL$^+$/PSGL-1$^+$) were maintained in RPMI-1640/10% FBS/1% Penicillin-Streptomycin (Life Technologies, Inc.). Chinese hamster ovary (CHO) cells transfected with full length cDNA encoding P-selectin (CHO-P; clone E4I) and CHO-empty vector (CHO-Mock) were obtained from Robert C. Fuhlbrigge (Harvard Medical School), and maintained in MEW 10% FBS/1% Penicillin/Streptomycin (Life Technologies, Inc.) and HAM's F-12/5 mM Glutamine/5% FCS/1% Penicillin/Streptomycin. Human lymphocytes (PBMC) were prepared from whole blood as previously described (Oxley, S. M. and Sackstein, R. (1994) Blood 84(10), 3299-3306). Rat thoracic duct lymphocytes (TDL) that express high levels of L-selectin, which functions identically to human lymphocyte L-selectin, were obtained by cannulation of the rat thoracic duct as previously described (Oxley, S. M. and Sackstein, R. (1994) Blood 84(10), 3299-3306). Human neutrophils were prepared from peripheral whole blood, collected in acid citrate buffer/0.6% dextran and red cells were allowed to separate under gravity for 30 min. at RT. Leukocyte rich plasma was diluted 1:1 with PBS without Ca$^{++}$/Mg$^{++}$ and granulocytes were pelleted by Ficoll-Hypaque (1.077-1.0800 g/ml) density gradient centrifugation. To lyse residual red cells in cell pellets, cells were exposed to hypotonic solution for 30 sec. and then neutralized with hypertonic NaCl. This procedure resulted in a >98% enrichment of granulocytes. Circulating leukemic blasts from a patient with an acute myeloid leukemia without maturation (M1) were isolated by Ficoll-Hypaque (1.077-1.0800 g/ml) density gradient centrifugation from peripheral blood.

Anti-PSGL-1 monoclonal Ab PL-1 and PL-2, FITC-anti-CD45, and anti-CD34 QBEND Abs were purchased from Coulter-Immunotech, Marseilles, France. Anti-PSGL-1 monoclonal Ab PSL-275 was a gift from Dr. Ray Camphausen (Genetics Institute, Cambridge, Mass.). Anti-sialyl Lewis X monoclonal Ab (CSLEX-1), anti-CD44 (clone L178) and anti-CD43 antibodies were purchased from Becton Dickinson, San Jose, Calif. Anti-CD44 moAb Hermes-1 (rat IgG2a) was originally characterized by Jalkanen et al. (Jalkanen, S. T., Bargatze, R. F., Herron, L. R. and Butcher, E. C. (1986) Eur. J. Immunol. 16, 1195-1202). Rat monoclonal Ab anti-human CLA (HECA-452), anti-rat L-selectin (HRL-1; ligand blocking antibody), anti-human P-selectin (clone AK-4) and anti-human L-selectin (LAM1-3) were purchased from Pharmingen, San Diego, Calif. All fluorochrome-conjugated secondary antibodies and isotype controls were obtained from Zymed, San Francisco, Calif.

OSGE was purchased from Accurate Chemicals, Westbury, N.Y., and *Vibrio cholera* neuraminidase and N-glycosidase-F was obtained from Roche Molecular Biochemicals, Indianapolis, Ind. Cobra venom metalloprotease, mocarhagin (Spertini, O., Cordey, A. S., Monai, N., Giuffre, L. and Schapira, M. (1996) J. Cell Biol. 135(2), 523-531; De Luca, M., Dunlop, L. C., Andrews, R. K., Flannery, J. V., Ettling, R., Cumming, D. A., Veldman G. M. and Berndt, M. C. (1995) J. Biol. Chem. 270(45), 26734-26737), was a gift from Dr. Ray Camphausen (Genetics Institute, Cambridge, Mass.). The metabolic inhibitor, tunicamycin, and all other chemicals were purchased from Sigma, Inc. (St. Louis, Mo.).

Flow Cytometric Analysis.

Flow cytometric analysis was performed on human HCs utilizing both direct and indirect immunofluorescence staining approaches. All cells utilized for these experiments were washed twice with cold PBS/2% FBS, suspended at 10$^7$/ml PBS/1% FBS. Primary antibodies, anti-CLA, -CD15s, -CD34, -CD43, -CD44, -CD62L, -PSGL-1 (PSL-275, and PL-1) along with the appropriate isotype-matched control antibodies were incubated with the cells for 30 min. on ice. Following two washes with PBS/2% FBS, cells were resuspended in PBS/1% FBS and incubated with respective fluorochrome-conjugated secondary antibodies (2 µl) for 30 min. on ice. Cells were washed twice with PBS/2% FBS, resuspended in PBS and flow cytometry was performed on a FACScan apparatus equipped with an argon laser tuned at 488 nm (Becton Dickinson).

Radiolabeling of Human HC Membrane Proteins, SDS-PAGE and Western Blotting.

Cell cultures (1-2×10$^6$ cells/nil) were incubated with [$^{35}$S] EasyTag™-L-Methionine (150 µCi/ml) (NEN™, Boston, Mass.) in RPMI-1640 medium without methionine for 8 hr before membrane protein preparation. Membrane proteins were prepared as previously described. For SDS-PAGE and Western blotting, membrane preparations or immunoprecipitates were diluted in reducing sample buffer and separated on 7% SDS-PAGE gels. For autoradiography, gels resolving [$^{35}$S]-labeled immunoprecipitates were dried and exposed to Kodak BioMax MR film (Fisher Scientific) for 3 hr. For Western blotting, resolved membrane proteins were transferred to Sequi-blot™ PVDF membrane (Bio-Rad, Inc., Hercules, Calif.) and blocked with PBS/0.1% Tween-20/60% FBS for 2 hr at 4° C. Blots were incubated with rat IgM anti-human CLA HECA-452 (1.2 µg/ml)), rat IgG anti-human CD44 Hermes-1 (1 µg/ml) or anti-human PSGL-1 Ab PL-2 (1 µg/ml) for 1 hr at RT. Isotype control immunoblots using either rat IgM, rat IgG or mouse IgG were performed in parallel to evaluate non-specific reactive proteins. After three washes with PBS/0.1% Tween-20, blots were incubated with the respective secondary Ab, AP-conjugated rabbit anti-rat IgM Abs (1:400), goat anti-rat IgG or goat anti-mouse IgG (1:8000) (Zymed Labs. Inc., San Francisco, Calif.). AP substrate, Western Blue® (Promega, Madison, Wis.) was then added to develop the blots.

Hydrodynamic Parallel-Plate Flow Chamber Analysis
L-Selectin-Mediated Adhesive Interactions Using the parallel-plate flow chamber under defined shear stress conditions, L-selectin-mediated adhesive interactions between human HCs and L-selectin naturally expressed on leukocytes (Lawrence, M. B., McIntire, L. V. and Eskin, S. G. (1987) Blood 70(5), 1284-1290) was studied. Leukocyte tethering and rolling on human HC monolayers was visualized by video microscopy in real time using the parallel-plate flow chamber prepared in the following manner. Prior to experimentation, leukocytes were washed twice in HBSS and then suspended at $10^7$/ml in HBSS/10 mM HEPES/ 2mMCaCl$_2$ (H/H/Ca$^{++}$). Negative control groups were prepared by treating cells with PMA (50 ng/ml H/H/Ca++ for 1hr at 37° C.) to induce the cleavage of L-selectin from the cell surface, by pretreating with moAb HRL-1 (10 µg/ml) to block L-selectin binding, or by incubating with 5 mM EDTA to chelate Ca$^{++}$ required for L-selectin binding. To prepare human HC monolayers (100% confluent), suspensions of HCs (KG 1a, HL60, RPMI 8402, K562) at $2\times10^6$/ml RPMI-1640 without Na+Bicarbonate/2% FBS were seeded in 6-well plates at $5\times10^6$/well, centrifuged to layer cells then fixed in 3% glutaraldehyde. Reactive aldehyde groups were blocked in 0.2M lysine, and plated cells were suspended H/H/Ca$^{++}$. To assess the dependence of binding by sialic acid residues on L-selectin ligands, cells were pretreated with *Vibrio cholerae* neuraminidase (0.1 U/mlH/H/Ca$^{++}$ for 1hr at 37° C.). To examine the contribution of sialomucins (including PSGL-1) and PSGL-1 alone, OSGE (60 µg/ml H/H/Ca$^{++}$ for 1hr at 37° C.) or mocarhagin (10 µg/ml for 20 min at 37° C.) treatments were performed, respectively. Furthermore, since HCELL is expressed on KG1a cells and sialylated N-glycosylations on HCELL are critical for L-selectin ligand activity (Sackstein, R. and Dimitroff, C. J. (2000) *Blood* 96, 2765-2774) the contribution of HCELL on KG1a cells was distinguished by first cleaving all of the sialic acid residues from the cell surface with *Vibrio cholerae* neuraminidase (0.1 U/ml for 1hr at 37° C.) and then incubating the cells with a metabolic inhibitor of N-glycosylation, tunicamycin (15 µg/ml for 24 hr at 37° C., 5% CO2), to prevent de novo synthesis of N-glycans (i.e., HECA-452 epitopes on CD44/HCELL). Neuraminidase pretreatment removed all of the residual HCELL activity from the cell surface, and therefore, this treatment approach allowed for the assessment of newly synthesized HCELL on the cell surface. HC cytospin preparations were prepared in multi-well plates as described above. The parallel-plate flow chamber was placed on top of the cell monolayers and leukocytes were perfused into the chamber. After allowing the leukocytes to contact the cell monolayers at a shear stress of 0.5 dynes/cm$^2$ (at which they do not engage in adhesion events), we adjusted the flow rate accordingly to exert shear stress from 1 to >30 dynes/cm$^2$. The number of leukocytes rolling in one frame of five independent fields under 200× magnification at shear stress of 0.2, 0.4, 0.8, 2.2, 4.4, 8.8, 17.6 and 26.4 dynes/cm$^2$ were quantified. A minimum of 3 experiments was performed over the entire range of shear stress and results were expressed as the mean±standard deviation.

P-Selectin-Mediated Adhesive Interactions.

In these experiments, glutaraldehyde-fixed HC monolayers were prepared in 6-well plates as described above, and, where indicated, cells were pretreated with mocarhagin (10 µg/ml) for 30 min. and washed extensively with RPMI1640 without Na+Bicarbonate/2% FBS prior to fixation. To study P-selectin adhesive interactions, confluent CHO cells stably expressing full-length P-selectin (CHO-P) or empty vector (CHO-Mock) were released from flasks with 5 mM EDTA, washed extensively in H/H/Ca$^{++}$ and resuspended at $2\times10^6$/ml for utilization in the parallel-plate flow chamber. P-selectin expression on CHO-P cells was confirmed by flow cytometric analysis. Cell suspensions containing 5 mM EDTA or anti-P-selectin moAbs (10 µg/ml for 30 min. on ice) were utilized as negative controls to confirm calcium-dependent binding. Cells were perfused into the chamber and allowed to fall onto cell monolayers before commencing the assessment of P-selectin adhesion at 0.2, 0.4, 0.8, and 2.2 dynes/cm$^2$. Cellular tethering and rolling was visualized at 100× magnification and quantified and analyzed as described above.

Stamper-Woodruff Assay.

L-Selectin-Mediated Lymphocyte Adherence to HCELL and to PSGL-1.

Molar equivalents of immunoaffinity purified HCELL or PSGL-1 (0.75 µg of reduced HCELL (100 kDa) and 1 µg of fully reduced PSGL-1 (140 kDa)) were spotted onto glass slides and allowed to dry. These protein spots were then fixed in 3% glutaraldehyde, unreactive aldehyde groups were blocked in 0.2M lysine and slides were kept in RPMI-1640 without NaBicarbonate/2% FBS until ready for testing. Lymphocytes ($10^7$/ml RPMI-1640 without NaBicarbonate/ 5% FBS) were overlayed onto these fixed immunoprecipitates and incubated on an orbital shaker at 80 rpm for 30 min. at 4° C. The number of adherent lymphocytes was quantified by light microscopy using an ocular grid under 100× magnification (a minimum of 5 fields/slide, 2 slides/ experiment, and 3 separate experiments). Data were presented as the mean number of bound lymphocytes±standard deviation. KG1a CD34 and L-selectin control immunoprecipitates were also tested in this manner. To verify the dependence for sialic acid, glutaraldehyde-fixed spots were treated with *Vibrio cholerae* neuraminidase (0.1 U/ml RPMI-1640 without NaBicarbonate/2% FBS for 1hr at 37° C.). In addition, to verify that cellular adhesion was dependent on L-selectin, all assays included negative controls, in which lymphocytes were treated with PMA (50 ng/ml for 30 min at 37° C.) or functional blocking antibodies (anti-rat-L-selectin moAb HRL-1 or anti-human L-selectin moAb LAM1-3; 10 µg/ml), or lymphocyte suspensions contained 5 mM EDTA.

L-Selectin-Mediated Lymphocyte Adherence to Human HCs.

For analysis of cellular L-selectin ligand activity of human HCs, cytospin preparations of KG1a, HL60, RPMI-8402 and K562 cells, and of de novo leukemia blasts were fixed in 3% glutaraldehyde, blocked in 0.2M lysine and overlayed with lymphocytes ($10^7$cells/ml RPMI-1640 without Na+Bicarbonate/5% FBS) on an orbital shaker at 80 rpm for 30 min. at 4° C. Slides were then carefully washed with PBS, and bound lymphocytes were fixed in 3% glutaraldehyde. All assays included negative controls as described above. Data were presented as the mean (±S.D.) number of bound lymphocytes at 100× magnification from a minimum of 5 fields/slide in duplicate slides from 3 separate experiments.

B. HCELL is Capable of Engaging with L-Selectin Over a Wide Range of Shear Stress.

The goal of this study was to assess the capability of HCELL and PSGL-1 on human HCs to support shear-dependent L-selectin binding activity over a range of shear stress. The L-selectin binding characteristics of each of these molecules were analyzed by performing shear-based adherence assay systems using human HCs that expressed HCELL and/or PSGL-1: KG1a (HCELL+/PSGL-1+), HL60 (HCELL−/PSGL-1+), RPMI 8402 (HCELL−/PSGL-1+), K562 (HCELL−/PSGL-1−) and a de novo acute myeloid leukemia (AML) without maturation (M1) (HCELL+/ PSGL-1+) (Table 2) (Oxley, S. M. and Sackstein, R. (1994) *Blood* 84(10), 3299-330: Sackstein, R., Fu, L. and Allen, K. L. (1997) *Blood* 89(8), 2773-2781; Sackstein, R. and Dimitroff, C. J. (2000) *Blood* 96, 2765-2774.)

TABLE 1

Flow Cytometric Analysis of Sialoglycoconjugates on Hematopoietic Cell Lines

| Hematopoietic Cell Lines[1] | % Positive Cell Staining* | | | | | | | |
|---|---|---|---|---|---|---|---|---|
| | CD15s | CD34 | CD43 | CD44 | CD45 | PSGL-1 | CLA | CD62L |
| KG1a (Myeloid) | ++++ | ++++ | ++++ | ++++ | ++++ | ++++ | ++++ | +++ |
| K562 (Erythroid) | − | − | ++++ | + | − | − | − | − |
| RPM 8402 (Lymphoid) | − | ++++ | ++++ | ++++ | ++++ | +++ | − | ++++ |
| HL-60 (Promeyloid) | ++++ | − | ++++ | ++++ | ++++ | ++++ | ++++ | − |

[1]All cell lines were maintained in RPM1640/10%/FBS/1% penicillin-streptomycin and grown to confluency (1-2 × 10$^6$). Cells were then isolated, washed in PBS/2% FBS, suspended at 10$^7$ ml PBS/1% FBS and stained/analyzed as described in the Materials and Methods.
*Percent positive cell staining indicates the number of cells that stain greater than negative control cell staining (autofluorescence or FITC-conjugated secondary Ab alone groups). The percentages are represented as follows − = 0-19%, + = 20-39, ++ = 40-59%, +++ = 60-79% and ++++ = 80-100%.

Using the parallel-plate flow chamber under defined hydrodynamic shear stress, L-selectin-mediated tethering and rolling of leukocytes over glutaraldehyde-fixed human HC monolayers was observed. All experiments included negative controls to verify the sole contribution of L-selectin in mediating cell-cell adherence. A shear stress threshold of ~0.5 dynes/cm$^2$ was required for L-selectin-mediated adhesive interactions in this system as previously demonstrated (Lawrence, M. B., Kansas, G. S., Kunkel, E. J. and Ley, K. (1997) *J. Cell Biol.* 136(3), 717-727; Finger, E. B., Puri, K. D., Alon, R., Lawrence, M. B., von Andrian, U. H. and Springer, T. A. (1996) *Nature* 379(6562):266-269.) (FIG. 12A). After reaching this level of shear stress, leukocyte tethering and rolling was enumerated over a broad shear stress range. L-selectin-dependent human lymphocyte and rat TDL rolling on HL60 cells at a shear stress range of 0.4 dynes/cm$^2$ to a maximum of 10 dynes/cm$^2$ was observed (FIG. 12A). However, there was no evidence of lymphocyte rolling on K562 cells, and, despite high PSGL-1 expression, RPMI 8402 cells also did not display L-selectin ligand activity (FIG. 12A and Table 2). In contrast, L-selectin-mediated human lymphocyte and rat TDL rolling on KG1a cell monolayers was observed at shear stress levels in excess of 26 dynes/cm$^2$, whereas, on HL60 cells, human lymphocyte/TDL rolling was absent past 17 dynes/cm$^2$ (FIG. 12A). In addition, the frequency of rolling lymphocytes on KG1a cells was up to a 5-fold greater over the entire range of shear stress that supported L-selectin-mediated rolling on HL60 cells (FIG. 12A). The disparity between the high L-selectin ligand activity on KG1a cells and low activity on HL60 cells was also observed by using human neutrophils, which expressed equivalent levels of L-selectin by flow cytometric analysis: KG1a cells supported 4-fold greater L-selectin-mediated neutrophil rolling than that on HL60 cells (FIG. 12B). These data show that KG1a cells possess greater capacity to support L-selectin mediated leukocyte adherence over a broader range of shear stress and that L-selectin natively expressed on lymphocytes or on neutrophils exhibits comparable binding activity to HCELL or to PSGL-1 expressed on human HCs.

To distinguish the contribution of PSGL-1 activity from HCELL activity on KG1a cells, enzymatic digestion of cells with OSGE or mocarhagin, or incubated cells with a functional blocking Ab PL-1 that both render PSGL-1 incapable of binding to L-selectin was performed (Spertini, O., Cordey, A. S., Monai, N., Giuffre, L. and Schapira, M. (1996) *J Cell Biol.* 135(2), 523-531; Guyer, D. A., Moore, K. L., Lyman, E. B., Schammel, C. M. G., Rogelj, S., McEver, R. P. and Sklar, L. A. (1996) *Blood* 88, 2415-2421; Tu, L., Chen, A., Delahunty, M. D., Moore, K. L., Watson, S. R., McEver, R. P. and Tedder, T. F. (1996) *J. Immunol.* 157, 3995-4004; De Luca, M., Dunlop, L. C., Andrews, R. K., Flannery, J. V., Ettling, R., Cumming, D. A., Veldman G. M. and Berndt, M. C. (1995) *J. Biol. Chem.* 270(45), 26734-26737 14-16). Alternatively, to distinguish the contribution of HCELL activity on KG1a cells (which is expressed exclusively on sialylated N-glycans), KG1a cells and blasts from the de novo leukemia were pretreated with neuraminidase then incubated in tunicamycin. Accordingly, L-selectin ligand activity of KG1a cells was resistant to enzymatic digestion with OSGE or mocarhagin, and PL-1 antibody treatments (Table 3). However, KG1a L-selectin ligand activity was eliminated following neuraminidase digestion, re-expression of ligand activity was markedly reduced following tunicamycin treatment, while ligand activity of cells treated with DMSO alone (control) returned to baseline levels (p<0.001) (Table 3). These data show that N-glycan-dependent HCELL is the primary mediator of L-selectin binding on KG1a cells. In contrast, L-selectin ligand activity of HL60 cells was completely eliminated by digestion with OSGE (p<0.001) (Table 3), and significantly inhibited following mocarhagin digestion (p<0.001) and by treatment with functional blocking anti-PSG1-1 PL-1 monoclonal antibody (p<0.002) (Table 3). The effectiveness of OSGE and mocarhagin treatments were confirmed by flow cytometric analysis of the sensitive epitopes on CD34 and PSGL-1 with moAb QBEND-10 and moAb PSL-275, respectively. Interestingly, the fact that L-selectin ligand activity on HL60 cells was completely eliminated following OSGE digestion, but not by PL-1 moAb or mocarhagin treatments, suggests that HL60 cells express other non-PSGL-1, 0-sialoglycoprotein L-selectin ligands. These data are consistent with previous studies demonstrating the expression of OSGE-sensitive, non-PSGL-1 L-selectin ligand(s) on HL60 cells (Ramos, C., Smith, M. J., Snapp, K. R., Kansas, G. S., Stickney, G. W., Ley, K. and Lawrence, M. B. (1998) *Blood* 91(3), 1067-1075).

TABLE 3

L-selectin Ligand Activity of KG1a and HL60 Cells Following Enzymatic or Blocking Antibody Cell Treatments under Hydrodynamic Shear Flow[1]

| Cells and Treatments | % Control Mean Lymphocyte Binding[2] |
|---|---|
| KG1a Cells + mocarhagin[4] | 110.0 ± 10.5 |
| + OSGE (60 µg/ml)[5] | 104.2 ± 17.1 |
| + PL-1 (anti-PSGL-1; 10 µg/ml) | 104.8 ± 18.0 |
| + neuraminidase (Neur.) (0.1 U/ml) | 0.3 ± 0.8* |
| + Neur. + DMSO | 103.3 ± 12.3 |
| + Neur. + Tunicamycin (15 µg/ml) | 34.3 ± 9.8* |
| HL60 Cells + mocarhagin | 50.0 ± 2.0* |

TABLE 3-continued

L-selectin Ligand Activity of KG1a and HL60 Cells Following
Enzymatic or Blocking Antibody Cell Treatments under
Hydrodynamic Shear Flow[1]

| Cells and Treatments | % Control Mean Lymphocyte Binding[2] |
|---|---|
| + OSGE | 12.5 ± 0.2* |
| + PL-1 | 62.5 ± 1.0** |
| Negative Controls[3] | <0.5 ± 0.3* |

[1]Using the parallel-plate flow chamber, thoracic duct lymphocytes (10 ml/ml H/H with Ca$^{++}$) were perfused over glutaraldehyde-fixed monolayers of cells treated with either mocarhagin (10 µg/ml; 1 hr at 37° C.), OSGE (60 µg/ml; 1 hr at 37° C.), PL-1 (10 µg/ml; 30 min. on ice) at a defined shear stress of 4.4 dynes/cm$^2$.
[2]Mean lymphocyte binding from 5 fields of view from triplicate samples and a minimum of 3 experiments was divided by the mean lymphocyte binding of the untreated control cells for each respective treatment group.
[3]Negative control groups consisted of 5 mM EDTA containing assay medium and anti-L-selectin antibody-treated (HRL-1; 10 µg/ml) rat lymphocytes.
[4]Mocarhagin digestion was verified by the inability of anti-PSGL-1 moAb PSL-275 to recognize the P-and L-selectin binding determinant or mocarhagin-sensitive epitope on PSGL-1 by flow cytometry.
[5]OSGE activity was confirmed by the inability of anti-CD34 Qbend-10 to recognize its OSGE-sensitive epitope on CD34 by flow cytometry.
*Statistically significant difference in lymphocytye binding compared with untreated control cells; Student's paired t-test, p < 0.001.
**Statistically significant difference in lymphocyte binding compared with untreated control cells; Student's paired t-test, p < 0.002.

Figure 12C:
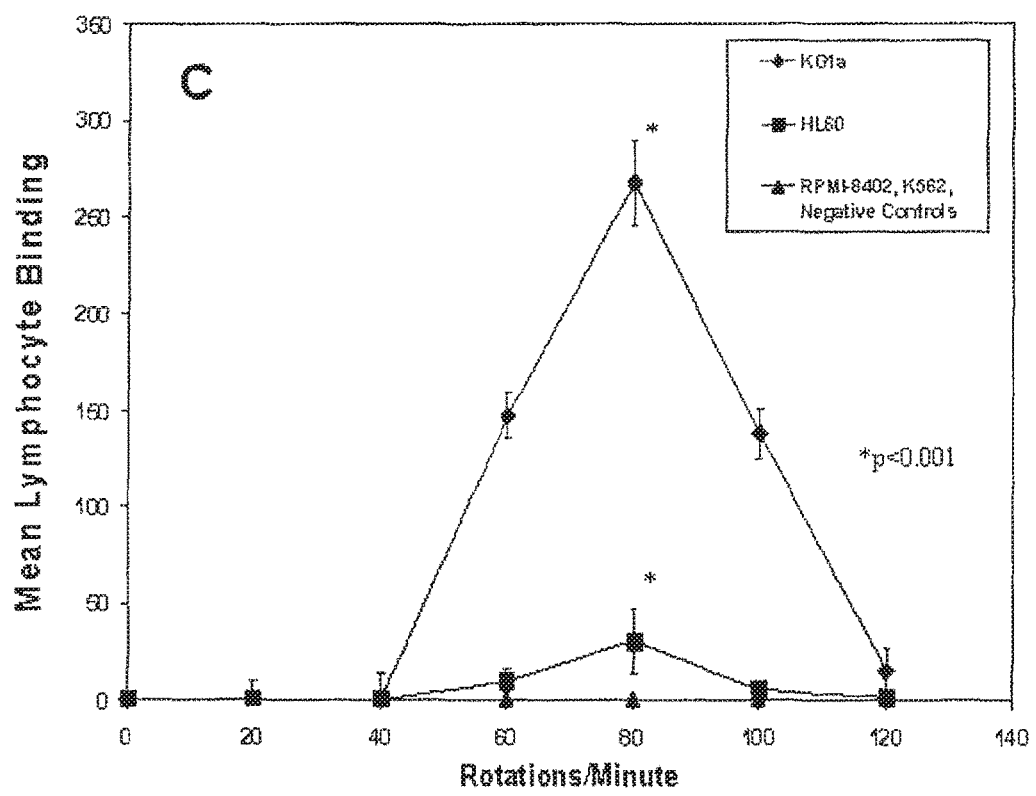
FIG. 12A is a bar chart showing the results of lymphocyte rolling on glutaraldehyde-fixed hematopoietic cell lines, KG1a, HL60, K562 and RPMI 8402 over a range of shear stress.
FIG. 12B is a bar chart showing the results of neutrophil rolling on glutaraldehyde-fixed hematopoietic cell lines, KG1a, HL60, K562 and RPMI 8402 over a range of shear stress.
FIG. 12 C is graph showing the results of the shear-based Stamper-Woodruff assay evaluating the ability of KG1a, HL60, K562 and RPMI 8402 cell lines to support L-selectin-mediated lymphocyte binding over a range of rpms. Mean lymphocyte adherence to KG1a cells was 10-fold greater than on HL60 cells (Student's paired t-test; p<0.001). All L-selectin-mediated lymphocyte adherence was prevented by pretreating lymphocytes with anti-L-selectin monoclonal antibodies (10 µg/ml), by using PMA-treated lymphocytes, and or by using assay medium containing 5 mM EDTA.

To further investigate the L-selectin ligand activities of HCELL and PSGL-1 expressed on human HCs, Stamper Woodruff assays of L-selectin-mediated lymphocyte adherence to glutaraldehyde-fixed HC monolayers under a range of rpms were performed. KG1a cells possessed HCELL ligand activity from >40-120 rpm, which was maximal at 80 rpm, while HL60 cells exhibited L-selectin ligand activity predominantly at 80 rpm (FIG. 12C). In addition, L-selectin-mediated lymphocyte adherence to KG1a cells was 10-fold higher than that of HL60 cells at 80 rpm, and there was no evidence of lymphocyte binding to K562 and RPMI-8402 cells (FIG. 12C). Since the primary L-selectin ligand on HL60 cells is PSGL-1 and its expression is equivalent on KG1a and HL60 cells, these data further suggest that, on a per cell basis, KG1a HCELL activity possesses a higher capacity to function as a ligand over a wider range of shear stress.

Though the level of expression of PSGL-1 is equivalent between HL60 and KG1a cells, it was examined whether PSGL-1 on KG1a cells was functioning equivalently to that of PSGL-1 on HL60 cells. Since the critical N-terminal binding determinant of PSGL-1 for P-selectin overlaps with the structural binding determinant(s) for L-selectin (Snapp, K. R., Ding, H., Atkins, K., Warnke, R., Luscinskas, F. W. and Kansas, G. S. (1998) Blood 91, 154-164; De Luca, M., Dunlop, L. C., Andrews, R. K., Flannery, J. V., Ettling, R., Cumming, D. A., Veldman G. M. and Berndt, M. C. (1995) J. Biol. Chem. 270(45), 26734-26737), it was reasoned that P-selectin binding capabilities of KG1a and HL60 cells correlates with the efficiency of PSGL-1 binding to L-selectin. Thus, flow chamber assays of P-selectin ligand activity utilizing Chinese hamster ovary cells transfected with cDNA encoding full-length human P-selectin (CHO-P) was performed. Both HL60 and KG1a cells supported equivalent PSGL-1-mediated CHO-P cell rolling, and K562 and RPMI-8402 cells did not possess any activity (FIG. 13A). P-selectin ligand activity on KG1a and HL60 cells was prevented following mocarhagin treatment (FIG. 13B). Unlike the differential capability to support L-selectin ligand activity between KG1a and HL60 cells, these data suggested that native PSGL-1 as expressed in the cell membrane was similar both structurally and functionally in these cell lines. Of note, RPMI-8402 PSGL-1 was non-functional as both an L- or P-selectin ligand, consistent with a finding that PSGL-1 on certain lymphoid cells is non-functional due to a lack of activity of α1,3 fucosyltransferases and core 2 β1,6 N-acetylglucosaminyltransferases required for creation of a bioactive ligand (Vachino, G, Chang, X.-J., Veldman, G. M., Kumar, R., Sako, D., Fouser, L. A., Berndt, M. C. and Cumming, D. A. (1995) J. Biol. Chem. 270(37), 21966-21974).

C. HCELL is the Preferred L-Selectin Ligand on Human HCs.

The distinction in L-selectin ligand activity between HCELL and PSGL-1 on whole cells may reflect differences in surface density and/or membrane topography of the expression of these molecules. To directly compare the binding capacities of HCELL and PSGL-1, conventional, shear-based Stamper Woodruff assays of L-selectin-mediated lymphocyte adherence to molar equivalents of either HCELL or PSGL-1 immunoaffinity purified from KG1a and HL60 cells, and from a de novo AML (M1) was performed.

Figure 14B:
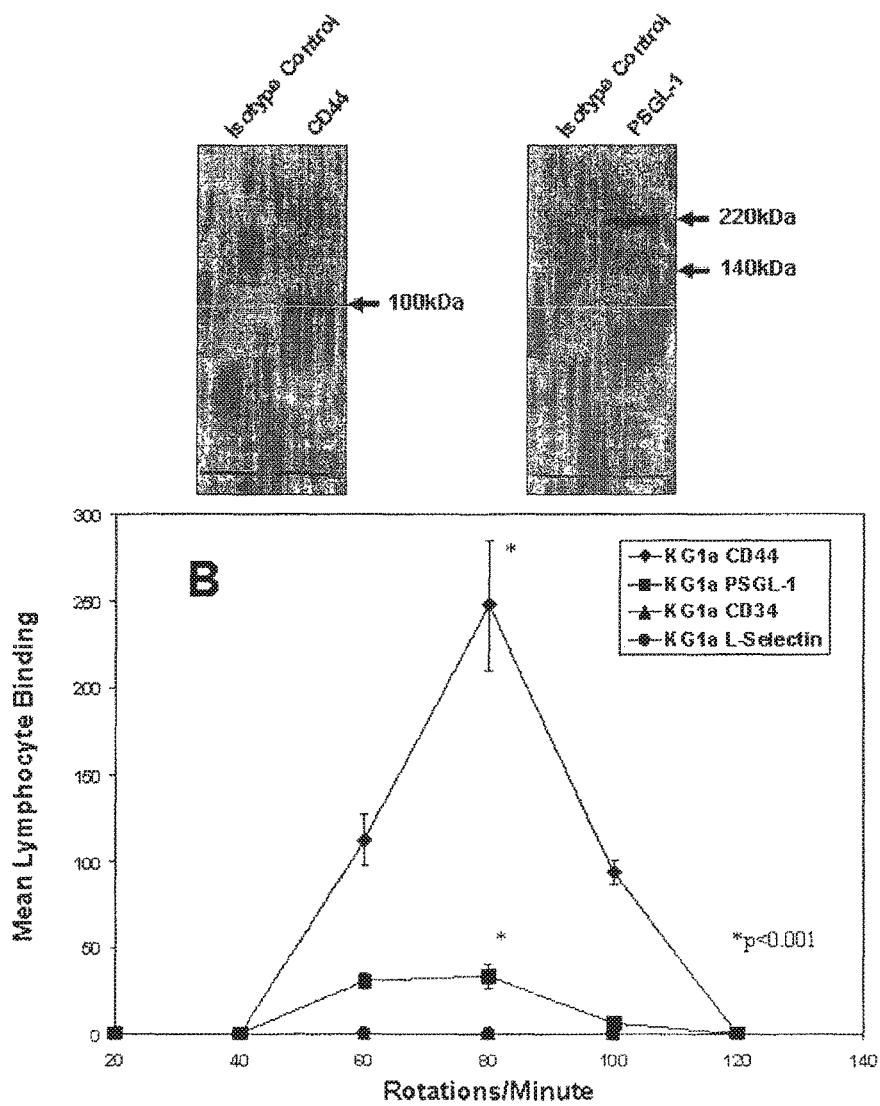
FIG. 14B is a chart showing the results of a Stamper-Woodruff assays of immunoprecipitated KG1a CD44 (1.5 µg) and PSGL-1 (3 µg).

To isolate HCELL and PSGL-1 for cell binding experiments, KG1a CD44 (Hermes-1 rat IgG) and PSGL-1 (PL-2 mouse IgG) from cell membrane protein preparations were immunoaffinity purified. Autoradiography of Hermes-1 and PL-2 immunoprecipitates obtained from whole cell lysates of [$^{35}$S]-metabolically radiolabeled KG1a cells showed the specificity of Hermes 1 and PL-2 for their respective antigens (FIG. 14A), revealing that the 100 kDa form of CD44 was principally isolated and that both dimer (~220 kDa) and monomer (~140 kDa) isoforms of PSGL-1 were isolated (FIG. 14A). There was a minor contaminant protein of 30 kDa immunoprecipitated by Hermes 1, which was removed by subsequent passage of immunoprecipitates through a 50 kDa MW cut-off filter. To normalize for molar equivalency of purified protein utilized in Stamper-Woodruff assays, the densitometric optical density (OD) of [$^{35}$S]-methionine-labeled CD44 and PSGL-1 (each passed through 50 kDa cut-off filter) on autoradiograms of immunoaffinity purified material spotted onto glass was compared. It was found that the OD of 1 µg PSGL-1 was 2-fold greater than the OD of 0.75 µg CD44. Since monomer PSGL-1 (140 kDa) is ~1.4-fold higher MW than CD44 (100 kDa) and since PSGL-1 has twice as many methionine residues than CD44 (13 vs. 6), the two-fold higher signal of PSGL-1 indicated that 0.75 µg CD44 and 1 µg PSGL-1 represent equimolar amounts of the respective proteins. Using these equimolar amounts, CD44 supported up to 10-fold greater lymphocyte binding compared with PSGL-1 at 80 rpm, and supported a 5- to 10-fold higher lymphocyte adherence compared with PSGL-1 from 40 to 100 rpm (FIG. 14B). CD34 and L-selectin immunoprecipitated from KG1a cells (negative molecular controls) did not support any L-selectin-mediated lymphocyte adherence (FIG. 14B). These data directly comparing the relative L-selectin binding efficiencies of purified CD44 and PSGL-1 were similar to results obtained from whole cell analysis.

To explore whether disparate HCELL and PSGL-1 L-selectin ligand activities were also present in native human hematopoietic cells, the L-selectin ligand activity of HCELL and PSGL-1 on circulating blasts from a patient with an AML without maturation (M1) was investigated. In preliminary Stamper-Woodruff assays of whole AML (M1) cell activities, AML (M1) cells showed comparable L-selectin ligand activity to that of KG1a cells, and the expression of CD44 and PSGL-1 (measured by flow cytometry) was also similar to that of KG1a. CD44 and PSGL-1 from these cells was immunoprecipitated and their binding capacity by Stamper-Woodruff assay (80 rpm) was examined. In parallel, L-selectin ligand activities of HCELL and PSGL-1 from KG1a and HL60 cells were also assessed, and digestions with N-glycosidase-F and OSGE were performed for comparative analysis. CD44 from both KG1a and AML (M1) supported significantly greater L-selectin-mediated lymphocyte adherence than PSGL-1 from KG1a, HL60 or AML (M1) (3-fold higher mean number of lymphocytes bound to CD44 than to PSGL-1; p<0.001) (Table 4). In addition, neither CD44 from HL60, isotype control immunoprecipitates, CD34 and L-selectin immunoprecipitates, or neuraminidase-treated CD44 and PSGL-1 immunoprecipitates from KG1a cells (Table 4) possessed any L-selectin ligand activity. Similar to N-glycosidase-F treated CD44 from KG1a cells, the L-selectin binding activity of N-glycosidase-F treated AML M1 CD44 was markedly reduced (to background levels) (Table 4). Interestingly, PSGL-1 isolated from KG1a cells and AML (M1) blasts possessed a greater capacity to engage with L-selectin than PSGL-1 from HL60 cells (Table 4), even though P-selectin mediated binding to native PSGL-1 was identical between KG1a and HL60 cells (FIGS. 13A and 13B). Photomicrographs of lymphocytes bound to CD44 or PSGL-1 in Stamper-Woodruff assays illustrated the distinctive differences in the range of L-selectin ligand activity of KG1a CD44 and AML (M1) CD44 (FIGS. 15A and 15D, respectively) compared to KG1a PSGL-1 (FIG. 15G); even at 3-fold molar excess of KG1a PSGL-1 (FIG. 15H), L-selectin ligand activity of CD44 (FIG. 15A) was still greater than that of PSGL-1. N-glycosidase-F (FIGS. 15B and 15E) and OSGE (FIG. 15I) treatments markedly diminished lymphocyte binding comparable to isotype control levels (FIGS. 15C and 15F) confirming the relevant contributions of N-glycans and O-glycans on HCELL and PSGL-1, respectively.

TABLE 4

L-selectin Ligand Activity of Immunoprecipitated CD44 and PSGL-1 from KG1a, HL60 Cells and Blasts from an AML (M1) in the Stamper-Woodruff Assay[1]

| Cellular L-selectin Ligand | Mean Number of Bound Lymphocytes[2] |
|---|---|
| KG1a CD44 | 357.8 ± 36.6 |
| N-glycosidase-F CD44 | 30.7 ± 18.4* |
| Isotype Control | 23.3 ± 7.1* |
| PSGL-1 | 44.8 ± 6.7** |
| Isotype Control | 11.0 ± 1.6* |
| CD34 (Molecular Control) | 4.0 ± 2.0** |
| L-selectin (Molecular Control) | 0.5 ± 0.6** |
| Isotype Control | 8.5 ± 3.5 |
| HL60 CD44 | 6.5 ± 3.6 |
| Isotype Control | 5.4 ± 2.3 |
| PSGL-1 | 11.0 ± 2.1* |
| Isotype Control | 3.1 ± 2.9* |
| AML (M1) CD44 | 425.3 ± 9.5 |
| N-glycosidase-F CD44 | 23.4 ± 6.1* |
| Isotype Control | 34.3 ± 4.1* |
| PSGL-1 | 141.5 ± 22.6** |
| Isotype Control | 19.5 ± 6.2* |

[1]Rat thoracic duct lymphocytes (1 × 10[7]/ml) were overlayed onto glutaraldehyde-fixed spots of immunoaffinity purified CD44 (Hermes-1), N-glycosidase-F-treated CD44, CD34 (QBend-10), L-selectin (LAM 1-3) or isotype control (rat IgG or mouse IgG) (each at 0.75 µg/spot), or PSGL-1 (PL-2) (1 µg/spot) and incubated on a shaker at 80 rpm at 4° C.
[2]The average number of bound lymphocytes from 5 fields of view at 100× mag. from duplicate slides and a minimum of three experiments. Each experiment included anti-L-selectin Ab-treated (HRL-1; 10 µg/ml) or PMA-treated lymphocytes and 5 mM EDTA containing assay medium groups, or Vibrio cholerae neuraminidase-treated spots (ligand), which all completely eliminated lymphocyte binding (<0.8 mean number of bound lymphocytes).
*Statistically significant difference in lymphocyte binding to treatment or isotype immunoprecipitate compared with each respective untreated cell molecule; Student's t-test, p < 0.001.
**Statistically significant difference in lymphocyte binding to these groups compared with lymphocyte binding to untreated KG1a and AML (M1) CD44; Student's t-test, p < 0.001.

Figure 16:
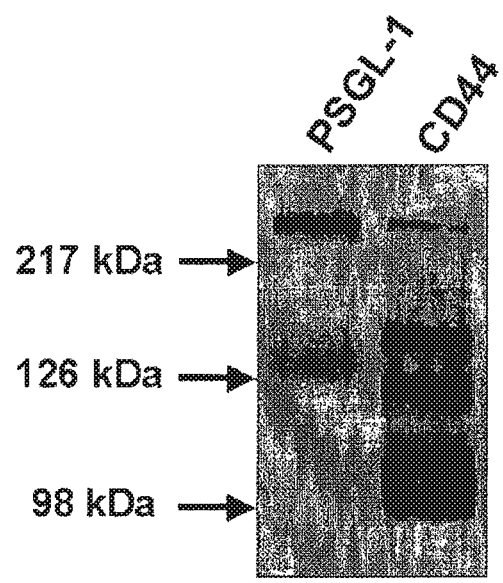
FIG. 16 is a photograph of a Western Blot showing HECA-452 epitope(s) on KG1a CD44 and PSGL-1.

To gain insight into the higher capacity of HCELL to bind to L-selectin compared with that of PSGL-1, the expression of the sialyl-fucosylated structures (recognized by rat moAb HECA-452) on CD44 and on PSGL-1 was examined, which correlates with L-selectin binding capacity. SDS-PAGE and HECA-452 immunoblot analysis of equimolar amounts of CD44 and PSGL-1 immunoprecipitated from KG1a membrane proteins revealed that CD44 was distinctly more HECA-452-reactive than PSGL-1 (FIG. 16), suggesting that HCELL contains a greater number of HECA-452 epitope(s) than PSGL-1, which could account for its higher avidity towards L-selectin.

Example 11

Immunoaffinity Purification of HCELL and PSGL-1

HCELL and PSGL-1 were immunoprecipitated from human HCs. The immunoprecipitation procedure was followed as described (Dimitroff, C. J., Lee, J. Y., Fuhlbrigge, R. C. and Sackstein, R. (2000) Proc. Natl. Acad. Sci. 97(25), 13841-13846). Briefly, membrane proteins of human HCs (Dimitroff, C. J., Lee, J. Y., Fuhlbrigge, R. C. and Sackstein, R. (2000) Proc. Natl. Acad. Sci. 97(25), 13841-13846) were first solubilized in 2% NP-40 and precleared in Protein G-agarose (Life Technologies). Membrane protein was then quantified using Bradford protein assay (Sigma). Solubilized and precleared membrane protein preparations (including [$^{35}$S]-methionine-radiolabeled membrane proteins and whole cell lysates (Dimitroff, C. J., Lee, J. Y., Fuhlbrigge, R. C. and Sackstein, R. (2000) Proc. Natl. Acad. Sci. 97(25), 13841-13846)) were then incubated with anti-PSGL-1 Ab PL-2 or anti-CD44 monoclonal Ab Hermes-1 (a ratio of 100 µg protein:3 µg antibody) for 18 hours at 4° C. on a rotator. Immunoprecipitations with anti-CD34 antibody QBEND-10, anti-L-selectin antibody (LAM1-3) or mouse IgG/rat IgG isotype controls were also performed to serve as negative controls. The antibody-lysate mixture was added to Protein G-Agarose and incubated for 1hr at 4° C. under constant rotation. For SDS-PAGE/Western blotting, immunoprecipitates were washed 5-times with lysis buffer/2% NP-40/1% SDS/1% BSA and 3-times lysis buffer without BSA, and boiled in reducing sample buffer for analysis. For functional assessment of CD44 or PSGL-1 in adherence assays, respective immunoprecipitates were washed 5-times with lysis buffer/2% NP-40/1% SDS/1% BSA and 3-times lysis buffer without NP-40, SDS or BSA, then suspended in PBS and boiled for 5 min. to dissociate CD44 or PSGL-1 from immune complexes. Eluates were then passed through 50 kDa MW cut-off Microcon® filters (Fisher Scientific, Inc.). Protein concentration of the retentate was measured by Bradford protein determination assay.

Parallel experiments were performed wherein respective antibodies were incubated with Protein G-agarose, and immunoprecipitates were boiled in PBS as mentioned above. Eluates analyzed by SDS-PAGE and Coomassie blue staining revealed that >99% of the antibody was still bound to Protein G-agarose after boiling in PBS and, therefore, contributed negligibly to the protein levels quantified. Moreover, with exception of a minor contaminating band at 30 kDa in immunoprecipitates of Hermes-1, other non-CD44 and non-PSGL-1 proteins, respectively, were not isolated by immunoprecipation using Hermes-1 and PL-2 (see autoradiograms of immunoprecipitates obtained from whole cell lysates (7) of [$^{35}$S]-metabolically radiolabeled KG1a cells, FIG. 14A). The use of the 50 kDa cut-off filter removed the contaminating protein of 30 kDa immunoprecipitated by Hermes-1, yielding pure KG1a CD44.

To confirm the contribution of N-glycans on HCELL or O-sialoglycans on PSGL-1, membrane preparations were first treated with either N-glycosidase-F (0.8 U/ml) or OSGE prior to immunoprecipitation as described (Dimitroff, C. J., Lee, J. Y., Fuhlbrigge, R. C. and Sackstein, R. (2000) *Proc. Natl. Acad. Sci.* 97(25), 13841-13846). Immunoaffinity purified material (0.75-3 μg/spot) was spotted onto glass slides for analyses in the Stamper-Woodruff assay (See below for assay description). For autoradiographic analysis of immunoprecipitated [$^{35}$S]-methionine-radiolabeled CD44 and PSGL-1, immunoprecipitates were spotted onto glass slides, allowed to dry and exposed Kodak BioMax-MR film for 12 h at −80° C. Densitometric analysis (optical density) of the autoradiograms was performed with a Hewlett-Packard Scanj et 5200C scanner and NIH Image processing and analysis program.

Example 12

RT-PCR Analysis of α1,3 Fucosyltransferases (FucTIV and FucTVII) and α2,3 sialyltransferase (ST3Gal IV)

As HECA-452 expression is dependent on critical sialofucosylations on core poly-N-acetyllactosaminyl chains, it was investigated whether the relative difference in HECA-452 epitope expression and L-selectin binding activity was a consequence of up-regulated a2,3 sialyltransferase (ST3Gal 1V) and leukocyte a1,3 fucosyltransferases (FucTIV and FucTVII), which are required for biosynthesis of HECA-452 epitope (Sasaki, K., Watanabe, E., Kawashima, K., Sekine, S., Dohi, T., Oshima, M., Hanai, N., Nishi, T. and Hasegawa., M. (1993) *J Biol. Chem.* 268(30), 22782-22787: Fuhlbrigge, R. C., Kieffer, D., Armerding, D. and Kupper, T. S. (1997) *Nature* 389, 978-981; Zollner, O. and Vestweber, D. M. (1996) *J. Biol. Chem.* 271, 33002-33008; Goelz, S., Kumar, R., Potvin, B., Sundaram, S., Brickelmaier, M. and Stanley, P. (1994) *J. Biol. Chem.* 269, 1033-1040).

Total cellular RNA was extracted with Trizol® LS reagent according to manufacturer's protocol (Gibco, Life Sciences) and utilized in the Titan™ One Tube RT-PCR System (Roche Molecular Biochemicals). ST3Gal IV sense 5'-ctctc-cgatatctgttttattttcccatcccagagagaagaaggag-3' and anti-sense 5'-gattaaggtaccaggtcagaaggacgtgaggttctt-3' primers and thermal cycling conditions [RT at 52° C. for 45 minutes, 1 cycle at 94° C. for 2 minutes, 30 cycles at 94° C. for 1 minute, 57° C. for 1 minute and 72° C. for 2 minutes, and 1 cycle at 68° C. for 7 minutes] were used to amplify a 0.96 kb cDNA fragment of ST3Gal IV. To amplify a 0.55 kb cDNA fragment of FucTVII (GenBank, Accn#U08112), specific primers, sense 5'-cccaccgtggcccagtaccgcttct-3' and anti-sense 5'-ctgacctctgtgcccagcctcccgt-3' and thermal cycling conditions [RT at 52° C. for 45 minutes, 1 cycle at 94° C. for 2 minutes, 30 cycles at 94° C. for 30 seconds, 60° C. for 45 seconds and 72° C. for 1 minute, and 1 cycle at 68° C. for 7 minutes] were used. Using identical RT and thermal cycling conditions, a 0.50 kb cDNA fragment of FucTIV was generated from sense 5'-cgggtgtgccaggctgtacagagg-3' and anti-sense 5'-tcgggaacagttgtgtatgagatt-3' primers (GenBank, Accn#M58597).

Figure 17A:
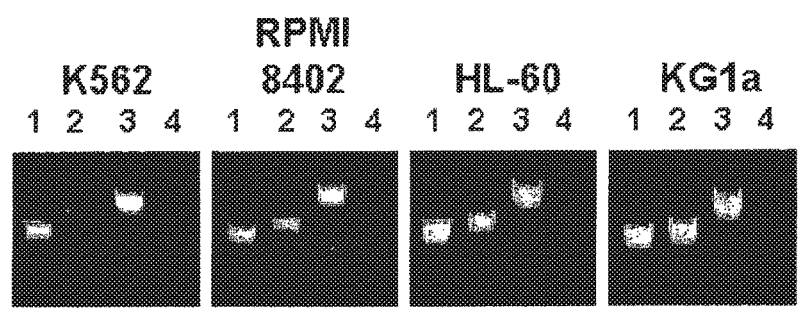
FIGS. 17A-B are photographs showing the expression of glycosyltransferases (FucTIV, FucTVII and ST3GalIV) on human hematopoietic cell Lines.

RT-PCR analysis of FucTIV and FucTVII and of ST3Gal IV gene expression in KG1a, HL60, K562 and RPMI-8402 cells showed that FucTIV expression was relatively similar in all cell lines (FIGS. 17A and 17B), but the FucTVII expression was highest in HL60 and KG1a cells (Lane 1, FucTIV, and Lane 2, FucTVII; FIG. 17A). Interestingly, ST3Gal IV (Lane 1; FIG. 6B) was expressed at a high level in KG1a cells and at a very low level in all other cell lines, suggesting that the inherent level of ST3Gal IV may help regulate the expression of relevant HECA-452-reactive structures and critical L-selectin binding determinants on CD44 and/or PSGL-1.

Figure 17B:
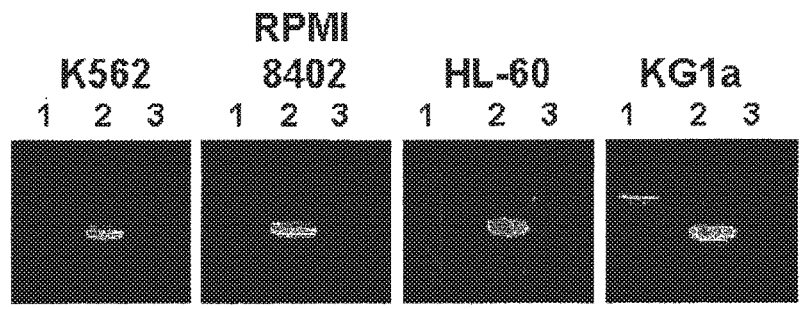

HECA-452 expression is dependent on critical sialofucosylations on core poly-N-acetyllactosaminyl chains. The relative difference in HECA-452 epitope expression and L-selectin binding activity was a consequence of up-regulated a2,3 sialyltransferase (ST3Gal IV) and leukocyte a1,3 fucosyltransferases (FucTIV and FucTVII), which are required for biosynthesis of HECA-452 epitope was investigated. RT-PCR analysis of FucTIV and FucTVII and of ST3Gal IV gene expression in KG1a, HL60, K562 and RPMI-8402 cells showed that FucTIV expression was relatively similar in all cell lines (FIGS. 17A and 17B), but the FucTVII expression was highest in HL60 and KG1a cells (Lane 1, FucTIV, and Lane 2, FucTVII; FIG. 17A). Interestingly, ST3Gal IV (Lane 1; FIG. 17B) was expressed at a high level in KG1a cells and at a very low level in all other cell lines, suggesting that the inherent level of ST3Gal IV may help regulate the expression of relevant HECA-452-reactive structures and critical L-selectin binding determinants on KG1a CD44 and/or PSGL-1.

EQUIVALENTS

From the foregoing detailed description of the specific embodiments of the invention, it should be apparent that novel compositions and applications have been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

What is claimed is:

1. A method of increasing the engraftment potential of a hematopoietic progenitor cell population, the method comprising: (a) providing said hematopoietic progenitor cell population; and (b) contacting said hematopoietic progenitor cell population with a recombinant expression vector comprising a nucleic acid encoding one or more of CD44 polypeptide, α(2,3) sialyltransferase, α(1,3)-fucosyltransferase, or combinations thereof, wherein the nucleic acid encodes a polypeptide that increases binding activity of the hematopoietic progenitor cell population for E-selectin and/or L-selectin, thereby increasing the engraftment potential of the hematopoietic progenitor cell population.

2. The method of claim 1, wherein the α(1,3)-fucosyltransferase is α(1,3)-fucosyltransferase VII (FTVII).

3. The method of claim 1, wherein the α(2,3)-sialyltransferase is α(2,3)-sialyltransferase ST3GalIV.

4. A population of hematopoietic progenitor cells having a glycosylated polypeptide, said glycosylated polypeptide comprising a CD44 polypeptide that displays sialylated, fucosylated glycans that bind E-selectin and L-selectin, the population having a recombinant expression vector comprising a nucleic acid encoding one or more of CD44 polypeptide, α(2,3) sialyltransferase, α(1,3)-fucosyltransferase, or combinations thereof, wherein the nucleic acid increases binding activity of the population for E-selectin and/or L-selectin.

5. A population of ex vivo modified hematopoietic progenitor cells having HCELL activity produced by contacting, ex vivo, a hematopoietic cell population comprising hematopoietic cells having little to no HCELL activity with one or more agents that increases cell-surface expression or activity of a HCELL polypeptide on the cell surface, the agent comprising one or more of α(2,3) sialyltransferase, α(1,3)-fucosyltransferase, or combinations thereof, wherein the agent increases affinity of the population for E-selectin and/or L-selectin.

6. The population of claim 4, wherein the α(1,3)-fucosyltransferase is α(1,3)-fucosyltransferase VII (FTVII).

7. The population of claim 4, wherein the α(2,3)-sialyltransferase is sialyltransferase ST3GalIV.

8. The population of claim 3, wherein the α(1,3)-fucosyltransferase is α(1,3)-fucosyltransferase VII (FTVII).

9. The population of claim 3, wherein the α(2,3)-sialyltransferase is sialyltransferase ST3GalIV.

\* \* \* \* \*